US008148127B2

(12) United States Patent
Udagawa et al.

(10) Patent No.: US 8,148,127 B2
(45) Date of Patent: *Apr. 3, 2012

(54) POLYPEPTIDES HAVING GLUCOAMYLASE ACTIVITY AND POLYNUCLEOTIDES ENCODING SAME

(75) Inventors: Hiroaki Udagawa, Yokohama (JP); Sara Landvik, Vedbaek (DK); Michiko Ihara, Chiba (JP); Jiyin Liu, Raleigh, NC (US); Chee Leong Soong, Raleigh, NC (US); Eric Allain, Boone, NC (US); Shiro Fukuyama, Chiba (JP)

(73) Assignees: Novozymes A/S, Bagsvaerd (DK); Novozymes North America, Inc., Franklinton, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/634,776

(22) Filed: Dec. 10, 2009

(65) Prior Publication Data

US 2010/0216213 A1     Aug. 26, 2010

Related U.S. Application Data

(63) Continuation of application No. 11/872,355, filed on Oct. 15, 2007, now abandoned, which is a continuation of application No. 11/315,730, filed on Dec. 22, 2005, now Pat. No. 7,326,548.

(60) Provisional application No. 60/650,612, filed on Feb. 7, 2005, provisional application No. 60/638,614, filed on Dec. 22, 2004.

(51) Int. Cl.
| | |
|---|---|
| *C12N 9/34* | (2006.01) |
| *C12N 9/30* | (2006.01) |
| *C12P 21/06* | (2006.01) |
| *C12P 21/04* | (2006.01) |
| *C07H 21/04* | (2006.01) |
| *C07K 1/00* | (2006.01) |

(52) U.S. Cl. ...... 435/205; 435/204; 435/69.1; 435/69.7; 536/23.2; 536/23.4; 530/350

(58) Field of Classification Search ................. 435/205, 435/204, 69.1, 69.7; 536/23.2, 23.4; 530/350
See application file for complete search history.

(56) References Cited

U.S. PATENT DOCUMENTS

| | | | |
|---|---|---|---|
| 4,727,046 | A | 2/1988 | Tuntastood et al. |
| 6,352,851 | B1 | 3/2002 | Nielsen et al. |
| 7,326,548 | B2 | 2/2008 | Udagawa et al. |
| 2003/0032163 | A1 | 2/2003 | Nielsen et al. |

FOREIGN PATENT DOCUMENTS

| | | |
|---|---|---|
| WO | 8402921 | 8/1984 |
| WO | 9928448 | 6/1999 |
| WO | 0075296 | 12/2000 |
| WO | 2004011218 | 12/2004 |

OTHER PUBLICATIONS

Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Sen et al., Developments in directed evolution for improving enzyme functions. Appl. Biochem. Biotechnol., 2007, vol. 143: 212-223.*
Wishart et al., A single mutation converts a novel phosphotyrosine binding domain into a dual-specificity phosphatase. J. Biol. Chem., 1995, vol. 270(45): 26782-26785.*
Whisstock et al., Prediction of protein function from protein sequence. Q. Rev. Biophysics., 2003, vol. 36 (3): 307-340.*
Zhao et al., Applied and Environmental Microbiology, vol. 66, No. 6, pp. 2531-2535 (2000).
Nagasaka et al., Applied Microbiol Biotechnology, vol. 44, pp. 451-458 (1995).
Boel et al., EMBO J, vol. 3, No. 5, pp. 1097-1102 (1984).
Guo et al., Proceeding of the National Academy of Sciences, vol. 101, No. 25, pp. 9205-9210 (2004).
Nagasaka et al., Applied Microbiology and Biotechnology, vol. 50, No. 3, pp. 323-330 (1998).
Nagasaka et al., Journal of Applied Glycoscience, vol. 46, No. 2, pp. 169-178 (1999).
Seffernick et al., Journal of Bacteriology, vol. 183, No. 8, pp. 2405-2410 (2001).
Witkowski et al., Biochemistry, vol. 38, pp. 11643-11650 (1999).

* cited by examiner

*Primary Examiner* — Ganapathirama Raghu
(74) *Attorney, Agent, or Firm* — Elias Lambiris

(57) ABSTRACT

The present invention relates to polypeptides having glucoamylase activity and isolated polynucleotides encoding said polypeptides. The invention also relates to nucleic acid constructs, vectors, and host cells comprising the polynucleotides as well as methods for producing and using the polypeptides. The invention also relates to the composition comprising a glucoamylase of the invention as well as the use such compositions for starch conversion processes, brewing, including processes for producing fermentation products or syrups.

17 Claims, 1 Drawing Sheet

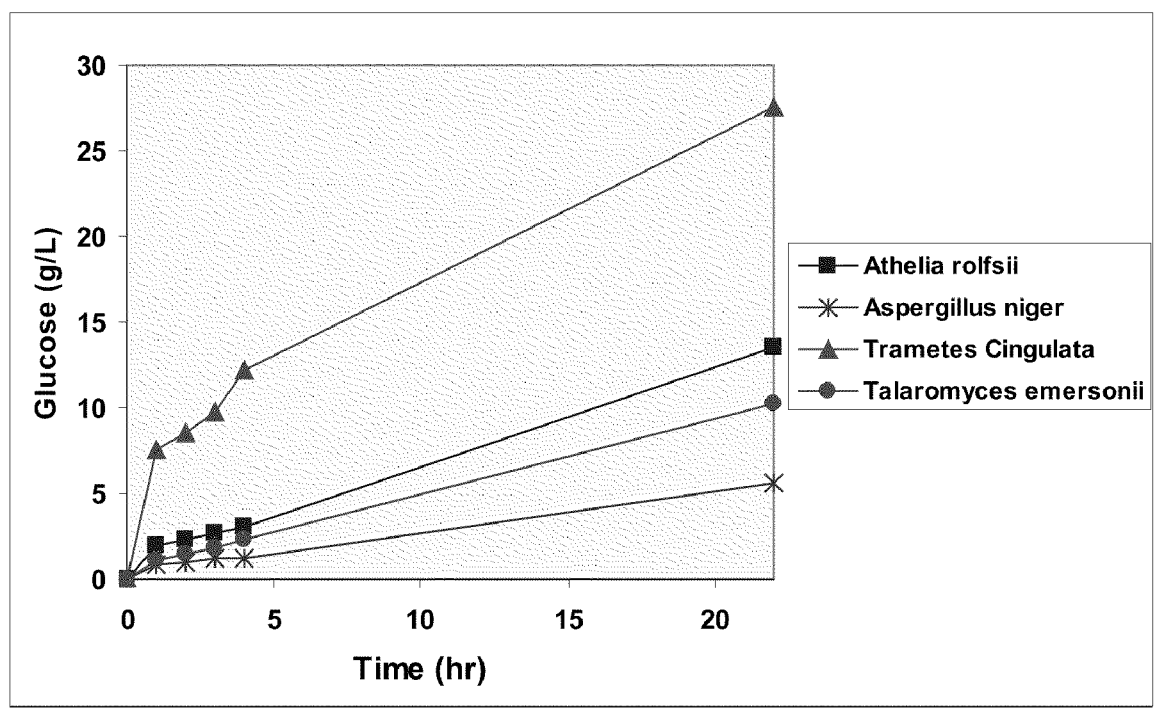

SEQUENCE LISTING

<160> NUMBER OF SEQ ID NOS: 43

<210> SEQ ID NO 1
<211> LENGTH: 2166
<212> TYPE: DNA
<213> ORGANISM: Trametes cingulata
<220> FEATURE:
<221> NAME/KEY: sig_peptide
<222> LOCATION: (1)..(54)
<220> FEATURE:
<221> NAME/KEY: CDS
<222> LOCATION: (1)..(162)
<220> FEATURE:
<221> NAME/KEY: mat_peptide
<222> LOCATION: (55)..(2166)
<220> FEATURE:
<221> NAME/KEY: Intron
<222> LOCATION: (163)..(247)
<220> FEATURE:
<221> NAME/KEY: CDS
<222> LOCATION: (248)..(521)
<220> FEATURE:
<221> NAME/KEY: Intron
<222> LOCATION: (522)..(577)
<220> FEATURE:
<221> NAME/KEY: CDS
<222> LOCATION: (578)..(722)
<220> FEATURE:
<221> NAME/KEY: Intron
<222> LOCATION: (723)..(772)
<220> FEATURE:
<221> NAME/KEY: CDS
<222> LOCATION: (773)..(932)
<220> FEATURE:
<221> NAME/KEY: Intron
<222> LOCATION: (933)..(1001)
<220> FEATURE:
<221> NAME/KEY: CDS
<222> LOCATION: (1002)..(1277)
<220> FEATURE:
<221> NAME/KEY: Intron
<222> LOCATION: (1278)..(1341)
<220> FEATURE:
<221> NAME/KEY: CDS
<222> LOCATION: (1342)..(1807)
<220> FEATURE:
<221> NAME/KEY: misc_feature
<222> LOCATION: (1744)..(1773)
<223> OTHER INFORMATION: Linker region
<220> FEATURE:
<221> NAME/KEY: misc_feature
<222> LOCATION: (1774)..(2166)
<223> OTHER INFORMATION: binding domain
<220> FEATURE:
<221> NAME/KEY: Intron
<222> LOCATION: (1808)..(1864)
<220> FEATURE:
<221> NAME/KEY: CDS
<222> LOCATION: (1865)..(1963)
<220> FEATURE:
<221> NAME/KEY: Intron
<222> LOCATION: (1964)..(2023)
<220> FEATURE:
<221> NAME/KEY: CDS
<222> LOCATION: (2024)..(2163)

<400> SEQUENCE: 1

```
atg cgt ttc acg ctc ctc acc tcc ctc ctg ggc ctc gcc ctc ggc gcg      48
Met Arg Phe Thr Leu Leu Thr Ser Leu Leu Gly Leu Ala Leu Gly Ala
        -15                 -10                 -5 ttc gcg cag tcg agt gcg gcc gac gcg tac gtc gcg tcc gaa tcg ccc      96
Phe Ala Gln Ser Ser Ala Ala Asp Ala Tyr Val Ala Ser Glu Ser Pro
    -1   1               5                  10
```

```
atc gcc aag gcg ggt gtg ctc gcc aac atc ggg ccc agc ggc tcc aag      144
Ile Ala Lys Ala Gly Val Leu Ala Asn Ile Gly Pro Ser Gly Ser Lys
15              20                  25                  30 tcc aac gga gca aag gca agtgacacag tgacactccg gggcgcccat              192
Ser Asn Gly Ala Lys Ala
                35 gcttcattct tctgtgcaca tggtagcgct gacatatcgt tgtttttgac agccc ggc      250
                                                              Gly atc gtg att gca agt ccg agc aca tcc aac ccg aac tac ctg tac aca      298
Ile Val Ile Ala Ser Pro Ser Thr Ser Asn Pro Asn Tyr Leu Tyr Thr
        40                  45                  50 tgg acg cgc gac tcg tcc ctc gtg ttc aag gcg ctc atc gac cag ttc      346
Trp Thr Arg Asp Ser Ser Leu Val Phe Lys Ala Leu Ile Asp Gln Phe
        55                  60                  65 acc act ggc gaa gat acc tcg ctc cga act ctg att gac gag ttc acc      394
Thr Thr Gly Glu Asp Thr Ser Leu Arg Thr Leu Ile Asp Glu Phe Thr
70              75                  80                  85 tcg gcg gag gcc ata ctc cag cag gtg ccg aac ccg agc ggg aca gtc      442
Ser Ala Glu Ala Ile Leu Gln Gln Val Pro Asn Pro Ser Gly Thr Val
                90                  95                  100 agc act gga ggc ctc ggc gag ccc aag ttc aac atc gac gag acc gcg      490
Ser Thr Gly Gly Leu Gly Glu Pro Lys Phe Asn Ile Asp Glu Thr Ala
                105                 110                 115 ttc acg gat gcc tgg ggt cgt cct cag cgc g gtaagtcgga ggttgcctcg      541
Phe Thr Asp Ala Trp Gly Arg Pro Gln Arg
            120                 125 acggagatac gcccagactg acttcaagac tctcag at  ggt ccc gct ctc cgg      594
                                           Asp Gly Pro Ala Leu Arg
                                                        130 gcg act gcc atc atc acc tac gcc aac tgg ctc ctc gac aac aag aac      642
Ala Thr Ala Ile Ile Thr Tyr Ala Asn Trp Leu Leu Asp Asn Lys Asn
        135                 140                 145 acg acc tac gtg acc aac act ctc tgg cct atc atc aag ctc gac ctc      690
Thr Thr Tyr Val Thr Asn Thr Leu Trp Pro Ile Ile Lys Leu Asp Leu
150                 155                 160                 165 gac tac gtc gcc agc aac tgg aac cag tcc ac  gtatgttctc taaattctct    742
Asp Tyr Val Ala Ser Asn Trp Asn Gln Ser Thr
                170                 175 cccgtgggta accagtctga acgttcatag g ttt gat ctc tgg gag gag att       794
                                  Phe Asp Leu Trp Glu Glu Ile
                                                      180 aac tcg tcg ttc ttc act acc gcc gtc cag cac cgt gct ctg cgc          842
Asn Ser Ser Phe Phe Thr Thr Ala Val Gln His Arg Ala Leu Arg
        185                 190                 195 gag ggc gcg act ttc gct aat cgc atc gga caa acc tcg gtg gtc agc      890
Glu Gly Ala Thr Phe Ala Asn Arg Ile Gly Gln Thr Ser Val Val Ser
200                 205                 210                 215 ggg tac acc acc caa gca aac aac ctt ctc tgc ttc ctg cag                932
Gly Tyr Thr Thr Gln Ala Asn Asn Leu Leu Cys Phe Leu Gln
                220                 225 gcagtctatc ccgtcacacg tctgtctgtt ccgttttcc cacagctcac ctcgtcccgg     992 gccctgtag tcg tac tgg aac ccc acc ggc ggc tat atc acc gca aac acg    1043
          Ser Tyr Trp Asn Pro Thr Gly Gly Tyr Ile Thr Ala Asn Thr
          230                 235                 240 ggc ggc ggc cgc tct ggc aag gac gcg aac acc gtt ctc acg tcg atc      1091
Gly Gly Gly Arg Ser Gly Lys Asp Ala Asn Thr Val Leu Thr Ser Ile
245                 250                 255 cac acc ttc gac ccg gcc gct gga tgc gac gct gtt acg ttc cag ccg      1139
His Thr Phe Asp Pro Ala Ala Gly Cys Asp Ala Val Thr Phe Gln Pro
260                 265                 270                 275
```

```
tgc tcg gac aag gcg ctg tcg aac ttg aag gtg tac gtc gat gcg ttc      1187
Cys Ser Asp Lys Ala Leu Ser Asn Leu Lys Val Tyr Val Asp Ala Phe
            280                 285                 290 cgc tcg atc tac tcc atc aac agc ggg atc gcc tcg aat gcg gcc gtt      1235
Arg Ser Ile Tyr Ser Ile Asn Ser Gly Ile Ala Ser Asn Ala Ala Val
            295                 300                 305 gct acc ggc cgc tac ccc gag gac agc tac atg ggc gga aac                1277
Ala Thr Gly Arg Tyr Pro Glu Asp Ser Tyr Met Gly Gly Asn
            310                 315                 320 gtgagcgacc atttctgtgc gtacaccgcg gtcgcgttaa ctgagatgtt ctcctctcct     1337 gtag cca tgg tac ctc acc acc tcc gcc gtc gct gag cag ctc tac gat     1386
     Pro Trp Tyr Leu Thr Thr Ser Ala Val Ala Glu Gln Leu Tyr Asp
                     325                 330                 335 gcg ctc att gtg tgg aac aag ctt ggc gcc ctg aac gtc acg agc acc      1434
Ala Leu Ile Val Trp Asn Lys Leu Gly Ala Leu Asn Val Thr Ser Thr
            340                 345                 350 tcc ctc ccc ttc ttc cag cag ttc tcg tca ggc gtc acc gtc ggc acc      1482
Ser Leu Pro Phe Phe Gln Gln Phe Ser Ser Gly Val Thr Val Gly Thr
            355                 360                 365 tat gcc tca tcc tcg tcc acc ttc aag acg ctc act tcc gcc atc aag      1530
Tyr Ala Ser Ser Ser Ser Thr Phe Lys Thr Leu Thr Ser Ala Ile Lys
            370                 375                 380 acc ttc gcc gac ggc ttc ctc gcg gtc aac gcc aag tac acg ccc tcg      1578
Thr Phe Ala Asp Gly Phe Leu Ala Val Asn Ala Lys Tyr Thr Pro Ser
385                 390                 395                 400 aac ggc ggc ctt gct gaa cag tac agc cgg agc aac ggc tcg ccc gtc      1626
Asn Gly Gly Leu Ala Glu Gln Tyr Ser Arg Ser Asn Gly Ser Pro Val
            405                 410                 415 agc gct gtg gac ctg acg tgg agc tat gct gct gcc ctc acg tcg ttt      1674
Ser Ala Val Asp Leu Thr Trp Ser Tyr Ala Ala Ala Leu Thr Ser Phe
            420                 425                 430 gct gcg cgc tca ggc aag acg tat gcg agc tgg ggc gcg gcg ggt ttg      1722
Ala Ala Arg Ser Gly Lys Thr Tyr Ala Ser Trp Gly Ala Ala Gly Leu
            435                 440                 445 act gtc ccg acg act tgc tcg ggg agt ggc ggt gct ggg act gtg gcc      1770
Thr Val Pro Thr Thr Cys Ser Gly Ser Gly Gly Ala Gly Thr Val Ala
            450                 455                 460 gtc acc ttc aac gtg cag gcg acc acc gtg ttc ggc g gtgagtacgc         1817
Val Thr Phe Asn Val Gln Ala Thr Thr Val Phe Gly
465                 470                 475 catcgtatgc tactagggca gttactcata gcttgtcgga cttgtag ag  aac att      1872
                                                     Glu Asn Ile tac atc aca ggc tcg gtc ccc gct ctc cag aac tgg tcg ccc gac aac      1920
Tyr Ile Thr Gly Ser Val Pro Ala Leu Gln Asn Trp Ser Pro Asp Asn
480                 485                 490                 495 gcg ctc atc ctc tca gcg gcc aac tac ccc act tgg agc agt a            1963
Ala Leu Ile Leu Ser Ala Ala Asn Tyr Pro Thr Trp Ser Ser
            500                 505 cgtctgaacc gccttcagcc tgcttcatac gttcgctgac atcgggcatc catctagtca    2023 cc  gtg aac ctg ccg gcg agc acg acg atc gag tac aag tac att cgc      2070
Thr Val Asn Leu Pro Ala Ser Thr Thr Ile Glu Tyr Lys Tyr Ile Arg
            515                 520                 525 aag ttc aac ggc gcg gtc acc tgg gag tcc gac ccg aac aac tcg atc      2118
Lys Phe Asn Gly Ala Val Thr Trp Glu Ser Asp Pro Asn Asn Ser Ile
            530                 535                 540 acg acg ccc gcg agc ggc acg ttc acc cag aac gac acc tgg cgg tag      2166
Thr Thr Pro Ala Ser Gly Thr Phe Thr Gln Asn Asp Thr Trp Arg
            545                 550                 555
```

<210> SEQ ID NO 2
<211> LENGTH: 574
<212> TYPE: PRT
<213> ORGANISM: Trametes cingulata

<400> SEQUENCE: 2

Met Arg Phe Thr Leu Leu Thr Ser Leu Leu Gly Leu Ala Leu Gly Ala
            -15                 -10                  -5

Phe Ala Gln Ser Ser Ala Ala Asp Ala Tyr Val Ala Ser Glu Ser Pro
     -1   1               5                  10

Ile Ala Lys Ala Gly Val Leu Ala Asn Ile Gly Pro Ser Gly Ser Lys
 15               20                  25                  30

Ser Asn Gly Ala Lys Ala Gly Ile Val Ile Ala Ser Pro Ser Thr Ser
                 35                  40                  45

Asn Pro Asn Tyr Leu Tyr Thr Trp Thr Arg Asp Ser Ser Leu Val Phe
             50                  55                  60

Lys Ala Leu Ile Asp Gln Phe Thr Thr Gly Glu Asp Thr Ser Leu Arg
             65                  70                  75

Thr Leu Ile Asp Glu Phe Thr Ser Ala Glu Ala Ile Leu Gln Gln Val
 80                  85                  90

Pro Asn Pro Ser Gly Thr Val Ser Thr Gly Gly Leu Gly Glu Pro Lys
 95                  100                 105                 110

Phe Asn Ile Asp Glu Thr Ala Phe Thr Asp Ala Trp Gly Arg Pro Gln
                 115                 120                 125

Arg Asp Gly Pro Ala Leu Arg Ala Thr Ala Ile Ile Thr Tyr Ala Asn
             130                 135                 140

Trp Leu Leu Asp Asn Lys Asn Thr Thr Tyr Val Thr Asn Thr Leu Trp
             145                 150                 155

Pro Ile Ile Lys Leu Asp Leu Asp Tyr Val Ala Ser Asn Trp Asn Gln
 160                 165                 170

Ser Thr Phe Asp Leu Trp Glu Glu Ile Asn Ser Ser Phe Phe Thr
 175                 180                 185                 190

Thr Ala Val Gln His Arg Ala Leu Arg Glu Gly Ala Thr Phe Ala Asn
                 195                 200                 205

Arg Ile Gly Gln Thr Ser Val Val Ser Gly Tyr Thr Thr Gln Ala Asn
             210                 215                 220

Asn Leu Leu Cys Phe Leu Gln Ser Tyr Trp Asn Pro Thr Gly Gly Tyr
             225                 230                 235

Ile Thr Ala Asn Thr Gly Gly Gly Arg Ser Gly Lys Asp Ala Asn Thr
 240                 245                 250

Val Leu Thr Ser Ile His Thr Phe Asp Pro Ala Ala Gly Cys Asp Ala
 255                 260                 265                 270

Val Thr Phe Gln Pro Cys Ser Asp Lys Ala Leu Ser Asn Leu Lys Val
                 275                 280                 285

Tyr Val Asp Ala Phe Arg Ser Ile Tyr Ser Ile Asn Ser Gly Ile Ala
                 290                 295                 300

Ser Asn Ala Ala Val Ala Thr Gly Arg Tyr Pro Glu Asp Ser Tyr Met
             305                 310                 315

Gly Gly Asn Pro Trp Tyr Leu Thr Thr Ser Ala Val Ala Glu Gln Leu
 320                 325                 330

Tyr Asp Ala Leu Ile Val Trp Asn Lys Leu Gly Ala Leu Asn Val Thr
 335                 340                 345                 350

Ser Thr Ser Leu Pro Phe Phe Gln Gln Phe Ser Ser Gly Val Thr Val
                 355                 360                 365

```
Gly Thr Tyr Ala Ser Ser Ser Thr Phe Lys Thr Leu Thr Ser Ala
                370                 375                 380

Ile Lys Thr Phe Ala Asp Gly Phe Leu Ala Val Asn Ala Lys Tyr Thr
            385                 390                 395

Pro Ser Asn Gly Gly Leu Ala Glu Gln Tyr Ser Arg Ser Asn Gly Ser
    400                 405                 410

Pro Val Ser Ala Val Asp Leu Thr Trp Ser Tyr Ala Ala Ala Leu Thr
415                 420                 425                 430

Ser Phe Ala Ala Arg Ser Gly Lys Thr Tyr Ala Ser Trp Gly Ala Ala
                435                 440                 445

Gly Leu Thr Val Pro Thr Thr Cys Ser Gly Ser Gly Ala Gly Thr
                450                 455                 460

Val Ala Val Thr Phe Asn Val Gln Ala Thr Thr Val Phe Gly Glu Asn
                465                 470                 475

Ile Tyr Ile Thr Gly Ser Val Pro Ala Leu Gln Asn Trp Ser Pro Asp
            480                 485                 490

Asn Ala Leu Ile Leu Ser Ala Ala Asn Tyr Pro Thr Trp Ser Ser Thr
495                 500                 505                 510

Val Asn Leu Pro Ala Ser Thr Thr Ile Glu Tyr Lys Tyr Ile Arg Lys
                515                 520                 525

Phe Asn Gly Ala Val Thr Trp Glu Ser Asp Pro Asn Asn Ser Ile Thr
                530                 535                 540

Thr Pro Ala Ser Gly Thr Phe Thr Gln Asn Asp Thr Trp Arg
                545                 550                 555

<210> SEQ ID NO 3
<211> LENGTH: 1725
<212> TYPE: DNA
<213> ORGANISM: Trametes cingulata
<220> FEATURE:
<221> NAME/KEY: misc_feature
<222> LOCATION: (1)..(1725)
<223> OTHER INFORMATION: cDNA
<220> FEATURE:
<221> NAME/KEY: misc_feature
<222> LOCATION: (55)..(1725)
<223> OTHER INFORMATION: coding region of cDNA
<220> FEATURE:
<221> NAME/KEY: misc_feature
<222> LOCATION: (1420)..(1725)
<223> OTHER INFORMATION: binding domain

<400> SEQUENCE: 3
atgcgtttca cgctcctcac ctccctcctg ggcctcgccc tcggcgcgtt cgcgcagtcg      60
agtgcggccg acgcgtacgt cgcgtccgaa tcgcccatcg ccaaggcggg tgtgctcgcc     120
aacatcgggc ccagcggctc caagtccaac ggagcaaagg caggcatcgt gattgcaagt     180
ccgagcacat ccaacccgaa ctacctgtac acatggacgc gcgactcgtc cctcgtgttc     240
aaggcgctca tcgaccagtt caccactggc gaagatacct cgctccgaac tctgattgac     300
gagttcacct cggcggaggc catactccag caggtgccga cccgagcgg acagtcagc      360 actggaggcc tcggcgagcc caagttcaac atcgacgaga ccgcgttcac ggatgcctgg     420
ggtcgtcctc agcgcgatgg tcccgctctc cgggcgactg ccatcatcac ctacgccaac     480
tggctcctcg acaacaagaa cacgacctac gtgaccaaca ctctctggcc tatcatcaag     540
ctcgacctcg actacgtcgc cagcaactgg aaccagtcca cgtttgatct ctgggaggag     600
attaactcct cgtcgttctt cactaccgcc gtccagcacc gtgctctgcg cgagggcgcg     660
actttcgcta atcgcatcgg acaaacctcg gtggtcagcg ggtacaccac ccaagcaaac     720
```

```
aaccttctct gcttcctgca gtcgtactgg aaccccaccg gcggctatat caccgcaaac    780
acgggcggcg gccgctctgg caaggacgcg aacaccgttc tcacgtcgat ccacaccttc    840
gacccggccg ctggatgcga cgctgttacg ttccagccgt gctcggacaa ggcgctgtcg    900
aacttgaagg tgtacgtcga tgcgttccgc tcgatctact ccatcaacag cgggatcgcc    960
tcgaatgcgg ccgttgctac cggccgctac cccgaggaca gctacatggg cggaaaccca    1020
tggtacctca ccacctccgc cgtcgctgag cagctctacg atgcgctcat tgtgtggaac    1080
aagcttggcg ccctgaacgt cacgagcacc tccctcccct tcttccagca gttctcgtca    1140
ggcgtcaccg tcggcaccta tgcctcatcc tcgtccacct tcaagacgct cacttccgcc    1200
atcaagacct tcgccgacgg cttcctcgcg gtcaacgcca agtacacgcc ctcgaacggc    1260
ggccttgctg aacagtacag ccggagcaac ggctcgcccg tcagcgctgt ggacctgacg    1320
tggagctatg ctgctgccct cacgtcgttt gctgcgcgct caggcaagac gtatgcgagc    1380
tggggcgcgg cgggtttgac tgtcccgacg acttgctcgg ggagtggcgg tgctgggact    1440
gtggccgtca ccttcaacgt gcaggcgacc accgtgttcg gcgagaacat ttacatcaca    1500
ggctcggtcc ccgctctcca gaactggtcg cccgacaacg cgctcatcct ctcagcggcc    1560
aactacccca cttggagcag taccgtgaac ctgccggcga gcacgacgat cgagtacaag    1620
tacattcgca agttcaacgg cgcggtcacc tgggagtccg acccgaacaa ctcgatcacg    1680
acgcccgcga gcggcacgtt cacccagaac gacacctggc ggtag                    1725

<210> SEQ ID NO 4
<211> LENGTH: 2189
<212> TYPE: DNA
<213> ORGANISM: Pachykytospora papyracea
<220> FEATURE:
<221> NAME/KEY: CDS
<222> LOCATION: (1)..(159)
<220> FEATURE:
<221> NAME/KEY: sig_peptide
<222> LOCATION: (1)..(54)
<220> FEATURE:
<221> NAME/KEY: mat_peptide
<222> LOCATION: (55)..(2186)
<220> FEATURE:
<221> NAME/KEY: Intron
<222> LOCATION: (160)..(238)
<220> FEATURE:
<221> NAME/KEY: CDS
<222> LOCATION: (239)..(720)
<220> FEATURE:
<221> NAME/KEY: Intron
<222> LOCATION: (516)..(572)
<220> FEATURE:
<221> NAME/KEY: Intron
<222> LOCATION: (721)..(782)
<220> FEATURE:
<221> NAME/KEY: CDS
<222> LOCATION: (783)..(942)
<220> FEATURE:
<221> NAME/KEY: Intron
<222> LOCATION: (943)..(1005)
<220> FEATURE:
<221> NAME/KEY: CDS
<222> LOCATION: (1006)..(1281)
<220> FEATURE:
<221> NAME/KEY: Intron
<222> LOCATION: (1282)..(1340)
<220> FEATURE:
<221> NAME/KEY: CDS
<222> LOCATION: (1341)..(1803)
<220> FEATURE:
<221> NAME/KEY: misc_feature
<222> LOCATION: (1743)..(1769)
<223> OTHER INFORMATION: linker
<220> FEATURE:
```

<221> NAME/KEY: misc_feature
<222> LOCATION: (1770)..(2189)
<223> OTHER INFORMATION: binding region
<220> FEATURE:
<221> NAME/KEY: Intron
<222> LOCATION: (1804)..(1882)
<220> FEATURE:
<221> NAME/KEY: CDS
<222> LOCATION: (1883)..(1978)
<220> FEATURE:
<221> NAME/KEY: Intron
<222> LOCATION: (1979)..(2043)
<220> FEATURE:
<221> NAME/KEY: CDS
<222> LOCATION: (2044)..(2186)

<400> SEQUENCE: 4

```
atg cgc ttc acc ctc ctc tcc tcc ctc gtc gcc ctc gcc acc ggc gcg        48
Met Arg Phe Thr Leu Leu Ser Ser Leu Val Ala Leu Ala Thr Gly Ala
    -15                 -10                 -5 ttc gcc cag acc agc cag gcc gac gcg tac gtc aag tcc gag ggc ccc        96
Phe Ala Gln Thr Ser Gln Ala Asp Ala Tyr Val Lys Ser Glu Gly Pro
     -1   1               5                  10 atc gcg aag gcg ggc ctc ctc gcc aac atc ggg ccc agc ggc tcc aag       144
Ile Ala Lys Ala Gly Leu Leu Ala Asn Ile Gly Pro Ser Gly Ser Lys
 15                  20                  25                  30 tcg cac ggg gcg aag gtgcgcttct cttttcccca ttctacgtcg cttaaagcgc       199
Ser His Gly Ala Lys
                 35 gctcatacat gtgcatgacc gcgttccgcg tgcgcgcag gcc ggt ctc gtc gtc        253
                                           Ala Gly Leu Val Val
                                                            40 gcc tcc ccc agc acg tcg gac ccc gac tac gtc tac acc tgg acg cgt       301
Ala Ser Pro Ser Thr Ser Asp Pro Asp Tyr Val Tyr Thr Trp Thr Arg
                45                  50                  55 gat tcg tca ctc gtc ttc aag act atc atc gac cag ttc acc tcc ggg       349
Asp Ser Ser Leu Val Phe Lys Thr Ile Ile Asp Gln Phe Thr Ser Gly
             60                  65                  70 gaa gac acc tcc ctc cgc aca ctc att gac cag ttc act agc gcg gag       397
Glu Asp Thr Ser Leu Arg Thr Leu Ile Asp Gln Phe Thr Ser Ala Glu
         75                  80                  85 aag gac ctc cag cag acg tcc aac cct agt ggc act gtt tcc acc ggc       445
Lys Asp Leu Gln Gln Thr Ser Asn Pro Ser Gly Thr Val Ser Thr Gly
     90                  95                 100 ggt ctc ggc gag ccc aag ttc aac atc gat ggg tcc gcg ttc acc ggt       493
Gly Leu Gly Glu Pro Lys Phe Asn Ile Asp Gly Ser Ala Phe Thr Gly
105                 110                 115                 120 gcc tgg ggt cgc cct cag cgc ggt atg cac act cta cca cag ttg aag       541
Ala Trp Gly Arg Pro Gln Arg Gly Met His Thr Leu Pro Gln Leu Lys
                125                 130                 135 ctt gtt aag cgc tta cat gtt ttg tgc aca gac ggt cct gct ctc cgc       589
Leu Val Lys Arg Leu His Val Leu Cys Thr Asp Gly Pro Ala Leu Arg
            140                 145                 150 gcg act gct atc ata gcc tac gct aac tgg ctg ctc gac aac aac aac       637
Ala Thr Ala Ile Ile Ala Tyr Ala Asn Trp Leu Leu Asp Asn Asn Asn
        155                 160                 165 ggc acg tcc tac gtc acc aac acc ctc tgg ccc atc atc aag ctt gac       685
Gly Thr Ser Tyr Val Thr Asn Thr Leu Trp Pro Ile Ile Lys Leu Asp
    170                 175                 180 ttg gac tac acc cag aac aac tgg aac cag tcg ac  gtaagttcat            730
Leu Asp Tyr Thr Gln Asn Asn Trp Asn Gln Ser Thr
185                 190                 195 tattccagct ttggctgcta gaactgcatt gatcctcatg tcttatgccc ag g ttc       786
                                                          Phe
```

```
gac ctt tgg gag gag gtc aac tcc tcc tct ttc ttc acg act gcc gtc         834
Asp Leu Trp Glu Glu Val Asn Ser Ser Ser Phe Phe Thr Thr Ala Val
        200                 205                 210 cag cac cgt gct ctc cgc gag ggt atc gcc ttc gcg aag aag atc ggc         882
Gln His Arg Ala Leu Arg Glu Gly Ile Ala Phe Ala Lys Lys Ile Gly
    215                 220                 225 caa acg tcg gtc gtg agc ggc tac acc acg cag gcg acc aac ctt ctc         930
Gln Thr Ser Val Val Ser Gly Tyr Thr Thr Gln Ala Thr Asn Leu Leu
230                 235                 240                 245 tgc ttc ctg cag gtcagtgtgc atgtgcagca cgccttatgg ctatagctta            982
Cys Phe Leu Gln acccgtgttc cgcatcttcg cag tcg tac tgg aac ccc tcg ggc ggc tat gtc     1035
                        Ser Tyr Trp Asn Pro Ser Gly Gly Tyr Val
                                250                 255 act gcg aac aca ggc ggc ggc cgg tcc ggc aag gac tcg aac acc gtc       1083
Thr Ala Asn Thr Gly Gly Gly Arg Ser Gly Lys Asp Ser Asn Thr Val
260                 265                 270                 275 ctg acc tcg atc cac acc ttc gac ccc gcc gct ggc tgc gac gcc gcg       1131
Leu Thr Ser Ile His Thr Phe Asp Pro Ala Ala Gly Cys Asp Ala Ala
            280                 285                 290 acg ttc cag ccg tgc tct gac aag gcc ctg tcc aac ctc aag gtc tac       1179
Thr Phe Gln Pro Cys Ser Asp Lys Ala Leu Ser Asn Leu Lys Val Tyr
        295                 300                 305 gtc gac tcg ttc cgt tcc atc tac tcc atc aac agt ggc atc gcc tcc       1227
Val Asp Ser Phe Arg Ser Ile Tyr Ser Ile Asn Ser Gly Ile Ala Ser
    310                 315                 320 aac gcc gct gtc gct gtt ggc cgc tac ccc gag gat gtg tac tac aac       1275
Asn Ala Ala Val Ala Val Gly Arg Tyr Pro Glu Asp Val Tyr Tyr Asn
325                 330                 335 ggc aac gtgagttccg tgtcccctgc atcattgtca acagcagaaa ctgaatccca       1331
Gly Asn
340 tccgcgtag ccc tgg tac ctc tcc acg tcc gcc gtc gct gag cag ctc tac    1382
          Pro Trp Tyr Leu Ser Thr Ser Ala Val Ala Glu Gln Leu Tyr
                  345                 350                 355 gac gcg atc atc gtc tgg aac aag ctc ggc tcg ctc gaa gtg acg agc       1430
Asp Ala Ile Ile Val Trp Asn Lys Leu Gly Ser Leu Glu Val Thr Ser
                360                 365                 370 acc tcg ctc gcg ttc ttc aag cag ctc tcc tcg gac gcc gcc gtc ggc       1478
Thr Ser Leu Ala Phe Phe Lys Gln Leu Ser Ser Asp Ala Ala Val Gly
            375                 380                 385 acc tac tcg tcc tcg tcc gcg acg ttc aag acg ctc act gca gcc gcg       1526
Thr Tyr Ser Ser Ser Ser Ala Thr Phe Lys Thr Leu Thr Ala Ala Ala
        390                 395                 400 aag aca ctc gcg gat ggc ttc ctc gct gtg aac gcg aag tac acg ccc       1574
Lys Thr Leu Ala Asp Gly Phe Leu Ala Val Asn Ala Lys Tyr Thr Pro
    405                 410                 415 tcg aac ggc ggc ctc gcg gag cag ttc agc aag agc aac ggc tcg ccg       1622
Ser Asn Gly Gly Leu Ala Glu Gln Phe Ser Lys Ser Asn Gly Ser Pro
420                 425                 430                 435 ctc agc gcc gtc gac ctc acg tgg agc tac gcc gcc gcg ctc acg tcc       1670
Leu Ser Ala Val Asp Leu Thr Trp Ser Tyr Ala Ala Ala Leu Thr Ser
            440                 445                 450 ttt gcc gcg cgt gag ggc aag acc ccc gcg agc tgg ggc gct gcg ggc       1718
Phe Ala Ala Arg Glu Gly Lys Thr Pro Ala Ser Trp Gly Ala Ala Gly
        455                 460                 465 ctc acc gtg ccg tcg acg tgc tcg ggt aac gcg ggc ccc agc gtg aag       1766
Leu Thr Val Pro Ser Thr Cys Ser Gly Asn Ala Gly Pro Ser Val Lys
    470                 475                 480
```

```
gtg acg ttc aac gtc cag gct acg act acc ttc ggc g gtcagtcctc    1813
Val Thr Phe Asn Val Gln Ala Thr Thr Thr Phe Gly
    485                 490                 495 ttctccaact cgtttcggtc ggtgatgttg agcattcgtc tgacgtgtgt gtgttactgc    1873 tgcttgcag ag  aac atc tac atc acc ggt aac acc gct gcg ctc cag aac    1923
              Glu Asn Ile Tyr Ile Thr Gly Asn Thr Ala Ala Leu Gln Asn
                  500                 505 tgg tcg ccc gat aac gcg ctc ctc tct gct gac aag tac ccc acc    1971
Trp Ser Pro Asp Asn Ala Leu Leu Ser Ala Asp Lys Tyr Pro Thr
510                 515                 520                 525 tgg agc a gtacgtgtca tctcatctcc agcctctcat attacgttgt ttgctcatct    2028
Trp Ser gcatgtgctt cgcag tc  acg ctc gac ctc ccc gcg aac acc gtc gtc gag    2078
                    Ile Thr Leu Asp Leu Pro Ala Asn Thr Val Val Glu
                        530                 535 tac aaa tac atc cgc aag ttc aac ggc cag gtc acc tgg gaa tcg gac    2126
Tyr Lys Tyr Ile Arg Lys Phe Asn Gly Gln Val Thr Trp Glu Ser Asp
540                 545                 550                 555 ccc aac aac tcg atc acg acg ccc gcc gac ggt acc ttc acc cag aac    2174
Pro Asn Asn Ser Ile Thr Thr Pro Ala Asp Gly Thr Phe Thr Gln Asn
                560                 565                 570 gac acc tgg cgg tga                                                2189
Asp Thr Trp Arg
        575

<210> SEQ ID NO 5
<211> LENGTH: 593
<212> TYPE: PRT
<213> ORGANISM: Pachykytospora papyracea

<400> SEQUENCE: 5

Met Arg Phe Thr Leu Leu Ser Ser Leu Val Ala Leu Ala Thr Gly Ala
            -15                 -10                  -5

Phe Ala Gln Thr Ser Gln Ala Asp Ala Tyr Val Lys Ser Glu Gly Pro
 -1  1               5                  10

Ile Ala Lys Ala Gly Leu Leu Ala Asn Ile Gly Pro Ser Gly Ser Lys
15                  20                  25                  30

Ser His Gly Ala Lys Ala Gly Leu Val Val Ala Ser Pro Ser Thr Ser
                35                  40                  45

Asp Pro Asp Tyr Val Tyr Thr Trp Thr Arg Asp Ser Ser Leu Val Phe
            50                  55                  60

Lys Thr Ile Ile Asp Gln Phe Thr Ser Gly Glu Asp Thr Ser Leu Arg
65                  70                  75

Thr Leu Ile Asp Gln Phe Thr Ser Ala Glu Lys Asp Leu Gln Gln Thr
            80                  85                  90

Ser Asn Pro Ser Gly Thr Val Ser Thr Gly Gly Leu Gly Glu Pro Lys
95                  100                 105                 110

Phe Asn Ile Asp Gly Ser Ala Phe Thr Gly Ala Trp Gly Arg Pro Gln
                115                 120                 125

Arg Gly Met His Thr Leu Pro Gln Leu Lys Leu Val Lys Arg Leu His
            130                 135                 140

Val Leu Cys Thr Asp Gly Pro Ala Leu Arg Ala Thr Ala Ile Ile Ala
            145                 150                 155

Tyr Ala Asn Trp Leu Leu Asp Asn Asn Gly Thr Ser Tyr Val Thr
            160                 165                 170

Asn Thr Leu Trp Pro Ile Ile Lys Leu Asp Leu Asp Tyr Thr Gln Asn
175                 180                 185                 190
```

Asn Trp Asn Gln Ser Thr Phe Asp Leu Trp Glu Glu Val Asn Ser Ser
              195                 200                 205

Ser Phe Phe Thr Thr Ala Val Gln His Arg Ala Leu Arg Glu Gly Ile
            210                 215                 220

Ala Phe Ala Lys Lys Ile Gly Gln Thr Ser Val Val Ser Gly Tyr Thr
            225                 230                 235

Thr Gln Ala Thr Asn Leu Leu Cys Phe Leu Gln Ser Tyr Trp Asn Pro
        240                 245                 250

Ser Gly Gly Tyr Val Thr Ala Asn Thr Gly Gly Arg Ser Gly Lys
255                 260                 265                 270

Asp Ser Asn Thr Val Leu Thr Ser Ile His Thr Phe Asp Pro Ala Ala
                275                 280                 285

Gly Cys Asp Ala Ala Thr Phe Gln Pro Cys Ser Asp Lys Ala Leu Ser
        290                 295                 300

Asn Leu Lys Val Tyr Val Asp Ser Phe Arg Ser Ile Tyr Ser Ile Asn
        305                 310                 315

Ser Gly Ile Ala Ser Asn Ala Ala Val Ala Val Gly Arg Tyr Pro Glu
        320                 325                 330

Asp Val Tyr Tyr Asn Gly Asn Pro Trp Tyr Leu Ser Thr Ser Ala Val
335                 340                 345                 350

Ala Glu Gln Leu Tyr Asp Ala Ile Ile Val Trp Asn Lys Leu Gly Ser
                355                 360                 365

Leu Glu Val Thr Ser Thr Ser Leu Ala Phe Phe Lys Gln Leu Ser Ser
                370                 375                 380

Asp Ala Ala Val Gly Thr Tyr Ser Ser Ser Ala Thr Phe Lys Thr
        385                 390                 395

Leu Thr Ala Ala Ala Lys Thr Leu Ala Asp Gly Phe Leu Ala Val Asn
        400                 405                 410

Ala Lys Tyr Thr Pro Ser Asn Gly Gly Leu Ala Glu Gln Phe Ser Lys
415                 420                 425                 430

Ser Asn Gly Ser Pro Leu Ser Ala Val Asp Leu Thr Trp Ser Tyr Ala
                435                 440                 445

Ala Ala Leu Thr Ser Phe Ala Ala Arg Glu Gly Lys Thr Pro Ala Ser
            450                 455                 460

Trp Gly Ala Ala Gly Leu Thr Val Pro Ser Thr Cys Ser Gly Asn Ala
            465                 470                 475

Gly Pro Ser Val Lys Val Thr Phe Asn Val Gln Ala Thr Thr Thr Phe
480                 485                 490

Gly Glu Asn Ile Tyr Ile Thr Gly Asn Thr Ala Ala Leu Gln Asn Trp
495                 500                 505                 510

Ser Pro Asp Asn Ala Leu Leu Leu Ser Ala Asp Lys Tyr Pro Thr Trp
                515                 520                 525

Ser Ile Thr Leu Asp Leu Pro Ala Asn Thr Val Val Glu Tyr Lys Tyr
            530                 535                 540

Ile Arg Lys Phe Asn Gly Gln Val Thr Trp Glu Ser Asp Pro Asn Asn
            545                 550                 555

Ser Ile Thr Thr Pro Ala Asp Gly Thr Phe Thr Gln Asn Asp Thr Trp
        560                 565                 570

Arg
575

<210> SEQ ID NO 6
<211> LENGTH: 1725
<212> TYPE: DNA
<213> ORGANISM: Pachykytospora papyracea
<220> FEATURE:
<221> NAME/KEY: misc_feature
<222> LOCATION: (1)..(1725)
<223> OTHER INFORMATION: cDNA
<220> FEATURE:
<221> NAME/KEY: misc_feature
<222> LOCATION: (55)..(1725)
<223> OTHER INFORMATION: coding region of cDNA
<220> FEATURE:
<221> NAME/KEY: misc_feature
<222> LOCATION: (1423)..(1725)
<223> OTHER INFORMATION: binding domain

<400> SEQUENCE: 6

```
atgcgcttca cccctcctctc ctccctcgtc gccctcgcca ccggcgcgtt cgcccagacc      60
agccaggccg acgcgtacgt caagtccgag ggccccatcg cgaaggcggg cctcctcgcc     120
aacatcgggc ccagcggctc caagtcgcac ggggcgaagg ccgtctcgt cgtcgcctcc      180
cccagcacgt cggaccccga ctacgtctac acctggacgc gtgattcgtc actcgtcttc     240
aagactatca tcgaccagtt cacctccggg aagacacct cccctccgcac actcattgac     300
cagttcacta gcgcggagaa ggacctccag cagacgtcca accctagtgg cactgttttcc    360
accggcggtc tcggcgagcc caagttcaac atcgatgggt ccgcgttcac cggtgcctgg    420
ggtcgccctc agcgcgacgg tcctgctctc cgcgcgactg ctatcatagc ctacgctaac    480
tggctgctcg acaacaacaa cggcacgtcc tacgtcacca cacccctctg cccatcatc    540
aagcttgact tggactacac ccagaacaac tggaaccagt cgacgttcga cctttgggag    600
gaggtcaact cctcctcttt cttcacgact gccgtccagc accgtgctct ccgcgagggt    660
atcgccttcg cgaagaagat cggccaaacg tcggtcgtga gcggctacac cacgcaggcg    720
accaaccttc tctgcttcct gcagtcgtac tggaacccct cgggcggcta tgtcactgcg    780
aacacaggcg gcggccggtc cggcaaggac tcgaacaccg tcctgacctc gatccacacc    840
ttcgaccccg ccgctggctg cgacgccgcg acgttccagc cgtgctctga caaggccctg    900
tccaacctca aggtctacgt cgactcgttc cgttccatct actccatcaa cagtggcatc    960
gcctccaacg ccgctgtcgc tgttggccgc taccccgagg atgtgtacta caacggcaac   1020
ccctggtacc tctccacgtc cgccgtcgct gagcagctct acgacgcgat catcgtctgg   1080
aacaagctcg gctcgctcga agtgacgagc acctcgctcg cgttcttcaa gcagctctcc   1140
tcggacgccg ccgtcggcac ctactcgtcc tcgtccgcga cgttcaagac gctcactgca   1200
gccgcgaaga cactcgcgga tggcttcctc gctgtgaacg cgaagtacac gccctcgaac   1260
ggcggcctcg cggagcagtt cagcaagagc aacggctcgc cgctcagcgc cgtcgacctc   1320
acgtggagct acgccgccgc gctcacgtcc tttgccgcgc gtgagggcaa gaccccccgcg   1380
agctggggcg ctgcgggcct caccgtgccg tcgacgtgct cgggtaacgc gggccccagc   1440
gtgaaggtga cgttcaacgt ccaggctacg actaccttcg gcgagaacat ctacatcacc   1500
ggtaacaccg ctgcgctcca gaactggtcg cccgataacg cgctcctcct ctctgctgac   1560
aagtaccccca cctggagcat cacgctcgac ctccccgcga caccgtcgt cgagtacaaa   1620
tacatccgca agttcaacgg ccaggtcacc tgggaatcgg accccaacaa ctcgatcacg   1680
acgcccgccg acggtacctt cacccagaac gacacctggc ggtga                    1725
```

<210> SEQ ID NO 7
<211> LENGTH: 18
<212> TYPE: DNA
<213> ORGANISM: Artificial sequence
<220> FEATURE:
<223> OTHER INFORMATION: Degenerated Primer ArAF1

```
<220> FEATURE:
<221> NAME/KEY: misc_feature
<222> LOCATION: (2)..(2)
<223> OTHER INFORMATION: R = A or G
<220> FEATURE:
<221> NAME/KEY: misc_feature
<222> LOCATION: (4)..(4)
<223> OTHER INFORMATION: R = A or G
<220> FEATURE:
<221> NAME/KEY: misc_feature
<222> LOCATION: (7)..(7)
<223> OTHER INFORMATION: Y = C or T
<220> FEATURE:
<221> NAME/KEY: misc_feature
<222> LOCATION: (8)..(8)
<223> OTHER INFORMATION: D = A or G or T
<220> FEATURE:
<221> NAME/KEY: misc_feature
<222> LOCATION: (9)..(9)
<223> OTHER INFORMATION: V = A or C or G
<220> FEATURE:
<221> NAME/KEY: misc_feature
<222> LOCATION: (16)..(16)
<223> OTHER INFORMATION: Y = C or T

<400> SEQUENCE: 7
crtrctydvc aacatygg                                                 18

<210> SEQ ID NO 8
<211> LENGTH: 22
<212> TYPE: DNA
<213> ORGANISM: Artificial sequence
<220> FEATURE:
<223> OTHER INFORMATION: Degenerated Primer ArAF3
<220> FEATURE:
<221> NAME/KEY: misc_feature
<222> LOCATION: (7)..(7)
<223> OTHER INFORMATION: R = A or G
<220> FEATURE:
<221> NAME/KEY: misc_feature
<222> LOCATION: (10)..(10)
<223> OTHER INFORMATION: D = A or G or T
<220> FEATURE:
<221> NAME/KEY: misc_feature
<222> LOCATION: (13)..(13)
<223> OTHER INFORMATION: Y = C or T
<220> FEATURE:
<221> NAME/KEY: misc_feature
<222> LOCATION: (16)..(16)
<223> OTHER INFORMATION: R = A or G
<220> FEATURE:
<221> NAME/KEY: misc_feature
<222> LOCATION: (17)..(17)
<223> OTHER INFORMATION: R = A or G
<220> FEATURE:
<221> NAME/KEY: misc_feature
<222> LOCATION: (19)..(19)
<223> OTHER INFORMATION: S = C or G

<400> SEQUENCE: 8
gtcagarcad ggytgrrasg tg                                            22

<210> SEQ ID NO 9
<211> LENGTH: 23
<212> TYPE: DNA
<213> ORGANISM: Artificial sequence
<220> FEATURE:
<223> OTHER INFORMATION: AM2F degenerated primer
<220> FEATURE:
<221> NAME/KEY: misc_feature
<222> LOCATION: (6)..(6)
<223> OTHER INFORMATION: n is inosine
<220> FEATURE:
<221> NAME/KEY: misc_feature
<222> LOCATION: (7)..(7)
<223> OTHER INFORMATION: M = A or C
```

```
<220> FEATURE:
<221> NAME/KEY: misc_feature
<222> LOCATION: (9)..(9)
<223> OTHER INFORMATION: N = A or C or G or T
<220> FEATURE:
<221> NAME/KEY: misc_feature
<222> LOCATION: (12)..(12)
<223> OTHER INFORMATION: N = A or C or G or T
<220> FEATURE:
<221> NAME/KEY: misc_feature
<222> LOCATION: (15)..(15)
<223> OTHER INFORMATION: R = A or G
<220> FEATURE:
<221> NAME/KEY: misc_feature
<222> LOCATION: (16)..(16)
<223> OTHER INFORMATION: M = A or C
<220> FEATURE:
<221> NAME/KEY: misc_feature
<222> LOCATION: (18)..(18)
<223> OTHER INFORMATION: N = A or C or G or T
<220> FEATURE:
<221> NAME/KEY: misc_feature
<222> LOCATION: (21)..(21)
<223> OTHER INFORMATION: Y = C or T

<400> SEQUENCE: 9
tggggnmgnc ncarmgnga ygg                                           23

<210> SEQ ID NO 10
<211> LENGTH: 18
<212> TYPE: DNA
<213> ORGANISM: Artificial sequence
<220> FEATURE:
<223> OTHER INFORMATION: AM4R2 degenerated primer
<220> FEATURE:
<221> NAME/KEY: misc_feature
<222> LOCATION: (1)..(1)
<223> OTHER INFORMATION: R = A or G
<220> FEATURE:
<221> NAME/KEY: misc_feature
<222> LOCATION: (4)..(4)
<223> OTHER INFORMATION: Y = C or T
<220> FEATURE:
<221> NAME/KEY: misc_feature
<222> LOCATION: (7)..(7)
<223> OTHER INFORMATION: N = A or C or G or T
<220> FEATURE:
<221> NAME/KEY: misc_feature
<222> LOCATION: (10)..(10)
<223> OTHER INFORMATION: R = A or G
<220> FEATURE:
<221> NAME/KEY: misc_feature
<222> LOCATION: (13)..(13)
<223> OTHER INFORMATION: N = A, C, G or T
<220> FEATURE:
<221> NAME/KEY: misc_feature
<222> LOCATION: (15)..(15)
<223> OTHER INFORMATION: K = G or T
<220> FEATURE:
<221> NAME/KEY: misc_feature
<222> LOCATION: (16)..(16)
<223> OTHER INFORMATION: N = A, C, G or T

<400> SEQUENCE: 10
rtcytcnggr tanckncc                                                18

<210> SEQ ID NO 11
<211> LENGTH: 17
<212> TYPE: DNA
<213> ORGANISM: Artificial sequence
<220> FEATURE:
<223> OTHER INFORMATION: AMF3 degenerated primer
<220> FEATURE:
<221> NAME/KEY: misc_feature
<222> LOCATION: (3)..(3)
<223> OTHER INFORMATION: Y = C or T
```

```
<220> FEATURE:
<221> NAME/KEY: misc_feature
<222> LOCATION: (6)..(6)
<223> OTHER INFORMATION: Y = C or T
<220> FEATURE:
<221> NAME/KEY: misc_feature
<222> LOCATION: (7)..(7)
<223> OTHER INFORMATION: Y = C or T
<220> FEATURE:
<221> NAME/KEY: misc_feature
<222> LOCATION: (9)..(9)
<223> OTHER INFORMATION: N = A or C or G or T
<220> FEATURE:
<221> NAME/KEY: misc_feature
<222> LOCATION: (10)..(10)
<223> OTHER INFORMATION: Y = C or T
<220> FEATURE:
<221> NAME/KEY: misc_feature
<222> LOCATION: (15)..(15)
<223> OTHER INFORMATION: R = A or G

<400> SEQUENCE: 11
taygayytny gggarga                                                  17

<210> SEQ ID NO 12
<211> LENGTH: 21
<212> TYPE: DNA
<213> ORGANISM: Artificial sequence
<220> FEATURE:
<223> OTHER INFORMATION: TraF1 primer
<220> FEATURE:
<221> NAME/KEY: misc_feature
<222> LOCATION: (1)..(21)
<223> OTHER INFORMATION: TraF1 primer

<400> SEQUENCE: 12
tagtcgtact ggaaccccac c                                             21

<210> SEQ ID NO 13
<211> LENGTH: 35
<212> TYPE: DNA
<213> ORGANISM: Artificial sequence
<220> FEATURE:
<223> OTHER INFORMATION: C1 primer

<400> SEQUENCE: 13
gtacatattg tcgttagaac gcgtaatacg actca                              35

<210> SEQ ID NO 14
<211> LENGTH: 23
<212> TYPE: DNA
<213> ORGANISM: Artificial sequence
<220> FEATURE:
<223> OTHER INFORMATION: TC5' primer
<220> FEATURE:
<221> NAME/KEY: misc_feature
<222> LOCATION: (1)..(23)
<223> OTHER INFORMATION: TC5' primer

<400> SEQUENCE: 14
cgtatatgtc agcgctacca tgt                                           23

<210> SEQ ID NO 15
<211> LENGTH: 23
<212> TYPE: DNA
<213> ORGANISM: Artificial sequence
<220> FEATURE:
<223> OTHER INFORMATION: TC3' primer
<220> FEATURE:
<221> NAME/KEY: misc_feature
<222> LOCATION: (1)..(23)
<223> OTHER INFORMATION: TC3' primer
```

```
<400> SEQUENCE: 15
aaacgtgagc gaccattttc tgt                                             23

<210> SEQ ID NO 16
<211> LENGTH: 36
<212> TYPE: DNA
<213> ORGANISM: Artificial sequence
<220> FEATURE:
<223> OTHER INFORMATION: TFF primer

<400> SEQUENCE: 16
tttggatcca ccatgcgttt cacgctcctc acctcc                               36

<210> SEQ ID NO 17
<211> LENGTH: 30
<212> TYPE: DNA
<213> ORGANISM: Artificial sequence
<220> FEATURE:
<223> OTHER INFORMATION: TFR primer

<400> SEQUENCE: 17
tttctcgagc taccgccagg tgtcattctg                                      30

<210> SEQ ID NO 18
<211> LENGTH: 23
<212> TYPE: DNA
<213> ORGANISM: Artificial sequence
<220> FEATURE:
<223> OTHER INFORMATION: PP5' primer

<400> SEQUENCE: 18
cctccctgag tgagcgatgc tgc                                             23

<210> SEQ ID NO 19
<211> LENGTH: 23
<212> TYPE: DNA
<213> ORGANISM: Artificial sequence
<220> FEATURE:
<223> OTHER INFORMATION: PP3' primer

<400> SEQUENCE: 19
caactccggc ctctcctcca gcg                                             23

<210> SEQ ID NO 20
<211> LENGTH: 36
<212> TYPE: DNA
<213> ORGANISM: Artificial sequence
<220> FEATURE:
<223> OTHER INFORMATION: PPF primer

<400> SEQUENCE: 20
tttggatcca ccatgcgctt caccctcctc tcctcc                               36

<210> SEQ ID NO 21
<211> LENGTH: 30
<212> TYPE: DNA
<213> ORGANISM: Artificial sequence
<220> FEATURE:
<223> OTHER INFORMATION: PPR primer

<400> SEQUENCE: 21
tttctcgagt caccgccagg tgtcgttctg                                      30

<210> SEQ ID NO 22
<211> LENGTH: 31
```

```
<212> TYPE: PRT
<213> ORGANISM: Aspergillus kawachii
<220> FEATURE:
<221> NAME/KEY: PEPTIDE
<222> LOCATION: (1)..(31)
<223> OTHER INFORMATION: Linker

<400> SEQUENCE: 22

Thr Thr Thr Thr Thr Thr Ala Ala Ala Thr Ser Thr Ser Lys Ala Thr
1               5                   10                  15

Thr Ser Ser Ser Ser Ser Ser Ala Ala Ala Thr Thr Ser Ser Ser
            20                  25                  30

<210> SEQ ID NO 23
<211> LENGTH: 2494
<212> TYPE: DNA
<213> ORGANISM: Leucopaxillus giganteus
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: sig_peptide
<222> LOCATION: (66)..(128)
<220> FEATURE:
<221> NAME/KEY: CDS
<222> LOCATION: (66)..(319)
<220> FEATURE:
<221> NAME/KEY: mat_peptide
<222> LOCATION: (117)..(2249)
<220> FEATURE:
<221> NAME/KEY: Intron
<222> LOCATION: (320)..(375)
<220> FEATURE:
<221> NAME/KEY: CDS
<222> LOCATION: (376)..(540)
<220> FEATURE:
<221> NAME/KEY: Intron
<222> LOCATION: (541)..(591)
<220> FEATURE:
<221> NAME/KEY: CDS
<222> LOCATION: (592)..(605)
<220> FEATURE:
<221> NAME/KEY: Intron
<222> LOCATION: (606)..(664)
<220> FEATURE:
<221> NAME/KEY: CDS
<222> LOCATION: (665)..(809)
<220> FEATURE:
<221> NAME/KEY: Intron
<222> LOCATION: (810)..(863)
<220> FEATURE:
<221> NAME/KEY: CDS
<222> LOCATION: (864)..(1023)
<220> FEATURE:
<221> NAME/KEY: Intron
<222> LOCATION: (1024)..(1088)
<220> FEATURE:
<221> NAME/KEY: CDS
<222> LOCATION: (1089)..(1361)
<220> FEATURE:
<221> NAME/KEY: Intron
<222> LOCATION: (1362)..(1415)
<220> FEATURE:
<221> NAME/KEY: CDS
<222> LOCATION: (1416)..(1896)
<220> FEATURE:
<221> NAME/KEY: misc_feature
<222> LOCATION: (1821)..(1853)
<223> OTHER INFORMATION: Linker
<220> FEATURE:
<221> NAME/KEY: misc_feature
<222> LOCATION: (1854)..(2249)
```

```
<223> OTHER INFORMATION: binding domain
<220> FEATURE:
<221> NAME/KEY: Intron
<222> LOCATION: (1897)..(1954)
<220> FEATURE:
<221> NAME/KEY: CDS
<222> LOCATION: (1955)..(2014)
<220> FEATURE:
<221> NAME/KEY: Intron
<222> LOCATION: (2015)..(2106)
<220> FEATURE:
<221> NAME/KEY: CDS
<222> LOCATION: (2107)..(2249)

<400> SEQUENCE: 23
tataaagagc gtcgcttcag cgatacctnt tcttcagngc atttcgcctc tcccttctaa      60 gcagg atg cat ttc tct gtc ctc tcc gta ttt ctc gcg att agt tct gct     110
      Met His Phe Ser Val Leu Ser Val Phe Leu Ala Ile Ser Ser Ala
          -15              -10                  -5 tgg gct cag tct agc gca gtc gat gcc tat ctc gct ctc gaa tcc tcc       158
Trp Ala Gln Ser Ser Ala Val Asp Ala Tyr Leu Ala Leu Glu Ser Ser
 -1   1               5                  10 gtc gcc aag gcc ggg ttg ctc gcc aac att ggc cca tct ggt tca aag       206
Val Ala Lys Ala Gly Leu Leu Ala Asn Ile Gly Pro Ser Gly Ser Lys
 15              20                  25                  30 tct tcg ggt gcc aag tct ggg att gtc att gcg tcg cct tcg cat agc       254
Ser Ser Gly Ala Lys Ser Gly Ile Val Ile Ala Ser Pro Ser His Ser
             35                  40                  45 aac cct gac tac ctg ttc acc tgg acc cgc gat tct tcg ctt gtg ttc       302
Asn Pro Asp Tyr Leu Phe Thr Trp Thr Arg Asp Ser Ser Leu Val Phe
         50                  55                  60 cag act atc atc aac ca  gtaggtgtct tcctcttcta ggtcgctgct              349
Gln Thr Ile Ile Asn Gln
             65 tgtcgttgac acgaggacac gcccag g ttc acg ttg gga cac gac aat agt        400
                              Phe Thr Leu Gly His Asp Asn Ser
                                           70                  75 ttg agg cct gag att gac aat ttt gtt gat tcc caa agg aag atc caa       448
Leu Arg Pro Glu Ile Asp Asn Phe Val Asp Ser Gln Arg Lys Ile Gln
             80                  85                  90 caa gtc tca aac cct tcg gga act gtt agt tct ggc ggc ctt ggc gag       496
Gln Val Ser Asn Pro Ser Gly Thr Val Ser Ser Gly Gly Leu Gly Glu
         95                 100                 105 ccc aag ttc aat atc gac gaa acc gcc ttt aca ggg gca tgg gg           540
Pro Lys Phe Asn Ile Asp Glu Thr Ala Phe Thr Gly Ala Trp Gly
    110                 115                 120 gtgagtcctt cctggactgc gtcatataca taattcacag atattgtcta g g cgg        595
                                                         Arg ccc caa cga g gtaactagtc taccatgatt accgggatgc aacatcaaca             645
Pro Gln Arg
125 gttttcgcat tatttgtag at  gga cct gct ctc cga tcc acc gcg ctc att      696
                        Asp Gly Pro Ala Leu Arg Ser Thr Ala Leu Ile
                                    130                 135 acc tgg gcc aat tac ctg atc gct aac agc aac aca tcc tac gtc acc       744
Thr Trp Ala Asn Tyr Leu Ile Ala Asn Ser Asn Thr Ser Tyr Val Thr
    140                 145                 150 aac acc cta tgg ccc atc atc aaa ttg gac ctc gac tac gtc gcg tcc       792
Asn Thr Leu Trp Pro Ile Ile Lys Leu Asp Leu Asp Tyr Val Ala Ser
155                 160                 165                 170 aac tgg aac cag act gg  gtgagtcact tgactatttt cgcaactttc              839
Asn Trp Asn Gln Thr Gly
                175
```

```
ttggttcatg aaagctactc ccag t ttc gat ttg tgg gaa gaa gta tcc tct         891
                            Phe Asp Leu Trp Glu Glu Val Ser Ser
                                180                 185 tct tcc ttc ttc act act gcg gtt caa cac cgc tcc ctt cgc caa ggt         939
Ser Ser Phe Phe Thr Thr Ala Val Gln His Arg Ser Leu Arg Gln Gly
            190                 195                 200 gct tcc cta gcc act gcc att gga caa acc tct gtc gtt cct ggc tac         987
Ala Ser Leu Ala Thr Ala Ile Gly Gln Thr Ser Val Val Pro Gly Tyr
            205                 210                 215 acc acc cag gcc aac aat ata ctc tgc ttt caa cag gtggctcctt             1033
Thr Thr Gln Ala Asn Asn Ile Leu Cys Phe Gln Gln
            220                 225 tctttctttt cttacaacta gcatacacga agaacctgac actcaaattt gctag tcc       1091
                                                               Ser
                                                               230 tac tgg aac tca gct ggg tat atg act gcc aat acc gga ggc ggg cgt       1139
Tyr Trp Asn Ser Ala Gly Tyr Met Thr Ala Asn Thr Gly Gly Gly Arg
            235                 240                 245 tct ggg aaa gac gcc aac acc gtc ctc aca agt att cac aca ttc gat       1187
Ser Gly Lys Asp Ala Asn Thr Val Leu Thr Ser Ile His Thr Phe Asp
            250                 255                 260 ccc gat gcc ggc tgc gat tcc atc act ttc caa cct tgt tca gac cgt       1235
Pro Asp Ala Gly Cys Asp Ser Ile Thr Phe Gln Pro Cys Ser Asp Arg
            265                 270                 275 gcg ctc atc aac ctt gtc aca tac gtc aat gca ttc cga agc atc tac       1283
Ala Leu Ile Asn Leu Val Thr Tyr Val Asn Ala Phe Arg Ser Ile Tyr
            280                 285                 290 gct atc aac gcg ggc atc gct aat aac caa ggc gtt gcc act ggt agg       1331
Ala Ile Asn Ala Gly Ile Ala Asn Asn Gln Gly Val Ala Thr Gly Arg
295                 300                 305                 310 tat cct gaa gat ggc tac atg ggc gga aac gtatgccttg tccactcgcc         1381
Tyr Pro Glu Asp Gly Tyr Met Gly Gly Asn
            315                 320 gtccacagtc ctcgaagcct gatcgctgcc ttag cct tgg tat ctg act act tta     1436
                                      Pro Trp Tyr Leu Thr Thr Leu
                                                          325 gcc gtt tct gaa cag ctc tac tac gct ctc tcc act tgg aag aaa cat       1484
Ala Val Ser Glu Gln Leu Tyr Tyr Ala Leu Ser Thr Trp Lys Lys His
            330                 335                 340 agc tcc ctc acc att acg gcg aca tca caa cct ttt ttc gcg ctc ttc       1532
Ser Ser Leu Thr Ile Thr Ala Thr Ser Gln Pro Phe Phe Ala Leu Phe
            345                 350                 355 tcg ccg ggt gtt gct act ggc aca tat gcg tcc tct acg act acc tat       1580
Ser Pro Gly Val Ala Thr Gly Thr Tyr Ala Ser Ser Thr Thr Thr Tyr
360                 365                 370                 375 gct aca ctt act act gct att cag aat tac gcg gat agc ttc atc gct       1628
Ala Thr Leu Thr Thr Ala Ile Gln Asn Tyr Ala Asp Ser Phe Ile Ala
            380                 385                 390 gtc gtg gct aag tat acg cct gcc aat ggc gga ctg gcg gaa cag tac       1676
Val Val Ala Lys Tyr Thr Pro Ala Asn Gly Gly Leu Ala Glu Gln Tyr
            395                 400                 405 agc agg agt aac ggt ttg ccc gtt agt gcc gtt gat tta act tgg agc       1724
Ser Arg Ser Asn Gly Leu Pro Val Ser Ala Val Asp Leu Thr Trp Ser
            410                 415                 420 tat gcc gct ctc ttg acg gcg gct gat gcg cga gcg ggg cta aca ccc       1772
Tyr Ala Ala Leu Leu Thr Ala Ala Asp Ala Arg Ala Gly Leu Thr Pro
            425                 430                 435 gct gca tgg gga gca gcg ggg ttg acc gtg cca agc act tgc tct act       1820
Ala Ala Trp Gly Ala Ala Gly Leu Thr Val Pro Ser Thr Cys Ser Thr
440                 445                 450                 455
```

-continued

```
ggg ggt ggt tca aac cca ggt ggt gga ggg tcg gtc tct gtt acg ttc    1868
Gly Gly Gly Ser Asn Pro Gly Gly Gly Gly Ser Val Ser Val Thr Phe
            460                 465                 470 aat gtt caa gct aca acc acc ttt ggt g gtaggtccca ttcaacacgc        1916
Asn Val Gln Ala Thr Thr Thr Phe Gly
    475                 480 gcagattttg ctgggaaatc tcatgattgg tttgacag aa  aac att ttt ttg acc  1971
                                             Glu Asn Ile Phe Leu Thr
                                                             485 ggc tcg atc aac gag tta gct aac tgg tct cct gat aat gct c          2014
Gly Ser Ile Asn Glu Leu Ala Asn Trp Ser Pro Asp Asn Ala
            490                 495                 500 tcgccctctc tgcggccaat tatcccacct ggagcagtca gtcccagtcc atcgctccac  2074
tacaagccat caaccgctga ccatatctct ag ta  acc gtc aac gtt ccc gca    2126
                                       Leu Thr Val Asn Val Pro Ala
                                                       505 agc act acg atc caa tac aag ttt atc cgt aaa ttc aac gga gcc atc    2174
Ser Thr Thr Ile Gln Tyr Lys Phe Ile Arg Lys Phe Asn Gly Ala Ile
            510                 515                 520 acc tgg gag tcc gac ccg aat agg cag atc aca acg ccg tct tcg gga    2222
Thr Trp Glu Ser Asp Pro Asn Arg Gln Ile Thr Thr Pro Ser Ser Gly
525                 530                 535 agt ttt gtc cag aat gac tcg tgg aag tagtcggtag ataagatgtg          2269
Ser Phe Val Gln Asn Asp Ser Trp Lys
540                 545 caagatgagg tccatggctc acccaaacgt tactcatagt aaatttgata ctgaaatttg  2329
ttcagcacat gaaatcgtta ttcctcctct gacgtttagt gaagaataaa gcgagatccc  2389
gcccaggaag gtgctatagt gtagtggtta tcactcggga ttttgatgtg gtactaagta  2449
tcatacaaca ttcccgagac ccaggttcga accctggtag cacct                  2494
```

<210> SEQ ID NO 24
<211> LENGTH: 565
<212> TYPE: PRT
<213> ORGANISM: Leucopaxillus giganteus

<400> SEQUENCE: 24

```
Met His Phe Ser Val Leu Ser Val Phe Leu Ala Ile Ser Ser Ala Trp
        -15                 -10                 -5

Ala Gln Ser Ser Ala Val Asp Ala Tyr Leu Ala Leu Glu Ser Ser Val
-1  1               5                   10                  15

Ala Lys Ala Gly Leu Leu Ala Asn Ile Gly Pro Ser Gly Ser Lys Ser
                20                  25                  30

Ser Gly Ala Lys Ser Gly Ile Val Ile Ala Ser Pro Ser His Ser Asn
            35                  40                  45

Pro Asp Tyr Leu Phe Thr Trp Thr Arg Asp Ser Ser Leu Val Phe Gln
        50                  55                  60

Thr Ile Ile Asn Gln Phe Thr Leu Gly His Asp Asn Ser Leu Arg Pro
    65                  70                  75

Glu Ile Asp Asn Phe Val Asp Ser Gln Arg Lys Ile Gln Gln Val Ser
80                  85                  90                  95

Asn Pro Ser Gly Thr Val Ser Ser Gly Leu Gly Glu Pro Lys Phe
                100                 105                 110

Asn Ile Asp Glu Thr Ala Phe Thr Gly Ala Trp Gly Arg Pro Gln Arg
            115                 120                 125

Asp Gly Pro Ala Leu Arg Ser Thr Ala Leu Ile Thr Trp Ala Asn Tyr
        130                 135                 140
```

```
Leu Ile Ala Asn Ser Asn Thr Ser Tyr Val Thr Asn Thr Leu Trp Pro
    145                 150                 155
Ile Ile Lys Leu Asp Leu Asp Tyr Val Ala Ser Asn Trp Asn Gln Thr
160                 165                 170                 175
Gly Phe Asp Leu Trp Glu Glu Val Ser Ser Ser Phe Phe Thr Thr
                    180                 185                 190
Ala Val Gln His Arg Ser Leu Arg Gln Gly Ala Ser Leu Ala Thr Ala
            195                 200                 205
Ile Gly Gln Thr Ser Val Val Pro Gly Tyr Thr Thr Gln Ala Asn Asn
        210                 215                 220
Ile Leu Cys Phe Gln Gln Ser Tyr Trp Asn Ser Ala Gly Tyr Met Thr
    225                 230                 235
Ala Asn Thr Gly Gly Gly Arg Ser Gly Lys Asp Ala Asn Thr Val Leu
240                 245                 250                 255
Thr Ser Ile His Thr Phe Asp Pro Asp Ala Gly Cys Asp Ser Ile Thr
                    260                 265                 270
Phe Gln Pro Cys Ser Asp Arg Ala Leu Ile Asn Leu Val Thr Tyr Val
            275                 280                 285
Asn Ala Phe Arg Ser Ile Tyr Ala Ile Asn Ala Gly Ile Ala Asn Asn
        290                 295                 300
Gln Gly Val Ala Thr Gly Arg Tyr Pro Glu Asp Gly Tyr Met Gly Gly
    305                 310                 315
Asn Pro Trp Tyr Leu Thr Thr Leu Ala Val Ser Glu Gln Leu Tyr Tyr
320                 325                 330                 335
Ala Leu Ser Thr Trp Lys Lys His Ser Ser Leu Thr Ile Thr Ala Thr
                    340                 345                 350
Ser Gln Pro Phe Phe Ala Leu Phe Ser Pro Gly Val Ala Thr Gly Thr
            355                 360                 365
Tyr Ala Ser Ser Thr Thr Thr Tyr Ala Thr Leu Thr Thr Ala Ile Gln
        370                 375                 380
Asn Tyr Ala Asp Ser Phe Ile Ala Val Val Ala Lys Tyr Thr Pro Ala
    385                 390                 395
Asn Gly Gly Leu Ala Glu Gln Tyr Ser Arg Ser Asn Gly Leu Pro Val
400                 405                 410                 415
Ser Ala Val Asp Leu Thr Trp Ser Tyr Ala Ala Leu Leu Thr Ala Ala
                    420                 425                 430
Asp Ala Arg Ala Gly Leu Thr Pro Ala Ala Trp Gly Ala Ala Gly Leu
            435                 440                 445
Thr Val Pro Ser Thr Cys Ser Thr Gly Gly Gly Ser Asn Pro Gly Gly
        450                 455                 460
Gly Gly Ser Val Ser Val Thr Phe Asn Val Gln Ala Thr Thr Thr Phe
    465                 470                 475
Gly Glu Asn Ile Phe Leu Thr Gly Ser Ile Asn Glu Leu Ala Asn Trp
480                 485                 490                 495
Ser Pro Asp Asn Ala Leu Thr Val Asn Val Pro Ala Ser Thr Thr Ile
                    500                 505                 510
Gln Tyr Lys Phe Ile Arg Lys Phe Asn Gly Ala Ile Thr Trp Glu Ser
            515                 520                 525
Asp Pro Asn Arg Gln Ile Thr Thr Pro Ser Ser Gly Ser Phe Val Gln
        530                 535                 540
Asn Asp Ser Trp Lys
    545
```

<210> SEQ ID NO 25
<211> LENGTH: 1722
<212> TYPE: DNA
<213> ORGANISM: Leucopaxillus giganteus
<220> FEATURE:
<221> NAME/KEY: CDS
<222> LOCATION: (1)..(1719)
<223> OTHER INFORMATION: cDNA
<220> FEATURE:
<221> NAME/KEY: sig_peptide
<222> LOCATION: (1)..(51)
<220> FEATURE:
<221> NAME/KEY: misc_feature
<222> LOCATION: (1)..(1404)
<223> OTHER INFORMATION: Catalytic Domain
<220> FEATURE:
<221> NAME/KEY: mat_peptide
<222> LOCATION: (52)..(1719)
<220> FEATURE:
<221> NAME/KEY: misc_feature
<222> LOCATION: (1405)..(1437)
<223> OTHER INFORMATION: Linker
<220> FEATURE:
<221> NAME/KEY: misc_feature
<222> LOCATION: (1438)..(1719)
<223> OTHER INFORMATION: binding domain

<400> SEQUENCE: 25

```
atg cat ttc tct gtc ctc tcc gta ttt ctc gcg att agt tct gct tgg      48
Met His Phe Ser Val Leu Ser Val Phe Leu Ala Ile Ser Ser Ala Trp
        -15                 -10                 -5 gct cag tct agc gca gtc gat gcc tat ctc gct ctc gaa tcc tcc gtc      96
Ala Gln Ser Ser Ala Val Asp Ala Tyr Leu Ala Leu Glu Ser Ser Val
 -1  1               5                  10                  15 gcc aag gcc ggg ttg ctc gcc aac att ggc cca tct ggt tca aag tct     144
Ala Lys Ala Gly Leu Leu Ala Asn Ile Gly Pro Ser Gly Ser Lys Ser
                 20                  25                  30 tcg ggt gcc aag tct ggg att gtc att gcg tcg cct tcg cat agc aac     192
Ser Gly Ala Lys Ser Gly Ile Val Ile Ala Ser Pro Ser His Ser Asn
             35                  40                  45 cct gac tac ctg ttc acc tgg acc cgc gat tct tcg ctt gtg ttc cag     240
Pro Asp Tyr Leu Phe Thr Trp Thr Arg Asp Ser Ser Leu Val Phe Gln
         50                  55                  60 act atc atc aac cag ttc acg ttg gga cac gac aat agt ttg agg cct     288
Thr Ile Ile Asn Gln Phe Thr Leu Gly His Asp Asn Ser Leu Arg Pro
     65                  70                  75 gag att gac aat ttt gtt gat tcc caa agg aag atc caa caa gtc tca     336
Glu Ile Asp Asn Phe Val Asp Ser Gln Arg Lys Ile Gln Gln Val Ser
 80                  85                  90                  95 aac cct tcg gga act gtt agt tct ggc ggc ctt ggc gag ccc aag ttc     384
Asn Pro Ser Gly Thr Val Ser Ser Gly Gly Leu Gly Glu Pro Lys Phe
                100                 105                 110 aat atc gac gaa acc gcc ttt aca ggg gca tgg ggg gat gga cct gct     432
Asn Ile Asp Glu Thr Ala Phe Thr Gly Ala Trp Gly Asp Gly Pro Ala
            115                 120                 125 ctc cga tcc acc gcg ctc att acc tgg gcc aat tac ctg atc gct aac     480
Leu Arg Ser Thr Ala Leu Ile Thr Trp Ala Asn Tyr Leu Ile Ala Asn
        130                 135                 140 agc aac aca tcc tac gtc acc aac acc cta tgg ccc atc atc aaa ttg     528
Ser Asn Thr Ser Tyr Val Thr Asn Thr Leu Trp Pro Ile Ile Lys Leu
    145                 150                 155 gac ctc gac tac gtc gcg tcc aac tgg aac cag act agt ttc gat ttg     576
Asp Leu Asp Tyr Val Ala Ser Asn Trp Asn Gln Thr Ser Phe Asp Leu
160                 165                 170                 175 tgg gaa gaa gta tcc tct tct tcc ttc ttc act act gcg gtt caa cac     624
Trp Glu Glu Val Ser Ser Ser Ser Phe Phe Thr Thr Ala Val Gln His
                180                 185                 190
```

| | | |
|---|---|---|
| cgc tcc ctt cgc caa ggt gct tcc cta gcc act gcc att gga caa acc<br>Arg Ser Leu Arg Gln Gly Ala Ser Leu Ala Thr Ala Ile Gly Gln Thr<br>                195               200              205 | | 672 |
| tct gtc gtt ccw ggc tac acc acc cag gcc aac aat ata ctc tgc ttt<br>Ser Val Val Pro Gly Tyr Thr Thr Gln Ala Asn Asn Ile Leu Cys Phe<br>         210                215               220 | | 720 |
| caa cag tcc tac tgg aac tca gct ggg tat atg act gcc aat acc gga<br>Gln Gln Ser Tyr Trp Asn Ser Ala Gly Tyr Met Thr Ala Asn Thr Gly<br>       225               230               235 | | 768 |
| ggc ggg cgt tct ggg aaa gac gcc aac acc gtc ctc aca agt att cac<br>Gly Gly Arg Ser Gly Lys Asp Ala Asn Thr Val Leu Thr Ser Ile His<br>240                 245               250               255 | | 816 |
| aca ttc gat ccc gat gcc ggc tgc gat tcc atc act ttc caa cct tgt<br>Thr Phe Asp Pro Asp Ala Gly Cys Asp Ser Ile Thr Phe Gln Pro Cys<br>                 260               265             270 | | 864 |
| tca gac cgt gcg ctc atc aac ctt gtc aca tac gtc aat gca ttc cga<br>Ser Asp Arg Ala Leu Ile Asn Leu Val Thr Tyr Val Asn Ala Phe Arg<br>         275                280               285 | | 912 |
| agc atc tac gct atc aac gcg ggc atc gct aat aac caa ggc gtt gcc<br>Ser Ile Tyr Ala Ile Asn Ala Gly Ile Ala Asn Asn Gln Gly Val Ala<br>            290              295              300 | | 960 |
| act ggt agg tat cct gaa gat ggc tac atg ggc gga aac cct tgg tat<br>Thr Gly Arg Tyr Pro Glu Asp Gly Tyr Met Gly Gly Asn Pro Trp Tyr<br>305                 310               315 | | 1008 |
| ctg act act tta gcc gtt tct gaa cag ctc tac tac gct ctc tcc act<br>Leu Thr Thr Leu Ala Val Ser Glu Gln Leu Tyr Tyr Ala Leu Ser Thr<br>320                 325               330              335 | | 1056 |
| tgg aag aaa cat agc tcc ctc acc att acg gcg aca tca caa cct ttt<br>Trp Lys Lys His Ser Ser Leu Thr Ile Thr Ala Thr Ser Gln Pro Phe<br>                 340               345             350 | | 1104 |
| ttc gcg ctc ttc tcg ccg ggt gtt gct act ggc aca tat gcg tcc tct<br>Phe Ala Leu Phe Ser Pro Gly Val Ala Thr Gly Thr Tyr Ala Ser Ser<br>            355               360              365 | | 1152 |
| acg act acc tat gct aca ctt act act gct att cag aat tac gcg gat<br>Thr Thr Thr Tyr Ala Thr Leu Thr Thr Ala Ile Gln Asn Tyr Ala Asp<br>                 370               375             380 | | 1200 |
| agc ttc atc gct gtc gtg gct aag tat acg cct gcc aat ggc gga ctg<br>Ser Phe Ile Ala Val Val Ala Lys Tyr Thr Pro Ala Asn Gly Gly Leu<br>385                 390               395 | | 1248 |
| gcg gaa cag tac agc agg agt aac ggt ttg ccc gtt agt gcc gtt gat<br>Ala Glu Gln Tyr Ser Arg Ser Asn Gly Leu Pro Val Ser Ala Val Asp<br>400                 405               410              415 | | 1296 |
| tta act tgg agc tat gcc gct ctc ttg acg gcg gct gat gcg cga gcg<br>Leu Thr Trp Ser Tyr Ala Ala Leu Leu Thr Ala Ala Asp Ala Arg Ala<br>                 420               425             430 | | 1344 |
| ggg cta aca ccc gct gca tgg gga gca gcg ggg ttg acc gtg cca agc<br>Gly Leu Thr Pro Ala Ala Trp Gly Ala Ala Gly Leu Thr Val Pro Ser<br>            435               440              445 | | 1392 |
| act tgc tct act ggg ggt gga tca aac cca ggt ggt gga ggg tcg gtc<br>Thr Cys Ser Thr Gly Gly Gly Ser Asn Pro Gly Gly Gly Gly Ser Val<br>         450                455               460 | | 1440 |
| tct gtt acg ttc aat gtt caa gct aca acc acc ttt ggt gaa aac att<br>Ser Val Thr Phe Asn Val Gln Ala Thr Thr Thr Phe Gly Glu Asn Ile<br>465                 470               475 | | 1488 |
| ttt ttg acc ggc tcg atc aac gag tta gct aac tgg tct cct gat aat<br>Phe Leu Thr Gly Ser Ile Asn Glu Leu Ala Asn Trp Ser Pro Asp Asn<br>480                 485               490              495 | | 1536 |
| gct ctc gcc ctc tct gcg gcc aat tat ccc acc tgg agc agt acc gtc<br>Ala Leu Ala Leu Ser Ala Ala Asn Tyr Pro Thr Trp Ser Ser Thr Val<br>                 500               505             510 | | 1584 |

-continued

```
aac gtt ccc gca agc act acg atc caa tac aag ttt atc cgt aaa ttc    1632
Asn Val Pro Ala Ser Thr Thr Ile Gln Tyr Lys Phe Ile Arg Lys Phe
            515                 520                 525 aac gga gcc atc acc tgg gag tcc gac ccg aat agg cag atc aca acg    1680
Asn Gly Ala Ile Thr Trp Glu Ser Asp Pro Asn Arg Gln Ile Thr Thr
        530                 535                 540 ccg tct tcg gga agt ttt gtc cag aat gac tcg tgg aag tag            1722
Pro Ser Ser Gly Ser Phe Val Gln Asn Asp Ser Trp Lys
    545                 550                 555

<210> SEQ ID NO 26
<211> LENGTH: 573
<212> TYPE: PRT
<213> ORGANISM: Leucopaxillus giganteus

<400> SEQUENCE: 26

Met His Phe Ser Val Leu Ser Val Phe Leu Ala Ile Ser Ser Ala Trp
            -15                 -10                  -5

Ala Gln Ser Ser Ala Val Asp Ala Tyr Leu Ala Leu Glu Ser Ser Val
 -1   1                  5                  10                 15

Ala Lys Ala Gly Leu Leu Ala Asn Ile Gly Pro Ser Gly Ser Lys Ser
             20                  25                  30

Ser Gly Ala Lys Ser Gly Ile Val Ile Ala Ser Pro Ser His Ser Asn
         35                  40                  45

Pro Asp Tyr Leu Phe Thr Trp Thr Arg Asp Ser Ser Leu Val Phe Gln
     50                  55                  60

Thr Ile Ile Asn Gln Phe Thr Leu Gly His Asp Asn Ser Leu Arg Pro
 65                  70                  75

Glu Ile Asp Asn Phe Val Asp Ser Gln Arg Lys Ile Gln Gln Val Ser
 80                  85                  90                  95

Asn Pro Ser Gly Thr Val Ser Ser Gly Gly Leu Gly Glu Pro Lys Phe
             100                 105                 110

Asn Ile Asp Glu Thr Ala Phe Thr Gly Ala Trp Gly Asp Gly Pro Ala
             115                 120                 125

Leu Arg Ser Thr Ala Leu Ile Thr Trp Ala Asn Tyr Leu Ile Ala Asn
             130                 135                 140

Ser Asn Thr Ser Tyr Val Thr Asn Thr Leu Trp Pro Ile Ile Lys Leu
 145                 150                 155

Asp Leu Asp Tyr Val Ala Ser Asn Trp Asn Gln Thr Ser Phe Asp Leu
 160                 165                 170                 175

Trp Glu Glu Val Ser Ser Ser Phe Phe Thr Thr Ala Val Gln His
             180                 185                 190

Arg Ser Leu Arg Gln Gly Ala Ser Leu Ala Thr Ala Ile Gly Gln Thr
             195                 200                 205

Ser Val Val Pro Gly Tyr Thr Thr Gln Ala Asn Asn Ile Leu Cys Phe
             210                 215                 220

Gln Gln Ser Tyr Trp Asn Ser Ala Gly Tyr Met Thr Ala Asn Thr Gly
     225                 230                 235

Gly Gly Arg Ser Gly Lys Asp Ala Asn Thr Val Leu Thr Ser Ile His
 240                 245                 250                 255

Thr Phe Asp Pro Asp Ala Gly Cys Asp Ser Ile Thr Phe Gln Pro Cys
             260                 265                 270

Ser Asp Arg Ala Leu Ile Asn Leu Val Thr Tyr Val Asn Ala Phe Arg
             275                 280                 285

Ser Ile Tyr Ala Ile Asn Ala Gly Ile Ala Asn Asn Gln Gly Val Ala
             290                 295                 300
```

Thr Gly Arg Tyr Pro Glu Asp Gly Tyr Met Gly Gly Asn Pro Trp Tyr
    305                 310                 315

Leu Thr Thr Leu Ala Val Ser Glu Gln Leu Tyr Tyr Ala Leu Ser Thr
320                 325                 330                 335

Trp Lys Lys His Ser Ser Leu Thr Ile Thr Ala Thr Ser Gln Pro Phe
                340                 345                 350

Phe Ala Leu Phe Ser Pro Gly Val Ala Thr Gly Thr Tyr Ala Ser Ser
            355                 360                 365

Thr Thr Thr Tyr Ala Thr Leu Thr Thr Ala Ile Gln Asn Tyr Ala Asp
        370                 375                 380

Ser Phe Ile Ala Val Val Ala Lys Tyr Thr Pro Ala Asn Gly Gly Leu
    385                 390                 395

Ala Glu Gln Tyr Ser Arg Ser Asn Gly Leu Pro Val Ser Ala Val Asp
400                 405                 410                 415

Leu Thr Trp Ser Tyr Ala Ala Leu Leu Thr Ala Ala Asp Ala Arg Ala
                420                 425                 430

Gly Leu Thr Pro Ala Ala Trp Gly Ala Ala Gly Leu Thr Val Pro Ser
            435                 440                 445

Thr Cys Ser Thr Gly Gly Gly Ser Asn Pro Gly Gly Gly Gly Ser Val
    450                 455                 460

Ser Val Thr Phe Asn Val Gln Ala Thr Thr Phe Gly Glu Asn Ile
    465                 470                 475

Phe Leu Thr Gly Ser Ile Asn Glu Leu Ala Asn Trp Ser Pro Asp Asn
480                 485                 490                 495

Ala Leu Ala Leu Ser Ala Ala Asn Tyr Pro Thr Trp Ser Ser Thr Val
                500                 505                 510

Asn Val Pro Ala Ser Thr Thr Ile Gln Tyr Lys Phe Ile Arg Lys Phe
            515                 520                 525

Asn Gly Ala Ile Thr Trp Glu Ser Asp Pro Asn Arg Gln Ile Thr Thr
        530                 535                 540

Pro Ser Ser Gly Ser Phe Val Gln Asn Asp Ser Trp Lys
    545                 550                 555

<210> SEQ ID NO 27
<211> LENGTH: 1761
<212> TYPE: DNA
<213> ORGANISM: Artificial sequence
<220> FEATURE:
<223> OTHER INFORMATION: Hybrid Fungamyl variant JA118 with A. rolfsii

```
                50                  55                  60
gtt aca gcc cag ctg ccc cag acc acc gca tat gga gat gcc tac cat        240
Val Thr Ala Gln Leu Pro Gln Thr Thr Ala Tyr Gly Asp Ala Tyr His
 65              70                  75                  80 ggc tac tgg cag cag gat ata tac tct ctg aac gaa aac tac ggc act        288
Gly Tyr Trp Gln Gln Asp Ile Tyr Ser Leu Asn Glu Asn Tyr Gly Thr
                 85                  90                  95 gca gat gac ttg aag gcg ctc tct tcg gcc ctt cat gag agg ggg atg        336
Ala Asp Asp Leu Lys Ala Leu Ser Ser Ala Leu His Glu Arg Gly Met
            100                 105                 110 tat ctt atg gtc gat gtg gtt gct aac cat atg ggc tat gat gga ccg        384
Tyr Leu Met Val Asp Val Val Ala Asn His Met Gly Tyr Asp Gly Pro
        115                 120                 125 ggt agc tca gtc gat tac agt gtg ttt gtt ccg ttc aat tcc gct agc        432
Gly Ser Ser Val Asp Tyr Ser Val Phe Val Pro Phe Asn Ser Ala Ser
    130                 135                 140 tac ttc cac ccg ttc tgt ttc att caa aac tgg aat gat cag act cag        480
Tyr Phe His Pro Phe Cys Phe Ile Gln Asn Trp Asn Asp Gln Thr Gln
145                 150                 155                 160 gtt gag gat tgc tgg cta gga gat aac act gtc tcc ttg cct gat ctc        528
Val Glu Asp Cys Trp Leu Gly Asp Asn Thr Val Ser Leu Pro Asp Leu
                165                 170                 175 gat acc acc aag gat gtg gtc aag aat gaa tgg tac gac tgg gtg gga        576
Asp Thr Thr Lys Asp Val Val Lys Asn Glu Trp Tyr Asp Trp Val Gly
            180                 185                 190 tca ttg gta tcg aac tac tcc att gac ggc ctc cgt atc gac aca gta        624
Ser Leu Val Ser Asn Tyr Ser Ile Asp Gly Leu Arg Ile Asp Thr Val
        195                 200                 205 aaa cac gtc cag aag gac ttc tgg ccc ggg tac aac aaa gcc gca ggc        672
Lys His Val Gln Lys Asp Phe Trp Pro Gly Tyr Asn Lys Ala Ala Gly
    210                 215                 220 gtg tac tgt atc ggc gag gtg ctc gac ggt gat ccg gcc tac act tgt        720
Val Tyr Cys Ile Gly Glu Val Leu Asp Gly Asp Pro Ala Tyr Thr Cys
225                 230                 235                 240 ccc tac cag gaa gtc ctg gac ggc gta ctg aac tac ccc att tac tat        768
Pro Tyr Gln Glu Val Leu Asp Gly Val Leu Asn Tyr Pro Ile Tyr Tyr
                245                 250                 255 cca ctc ctc aac gcc ttc aag tca acc tcc ggc agc atg gac gac ctc        816
Pro Leu Leu Asn Ala Phe Lys Ser Thr Ser Gly Ser Met Asp Asp Leu
            260                 265                 270 tac aac atg atc aac acc gtc aaa tcc gac tgt cca gac tca aca ctc        864
Tyr Asn Met Ile Asn Thr Val Lys Ser Asp Cys Pro Asp Ser Thr Leu
        275                 280                 285 ctg ggc aca ttc gtc gag aac cac gac aac cca cgg ttc gct tct tac        912
Leu Gly Thr Phe Val Glu Asn His Asp Asn Pro Arg Phe Ala Ser Tyr
    290                 295                 300 acc aac gac ata gcc ctc gcc aag aac gtc gca gca ttc atc atc ctc        960
Thr Asn Asp Ile Ala Leu Ala Lys Asn Val Ala Ala Phe Ile Ile Leu
305                 310                 315                 320 aac gac gga atc ccc atc atc tac gcc ggc caa gaa cag cac tac gcc       1008
Asn Asp Gly Ile Pro Ile Ile Tyr Ala Gly Gln Glu Gln His Tyr Ala
                325                 330                 335 ggc gga aac gac ccc gcg aac cgc gaa gca acc tgg ctc tcg ggc tac       1056
Gly Gly Asn Asp Pro Ala Asn Arg Glu Ala Thr Trp Leu Ser Gly Tyr
            340                 345                 350 ccg acc gac agc gag ctg tac aag tta att gcc tcc gcg aac gca atc       1104
Pro Thr Asp Ser Glu Leu Tyr Lys Leu Ile Ala Ser Ala Asn Ala Ile
        355                 360                 365 cgg aac tat gcc att agc aaa gat aca gga ttc gtg acc tac aag aac       1152
Arg Asn Tyr Ala Ile Ser Lys Asp Thr Gly Phe Val Thr Tyr Lys Asn
```

| | | | | | | | | | | | | | | | | |
|---|---|---|---|---|---|---|---|---|---|---|---|---|---|---|---|---|
| | | 370 | | | | 375 | | | | | 380 | | | | | |
| tgg | ccc | atc | tac | aaa | gac | gac | aca | acg | atc | gcc | atg | cgc | aag | ggc | aca | 1200 |
| Trp | Pro | Ile | Tyr | Lys | Asp | Asp | Thr | Thr | Ile | Ala | Met | Arg | Lys | Gly | Thr | |
| 385 | | | | 390 | | | | | 395 | | | | | 400 | | |
| gat | ggg | tcg | cag | atc | gtg | act | atc | ttg | tcc | aac | aag | ggt | gct | tcg | ggt | 1248 |
| Asp | Gly | Ser | Gln | Ile | Val | Thr | Ile | Leu | Ser | Asn | Lys | Gly | Ala | Ser | Gly | |
| | | | | 405 | | | | | 410 | | | | | 415 | | |
| gat | tcg | tat | acc | ctc | tcc | ttg | agt | ggt | gcg | ggt | tac | aca | gcc | ggc | cag | 1296 |
| Asp | Ser | Tyr | Thr | Leu | Ser | Leu | Ser | Gly | Ala | Gly | Tyr | Thr | Ala | Gly | Gln | |
| | | | 420 | | | | | 425 | | | | | 430 | | | |
| caa | ttg | acg | gag | gtc | att | ggc | tgc | acg | acc | gtg | acg | gtt | gat | tcg | tcg | 1344 |
| Gln | Leu | Thr | Glu | Val | Ile | Gly | Cys | Thr | Thr | Val | Thr | Val | Asp | Ser | Ser | |
| | | | 435 | | | | | 440 | | | | | 445 | | | |
| gga | gat | gtg | cct | gtt | cct | atg | gcg | ggt | ggg | cta | cct | agg | gta | ttg | tat | 1392 |
| Gly | Asp | Val | Pro | Val | Pro | Met | Ala | Gly | Gly | Leu | Pro | Arg | Val | Leu | Tyr | |
| 450 | | | | | 455 | | | | | 460 | | | | | | |
| ccg | act | gag | aag | ttg | gca | ggt | agc | aag | atc | tgt | agt | agc | tcg | ggt | gct | 1440 |
| Pro | Thr | Glu | Lys | Leu | Ala | Gly | Ser | Lys | Ile | Cys | Ser | Ser | Ser | Gly | Ala | |
| 465 | | | | 470 | | | | | 475 | | | | | 480 | | |
| aca | agc | ccg | ggt | ggc | tcc | tcg | ggt | agt | gtc | gag | gtc | act | ttc | gac | gtt | 1488 |
| Thr | Ser | Pro | Gly | Gly | Ser | Ser | Gly | Ser | Val | Glu | Val | Thr | Phe | Asp | Val | |
| | | | | 485 | | | | | 490 | | | | | 495 | | |
| tac | gct | acc | aca | gta | tat | ggc | cag | aac | atc | tat | atc | acc | ggt | gat | gtg | 1536 |
| Tyr | Ala | Thr | Thr | Val | Tyr | Gly | Gln | Asn | Ile | Tyr | Ile | Thr | Gly | Asp | Val | |
| | | | 500 | | | | | 505 | | | | | 510 | | | |
| agt | gag | ctc | ggc | aac | tgg | aca | ccc | gcc | aat | ggt | gtt | gca | ctc | tct | tct | 1584 |
| Ser | Glu | Leu | Gly | Asn | Trp | Thr | Pro | Ala | Asn | Gly | Val | Ala | Leu | Ser | Ser | |
| | | 515 | | | | | 520 | | | | | 525 | | | | |
| gct | aac | tac | ccc | acc | tgg | agt | gcc | acg | atc | gct | ctc | ccc | gct | gac | acg | 1632 |
| Ala | Asn | Tyr | Pro | Thr | Trp | Ser | Ala | Thr | Ile | Ala | Leu | Pro | Ala | Asp | Thr | |
| 530 | | | | | 535 | | | | | 540 | | | | | | |
| aca | atc | cag | tac | aag | tat | gtc | aac | att | gac | ggc | agc | acc | gtc | atc | tgg | 1680 |
| Thr | Ile | Gln | Tyr | Lys | Tyr | Val | Asn | Ile | Asp | Gly | Ser | Thr | Val | Ile | Trp | |
| 545 | | | | 550 | | | | | 555 | | | | | 560 | | |
| gag | gat | gct | atc | agc | aat | cgc | gag | atc | acg | acg | ccc | gcc | agc | ggc | aca | 1728 |
| Glu | Asp | Ala | Ile | Ser | Asn | Arg | Glu | Ile | Thr | Thr | Pro | Ala | Ser | Gly | Thr | |
| | | | | 565 | | | | | 570 | | | | | 575 | | |
| tac | acc | gaa | aaa | gac | act | tgg | gat | gaa | tct | tag | | | | | | 1761 |
| Tyr | Thr | Glu | Lys | Asp | Thr | Trp | Asp | Glu | Ser | | | | | | | |
| | | | | 580 | | | | | 585 | | | | | | | |

<210> SEQ ID NO 28
<211> LENGTH: 586
<212> TYPE: PRT
<213> ORGANISM: Artificial sequence
<220> FEATURE:
<223> OTHER INFORMATION: Synthetic Construct

<400> SEQUENCE: 28

Ala Thr Pro Ala Asp Trp Arg Ser Gln Ser Ile Tyr Phe Leu Leu Thr
1               5                   10                  15

Asp Arg Phe Ala Arg Thr Asp Gly Ser Thr Thr Ala Thr Cys Asn Thr
            20                  25                  30

Ala Asp Gln Lys Tyr Cys Gly Gly Thr Trp Gln Gly Ile Ile Asp Lys
        35                  40                  45

Leu Asp Tyr Ile Gln Gly Met Gly Phe Thr Ala Ile Trp Ile Thr Pro
    50                  55                  60

Val Thr Ala Gln Leu Pro Gln Thr Thr Ala Tyr Gly Asp Ala Tyr His
65                  70                  75                  80

Gly Tyr Trp Gln Gln Asp Ile Tyr Ser Leu Asn Glu Asn Tyr Gly Thr

```
                        85                  90                  95
Ala Asp Asp Leu Lys Ala Leu Ser Ser Ala Leu His Glu Arg Gly Met
                100                 105                 110

Tyr Leu Met Val Asp Val Val Ala Asn His Met Gly Tyr Asp Gly Pro
            115                 120                 125

Gly Ser Ser Val Asp Tyr Ser Val Phe Val Pro Phe Asn Ser Ala Ser
            130                 135                 140

Tyr Phe His Pro Phe Cys Phe Ile Gln Asn Trp Asn Asp Gln Thr Gln
145                 150                 155                 160

Val Glu Asp Cys Trp Leu Gly Asp Asn Thr Val Ser Leu Pro Asp Leu
                165                 170                 175

Asp Thr Thr Lys Asp Val Val Lys Asn Glu Trp Tyr Asp Trp Val Gly
                180                 185                 190

Ser Leu Val Ser Asn Tyr Ser Ile Asp Gly Leu Arg Ile Asp Thr Val
            195                 200                 205

Lys His Val Gln Lys Asp Phe Trp Pro Gly Tyr Asn Lys Ala Ala Gly
            210                 215                 220

Val Tyr Cys Ile Gly Glu Val Leu Asp Gly Asp Pro Ala Tyr Thr Cys
225                 230                 235                 240

Pro Tyr Gln Glu Val Leu Asp Gly Val Leu Asn Tyr Pro Ile Tyr Tyr
                245                 250                 255

Pro Leu Leu Asn Ala Phe Lys Ser Thr Ser Gly Ser Met Asp Asp Leu
                260                 265                 270

Tyr Asn Met Ile Asn Thr Val Lys Ser Asp Cys Pro Asp Ser Thr Leu
            275                 280                 285

Leu Gly Thr Phe Val Glu Asn His Asp Asn Pro Arg Phe Ala Ser Tyr
            290                 295                 300

Thr Asn Asp Ile Ala Leu Ala Lys Asn Val Ala Ala Phe Ile Ile Leu
305                 310                 315                 320

Asn Asp Gly Ile Pro Ile Ile Tyr Ala Gly Gln Glu Gln His Tyr Ala
                325                 330                 335

Gly Gly Asn Asp Pro Ala Asn Arg Glu Ala Thr Trp Leu Ser Gly Tyr
                340                 345                 350

Pro Thr Asp Ser Glu Leu Tyr Lys Leu Ile Ala Ser Ala Asn Ala Ile
            355                 360                 365

Arg Asn Tyr Ala Ile Ser Lys Asp Thr Gly Phe Val Thr Tyr Lys Asn
            370                 375                 380

Trp Pro Ile Tyr Lys Asp Asp Thr Thr Ile Ala Met Arg Lys Gly Thr
385                 390                 395                 400

Asp Gly Ser Gln Ile Val Thr Ile Leu Ser Asn Lys Gly Ala Ser Gly
                405                 410                 415

Asp Ser Tyr Thr Leu Ser Leu Ser Gly Ala Gly Tyr Thr Ala Gly Gln
            420                 425                 430

Gln Leu Thr Glu Val Ile Gly Cys Thr Thr Val Thr Val Asp Ser Ser
            435                 440                 445

Gly Asp Val Pro Val Pro Met Ala Gly Gly Leu Pro Arg Val Leu Tyr
450                 455                 460

Pro Thr Glu Lys Leu Ala Gly Ser Lys Ile Cys Ser Ser Ser Gly Ala
465                 470                 475                 480

Thr Ser Pro Gly Gly Ser Gly Ser Val Glu Val Thr Phe Asp Val
                485                 490                 495

Tyr Ala Thr Thr Val Tyr Gly Gln Asn Ile Tyr Ile Thr Gly Asp Val
            500                 505                 510
```

```
Ser Glu Leu Gly Asn Trp Thr Pro Ala Asn Gly Val Ala Leu Ser Ser
            515                 520                 525

Ala Asn Tyr Pro Thr Trp Ser Ala Thr Ile Ala Leu Pro Ala Asp Thr
        530                 535                 540

Thr Ile Gln Tyr Lys Tyr Val Asn Ile Asp Gly Ser Thr Val Ile Trp
545                 550                 555                 560

Glu Asp Ala Ile Ser Asn Arg Glu Ile Thr Thr Pro Ala Ser Gly Thr
                565                 570                 575

Tyr Thr Glu Lys Asp Thr Trp Asp Glu Ser
            580                 585

<210> SEQ ID NO 29
<211> LENGTH: 558
<212> TYPE: PRT
<213> ORGANISM: Artificial sequence
<220> FEATURE:
<223> OTHER INFORMATION: Hybrid alpha-amylase with Rhizomucor pusillus
      catalytic domain and A. rolfsii linker and SBD

<400> SEQUENCE: 29

Ser Pro Leu Pro Gln Gln Arg Tyr Gly Lys Arg Ala Thr Ser Asp
1               5                   10                  15

Asp Trp Lys Ser Lys Ala Ile Tyr Gln Leu Leu Thr Asp Arg Phe Gly
            20                  25                  30

Arg Ala Asp Asp Ser Thr Ser Asn Cys Ser Asn Leu Ser Asn Tyr Cys
        35                  40                  45

Gly Gly Thr Tyr Glu Gly Ile Thr Lys His Leu Asp Tyr Ile Ser Gly
    50                  55                  60

Met Gly Phe Asp Ala Ile Trp Ile Ser Pro Ile Pro Lys Asn Ser Asp
65                  70                  75                  80

Gly Gly Tyr His Gly Tyr Trp Ala Thr Asp Phe Tyr Gln Leu Asn Ser
                85                  90                  95

Asn Phe Gly Asp Glu Ser Gln Leu Lys Ala Leu Ile Gln Ala Ala His
            100                 105                 110

Glu Arg Asp Met Tyr Val Met Leu Asp Val Val Ala Asn His Ala Gly
        115                 120                 125

Pro Thr Ser Asn Gly Tyr Ser Gly Tyr Thr Phe Gly Asp Ala Ser Leu
    130                 135                 140

Tyr His Pro Lys Cys Thr Ile Asp Tyr Asn Asp Gln Thr Ser Ile Glu
145                 150                 155                 160

Gln Cys Trp Val Ala Asp Glu Leu Pro Asp Ile Asp Thr Glu Asn Ser
                165                 170                 175

Asp Asn Val Ala Ile Leu Asn Asp Ile Val Ser Gly Trp Val Gly Asn
            180                 185                 190

Tyr Ser Phe Asp Gly Ile Arg Ile Asp Thr Val Lys His Ile Arg Lys
        195                 200                 205

Asp Phe Trp Thr Gly Tyr Ala Glu Ala Ala Gly Val Phe Ala Thr Gly
    210                 215                 220

Glu Val Phe Asn Gly Asp Pro Ala Tyr Val Gly Pro Tyr Gln Lys Tyr
225                 230                 235                 240

Leu Pro Ser Leu Ile Asn Tyr Pro Met Tyr Tyr Ala Leu Asn Asp Val
                245                 250                 255

Phe Val Ser Lys Ser Lys Gly Phe Ser Arg Ile Ser Glu Met Leu Gly
            260                 265                 270

Ser Asn Arg Asn Ala Phe Glu Asp Thr Ser Val Leu Thr Thr Phe Val
        275                 280                 285
```

```
Asp Asn His Asp Asn Pro Arg Phe Leu Asn Ser Gln Ser Asp Lys Ala
        290                 295                 300

Leu Phe Lys Asn Ala Leu Thr Tyr Val Leu Leu Gly Glu Gly Ile Pro
305                 310                 315                 320

Ile Val Tyr Tyr Gly Ser Glu Gln Gly Phe Ser Gly Gly Ala Asp Pro
                325                 330                 335

Ala Asn Arg Glu Val Leu Trp Thr Thr Asn Tyr Asp Thr Ser Ser Asp
            340                 345                 350

Leu Tyr Gln Phe Ile Lys Thr Val Asn Ser Val Arg Met Lys Ser Asn
        355                 360                 365

Lys Ala Val Tyr Met Asp Ile Tyr Val Gly Asp Asn Ala Tyr Ala Phe
370                 375                 380

Lys His Gly Asp Ala Leu Val Val Leu Asn Asn Tyr Gly Ser Gly Ser
385                 390                 395                 400

Thr Asn Gln Val Ser Phe Ser Val Ser Gly Lys Phe Asp Ser Gly Ala
                405                 410                 415

Ser Leu Met Asp Ile Val Ser Asn Ile Thr Thr Val Ser Ser Asp
            420                 425                 430

Gly Thr Val Thr Phe Asn Leu Lys Asp Gly Leu Pro Ala Ile Phe Thr
        435                 440                 445

Ser Ala Gly Ala Thr Ser Pro Gly Gly Ser Ser Gly Ser Val Glu Val
450                 455                 460

Thr Phe Asp Val Tyr Ala Thr Thr Val Tyr Gly Gln Asn Ile Tyr Ile
465                 470                 475                 480

Thr Gly Asp Val Ser Glu Leu Gly Asn Trp Thr Pro Ala Asn Gly Val
                485                 490                 495

Ala Leu Ser Ser Ala Asn Tyr Pro Thr Trp Ser Ala Thr Ile Ala Leu
            500                 505                 510

Pro Ala Asp Thr Thr Ile Gln Tyr Lys Tyr Val Asn Ile Asp Gly Ser
        515                 520                 525

Thr Val Ile Trp Glu Asp Ala Ile Ser Asn Arg Glu Ile Thr Thr Pro
530                 535                 540

Ala Ser Gly Thr Tyr Thr Glu Lys Asp Thr Trp Asp Glu Ser
545                 550                 555

<210> SEQ ID NO 30
<211> LENGTH: 574
<212> TYPE: PRT
<213> ORGANISM: Artificial sequence
<220> FEATURE:
<223> OTHER INFORMATION: Hybrid alpha-amylase with Meripilus giganteous
      catalytic domain with A. rolfsii linker and SBD.

<400> SEQUENCE: 30

Arg Pro Thr Val Phe Asp Ala Gly Ala Asp Ala His Ser Leu His Ala
1               5                   10                  15

Arg Ala Pro Ser Gly Ser Lys Asp Val Ile Ile Gln Met Phe Glu Trp
                20                  25                  30

Asn Trp Asp Ser Val Ala Ala Glu Cys Thr Asn Phe Ile Gly Pro Ala
            35                  40                  45

Gly Tyr Gly Phe Val Gln Val Ser Pro Pro Gln Glu Thr Ile Gln Gly
        50                  55                  60

Ala Gln Trp Trp Thr Asp Tyr Gln Pro Val Ser Tyr Thr Leu Thr Gly
65                  70                  75                  80

Lys Arg Gly Asp Arg Ser Gln Phe Ala Asn Met Ile Thr Thr Cys His
                85                  90                  95
```

-continued

```
Ala Ala Gly Val Gly Val Ile Val Asp Thr Ile Trp Asn His Met Ala
            100                 105                 110
Gly Val Asp Ser Gly Thr Gly Thr Ala Gly Ser Ser Phe Thr His Tyr
        115                 120                 125
Asn Tyr Pro Gly Ile Tyr Gln Asn Gln Asp Phe His His Cys Gly Leu
    130                 135                 140
Glu Pro Gly Asp Asp Ile Val Asn Tyr Asp Asn Ala Val Glu Val Gln
145                 150                 155                 160
Thr Cys Glu Leu Val Asn Leu Ala Asp Leu Ala Thr Asp Thr Glu Tyr
                165                 170                 175
Val Arg Gly Arg Leu Ala Gln Tyr Gly Asn Asp Leu Leu Ser Leu Gly
            180                 185                 190
Ala Asp Gly Leu Arg Leu Asp Ala Ser Lys His Ile Pro Val Gly Asp
        195                 200                 205
Ile Ala Asn Ile Leu Ser Arg Leu Ser Arg Ser Val Tyr Ile Thr Gln
    210                 215                 220
Glu Val Ile Phe Gly Ala Gly Glu Pro Ile Thr Pro Asn Gln Tyr Thr
225                 230                 235                 240
Gly Asn Gly Asp Val Gln Glu Phe Arg Tyr Thr Ser Ala Leu Lys Asp
                245                 250                 255
Ala Phe Leu Ser Ser Gly Ile Ser Asn Leu Gln Asp Phe Glu Asn Arg
            260                 265                 270
Gly Trp Val Pro Gly Ser Gly Ala Asn Val Phe Val Asn His Asp
        275                 280                 285
Thr Glu Arg Asn Gly Ala Ser Leu Asn Asn Ser Pro Ser Asn Thr
    290                 295                 300
Tyr Val Thr Ala Thr Ile Phe Ser Leu Ala His Pro Tyr Gly Thr Pro
305                 310                 315                 320
Thr Ile Leu Ser Ser Tyr Asp Gly Phe Thr Asn Thr Asp Ala Gly Ala
                325                 330                 335
Pro Asn Asn Asn Val Gly Thr Cys Ser Thr Ser Gly Gly Ala Asn Gly
            340                 345                 350
Trp Leu Cys Gln His Arg Trp Thr Ala Ile Ala Gly Met Val Gly Phe
        355                 360                 365
Arg Asn Asn Val Gly Ser Ala Ala Leu Asn Asn Trp Gln Ala Pro Gln
    370                 375                 380
Ser Gln Gln Ile Ala Phe Gly Arg Gly Ala Leu Gly Phe Val Ala Ile
385                 390                 395                 400
Asn Asn Ala Asp Ser Ala Trp Ser Thr Thr Phe Thr Thr Ser Leu Pro
                405                 410                 415
Asp Gly Ser Tyr Cys Asp Val Ile Ser Gly Lys Ala Ser Gly Ser Ser
            420                 425                 430
Cys Thr Gly Ser Ser Phe Thr Val Ser Gly Lys Leu Thr Ala Thr
        435                 440                 445
Val Pro Ala Arg Ser Ala Ile Ala Val His Thr Gly Gln Lys Gly Ser
    450                 455                 460
Gly Gly Gly Ala Thr Ser Pro Gly Gly Ser Ser Gly Ser Val Glu Val
465                 470                 475                 480
Thr Phe Asp Val Tyr Ala Thr Thr Val Tyr Gly Gln Asn Ile Tyr Ile
                485                 490                 495
Thr Gly Asp Val Ser Glu Leu Gly Asn Trp Thr Pro Ala Asn Gly Val
            500                 505                 510
Ala Leu Ser Ser Ala Asn Tyr Pro Thr Trp Ser Ala Thr Ile Ala Leu
        515                 520                 525
```

```
Pro Ala Asp Thr Thr Ile Gln Tyr Lys Tyr Val Asn Ile Asp Gly Ser
        530                 535                 540

Thr Val Ile Trp Glu Asp Ala Ile Ser Asn Arg Glu Ile Thr Thr Pro
545                 550                 555                 560

Ala Ser Gly Thr Tyr Thr Glu Lys Asp Thr Trp Asp Glu Ser
                565                 570

<210> SEQ ID NO 31
<211> LENGTH: 22
<212> TYPE: DNA
<213> ORGANISM: Artificial sequence
<220> FEATURE:
<223> OTHER INFORMATION: Primer

<400> SEQUENCE: 31
ggtagactag ttacctcgtt gg                                              22

<210> SEQ ID NO 32
<211> LENGTH: 23
<212> TYPE: DNA
<213> ORGANISM: Artificial sequence
<220> FEATURE:
<223> OTHER INFORMATION: Primer

<400> SEQUENCE: 32
gcttccctag ccactgccat tgg                                             23

<210> SEQ ID NO 33
<211> LENGTH: 23
<212> TYPE: DNA
<213> ORGANISM: Artificial sequence
<220> FEATURE:
<223> OTHER INFORMATION: Primer

<400> SEQUENCE: 33
gttgatttaa cttggagcta tgc                                             23

<210> SEQ ID NO 34
<211> LENGTH: 35
<212> TYPE: DNA
<213> ORGANISM: Artificial sequence
<220> FEATURE:
<223> OTHER INFORMATION: Leucopaxillus forward Primer

<400> SEQUENCE: 34
tcccttggat ccaggatgca tttctctgtc ctctc                                35

<210> SEQ ID NO 35
<211> LENGTH: 34
<212> TYPE: DNA
<213> ORGANISM: Artificial sequence
<220> FEATURE:
<223> OTHER INFORMATION: Leucopaxillus reverse Primer

<400> SEQUENCE: 35
cttatcctcg agctacttcc acgagtcatt ctgg                                 34

<210> SEQ ID NO 36
<211> LENGTH: 2166
<212> TYPE: DNA
<213> ORGANISM: Trametes cingulata
<220> FEATURE:
<221> NAME/KEY: CDS
<222> LOCATION: (1)..(171)
<220> FEATURE:
<221> NAME/KEY: misc_signal
```

```
<222> LOCATION: (1)..(54)
<220> FEATURE:
<221> NAME/KEY: mat_peptide
<222> LOCATION: (55)..(2166)
<220> FEATURE:
<221> NAME/KEY: Intron
<222> LOCATION: (172)..(244)
<220> FEATURE:
<221> NAME/KEY: CDS
<222> LOCATION: (245)..(521)
<220> FEATURE:
<221> NAME/KEY: Intron
<222> LOCATION: (522)..(577)
<220> FEATURE:
<221> NAME/KEY: CDS
<222> LOCATION: (578)..(722)
<220> FEATURE:
<221> NAME/KEY: Intron
<222> LOCATION: (723)..(772)
<220> FEATURE:
<221> NAME/KEY: CDS
<222> LOCATION: (773)..(935)
<220> FEATURE:
<221> NAME/KEY: Intron
<222> LOCATION: (936)..(1001)
<220> FEATURE:
<221> NAME/KEY: CDS
<222> LOCATION: (1002)..(1277)
<220> FEATURE:
<221> NAME/KEY: Intron
<222> LOCATION: (1278)..(1341)
<220> FEATURE:
<221> NAME/KEY: CDS
<222> LOCATION: (1342)..(1807)
<220> FEATURE:
<221> NAME/KEY: misc_feature
<222> LOCATION: (1744)..(1773)
<223> OTHER INFORMATION: Linker
<220> FEATURE:
<221> NAME/KEY: misc_feature
<222> LOCATION: (1774)..(2163)
<223> OTHER INFORMATION: binding domain
<220> FEATURE:
<221> NAME/KEY: Intron
<222> LOCATION: (1808)..(1864)
<220> FEATURE:
<221> NAME/KEY: CDS
<222> LOCATION: (1865)..(1960)
<220> FEATURE:
<221> NAME/KEY: Intron
<222> LOCATION: (1961)..(2020)
<220> FEATURE:
<221> NAME/KEY: CDS
<222> LOCATION: (2021)..(2163)

<400> SEQUENCE: 36 atg cgt ttc acg ctc ctc acc tcc ctc ctg ggc ctc gcc ctc ggc gcg      48
Met Arg Phe Thr Leu Leu Thr Ser Leu Leu Gly Leu Ala Leu Gly Ala
        -15                 -10                  -5 ttc gcg cag tcg agt gcg gcc gac gcg tac gtc gcg tcc gaa tcg ccc      96
Phe Ala Gln Ser Ser Ala Ala Asp Ala Tyr Val Ala Ser Glu Ser Pro
 -1   1               5                  10 atc gcc aag gcg ggt gtg ctc gcc aac atc ggg ccc agc ggc tcc aag     144
Ile Ala Lys Ala Gly Val Leu Ala Asn Ile Gly Pro Ser Gly Ser Lys
 15                  20                  25                  30 tcc aac gga gca aag gca agt gac aca gtgacactcc ggggcgccca            191
Ser Asn Gly Ala Lys Ala Ser Asp Thr
                 35 tgcttcattc ttctgtgcac atggtagcgc tgacatatcg ttgttttga cag ccc       247
                                                         Pro
                                                          40 ggc atc gtg att gca agt ccg agc aca tcc aac ccg aac tac ctg tac     295
Gly Ile Val Ile Ala Ser Pro Ser Thr Ser Asn Pro Asn Tyr Leu Tyr
         45                  50                  55
```

|  |  |
|---|---:|
| aca tgg acg cgc gac tcg tcc ctc gtg ttc aag gcg ctc atc gac cag<br>Thr Trp Thr Arg Asp Ser Ser Leu Val Phe Lys Ala Leu Ile Asp Gln<br>               60                       65                    70 | 343 |
| ttc acc act ggc gaa gat acc tcg ctc cga act ctg att gac gag ttc<br>Phe Thr Thr Gly Glu Asp Thr Ser Leu Arg Thr Leu Ile Asp Glu Phe<br>        75                     80                    85 | 391 |
| acc tcg gcg gag gcc ata ctc cag cag gtg ccg aac ccg agc ggg aca<br>Thr Ser Ala Glu Ala Ile Leu Gln Gln Val Pro Asn Pro Ser Gly Thr<br>90                      95                    100 | 439 |
| gtc agc act gga ggc ctc ggc gag ccc aag ttc aac atc gac gag acc<br>Val Ser Thr Gly Gly Leu Gly Glu Pro Lys Phe Asn Ile Asp Glu Thr<br>105               110                115              120 | 487 |
| gcg ttc acg gat gcc tgg ggt cgt cct cag cgc g gtaagtcgga<br>Ala Phe Thr Asp Ala Trp Gly Arg Pro Gln Arg<br>                 125                130 | 531 |
| ggttgcctcg acggagatac gcccagactg acttcaagac tctcag at ggt ccc<br>                                                               Asp Gly Pro | 585 |
| gct ctc cgg gcg act gcc atc atc acc tac gcc aac tgg ctc ctc gac<br>Ala Leu Arg Ala Thr Ala Ile Ile Thr Tyr Ala Asn Trp Leu Leu Asp<br>135               140                145              150 | 633 |
| aac aag aac acg acc tac gtg acc aac act ctc tgg cct atc atc aag<br>Asn Lys Asn Thr Thr Tyr Val Thr Asn Thr Leu Trp Pro Ile Ile Lys<br>               155                160              165 | 681 |
| ctc gac ctc gac tac gtc gcc agc aac tgg aac cag tcc ac<br>Leu Asp Leu Asp Tyr Val Ala Ser Asn Trp Asn Gln Ser Thr<br>               170                175 | 722 |
| gtatgttctc taaattctct cccgtgggta accagtctga acgttcatag g ttt gat<br>                                                                 Phe Asp | 779 |
| ctc tgg gag gag att aac tcc tcg tcg ttc ttc act acc gcc gtc cag<br>Leu Trp Glu Glu Ile Asn Ser Ser Ser Phe Phe Thr Thr Ala Val Gln<br>           185                190                195 | 827 |
| cac cgt gct ctg cgc gag ggc gcg act ttc gct aat cgc atc gga caa<br>His Arg Ala Leu Arg Glu Gly Ala Thr Phe Ala Asn Arg Ile Gly Gln<br>       200                205                210 | 875 |
| acc tcg gtg gtc agc ggg tac acc acc caa gca aac aac ctt ctc tgc<br>Thr Ser Val Val Ser Gly Tyr Thr Thr Gln Ala Asn Asn Leu Leu Cys<br>215               220                225              230 | 923 |
| ttc ctg cag gca gtctatcccg tcacacgtct gtctgtttcc gttttcccac<br>Phe Leu Gln Ala | 975 |
| agctcacctc gtcccgggcc ctgtag tcg tac tgg aac ccc acc ggc ggc tat<br>                                       Ser Tyr Trp Asn Pro Thr Gly Gly Tyr<br>                                         235                          240 | 1028 |
| atc acc gca aac acg ggc ggc ggc cgc tct ggc aag gac gcg aac acc<br>Ile Thr Ala Asn Thr Gly Gly Gly Arg Ser Gly Lys Asp Ala Asn Thr<br>       245                250                255 | 1076 |
| gtt ctc acg tcg atc cac acc ttc gac ccg gcc gct gga tgc gac gct<br>Val Leu Thr Ser Ile His Thr Phe Asp Pro Ala Ala Gly Cys Asp Ala<br>260               265                270              275 | 1124 |
| gtt acg ttc cag ccg tgc tcg gac aag gcg ctg tcg aac ttg aag gtg<br>Val Thr Phe Gln Pro Cys Ser Asp Lys Ala Leu Ser Asn Leu Lys Val<br>               280                285              290 | 1172 |
| tac gtc gat gcg ttc cgc tcg atc tac tcc atc aac agc ggg atc gcc<br>Tyr Val Asp Ala Phe Arg Ser Ile Tyr Ser Ile Asn Ser Gly Ile Ala<br>           295                300                305 | 1220 |
| tcg aat gcg gcc gtt gct acc ggc cgc tac ccc gag gac agc tac atg<br>Ser Asn Ala Ala Val Ala Thr Gly Arg Tyr Pro Glu Asp Ser Tyr Met<br>       310                315                320 | 1268 |
| ggc gga aac gtgagcgacc atttctgtgc gtacaccgcg gtcgcgttaa<br>Gly Gly Asn | 1317 |

```
ctgagatgtt ctcctctcct gtag cca tgg tac ctc acc acc tcc gcc gtc        1368
                           Pro Trp Tyr Leu Thr Thr Ser Ala Val
                                       330                 335 gct gag cag ctc tac gat gcg ctc att gtg tgg aac aag ctt ggc gcc        1416
Ala Glu Gln Leu Tyr Asp Ala Leu Ile Val Trp Asn Lys Leu Gly Ala
                340                 345                 350 ctg aac gtc acg agc acc tcc ctc ccc ttc ttc cag cag ttc tcg tca        1464
Leu Asn Val Thr Ser Thr Ser Leu Pro Phe Phe Gln Gln Phe Ser Ser
            355                 360                 365 ggc gtc acc gtc ggc acc tat gcc tca tcc tcg tcc acc ttc aag acg        1512
Gly Val Thr Val Gly Thr Tyr Ala Ser Ser Ser Ser Thr Phe Lys Thr
        370                 375                 380 ctc act tcc gcc atc aag acc ttc gcc gac ggc ttc ctc gcg gtc aac        1560
Leu Thr Ser Ala Ile Lys Thr Phe Ala Asp Gly Phe Leu Ala Val Asn
    385                 390                 395 gcc aag tac acg ccc tcg aac ggc ggc ctt gct gaa cag tac agc cgg        1608
Ala Lys Tyr Thr Pro Ser Asn Gly Gly Leu Ala Glu Gln Tyr Ser Arg
400                 405                 410                 415 agc aac ggc tcg ccc gtc agc gct gtg gac ctg acg tgg agc tat gct        1656
Ser Asn Gly Ser Pro Val Ser Ala Val Asp Leu Thr Trp Ser Tyr Ala
                420                 425                 430 gct gcc ctc acg tcg ttt gct gcg cgc tca ggc aag acg tat gcg agc        1704
Ala Ala Leu Thr Ser Phe Ala Ala Arg Ser Gly Lys Thr Tyr Ala Ser
            435                 440                 445 tgg ggc gcg gcg ggt ttg act gtc ccg acg act tgc tcg ggg agt ggc        1752
Trp Gly Ala Ala Gly Leu Thr Val Pro Thr Thr Cys Ser Gly Ser Gly
        450                 455                 460 ggt gct ggg act gtg gcc gtc acc ttc aac gtg cag gcg acc acc gtg        1800
Gly Ala Gly Thr Val Ala Val Thr Phe Asn Val Gln Ala Thr Thr Val
    465                 470                 475 ttc ggc g gtgagtacgc catcgtatgc tactagggca gttactcata gcttgtcgga      1857
Phe Gly
480 cttgtag ag aac att tac atc aca ggc tcg gtc ccc gct ctc cag aac        1905
           Glu Asn Ile Tyr Ile Thr Gly Ser Val Pro Ala Leu Gln Asn
                       485                 490                 495 tgg tcg ccc gac aac gcg ctc atc ctc tca gcg gcc aac tac ccc act       1953
Trp Ser Pro Asp Asn Ala Leu Ile Leu Ser Ala Ala Asn Tyr Pro Thr
                500                 505                 510 tgg agc a gtacgtctga accgccttca gcctgcttca tacgttcgct gacatcgggc      2010
Trp Ser atccatctag tc  acc gtg aac ctg ccg gcg agc acg acg atc gag tac        2058
               Ile Thr Val Asn Leu Pro Ala Ser Thr Thr Ile Glu Tyr
                       515                 520                 525 aag tac att cgc aag ttc aac ggc gcg gtc acc tgg gag tcc gac ccg       2106
Lys Tyr Ile Arg Lys Phe Asn Gly Ala Val Thr Trp Glu Ser Asp Pro
                530                 535                 540 aac aac tcg atc acg acg ccc gcg agc ggc acg ttc acc cag aac gac       2154
Asn Asn Ser Ile Thr Thr Pro Ala Ser Gly Thr Phe Thr Gln Asn Asp
            545                 550                 555 acc tgg cgg tag                                                        2166
Thr Trp Arg
    560

<210> SEQ ID NO 37
<211> LENGTH: 579
<212> TYPE: PRT
<213> ORGANISM: Trametes cingulata

<400> SEQUENCE: 37
```

```
Met Arg Phe Thr Leu Leu Thr Ser Leu Gly Leu Ala Leu Gly Ala
            -15                 -10                 -5

Phe Ala Gln Ser Ser Ala Ala Asp Ala Tyr Val Ala Ser Glu Ser Pro
 -1   1              5                  10

Ile Ala Lys Ala Gly Val Leu Ala Asn Ile Gly Pro Ser Gly Ser Lys
 15              20                  25                  30

Ser Asn Gly Ala Lys Ala Ser Asp Thr Pro Gly Ile Val Ile Ala Ser
                 35                  40                  45

Pro Ser Thr Ser Asn Pro Asn Tyr Leu Tyr Thr Trp Thr Arg Asp Ser
             50                  55                  60

Ser Leu Val Phe Lys Ala Leu Ile Asp Gln Phe Thr Thr Gly Glu Asp
             65                  70                  75

Thr Ser Leu Arg Thr Leu Ile Asp Glu Phe Thr Ser Ala Glu Ala Ile
         80                  85                  90

Leu Gln Gln Val Pro Asn Pro Ser Gly Thr Val Ser Thr Gly Gly Leu
 95              100                 105                 110

Gly Glu Pro Lys Phe Asn Ile Asp Glu Thr Ala Phe Thr Asp Ala Trp
                 115                 120                 125

Gly Arg Pro Gln Arg Asp Gly Pro Ala Leu Arg Ala Thr Ala Ile Ile
             130                 135                 140

Thr Tyr Ala Asn Trp Leu Leu Asp Asn Lys Asn Thr Thr Tyr Val Thr
         145                 150                 155

Asn Thr Leu Trp Pro Ile Ile Lys Leu Asp Leu Asp Tyr Val Ala Ser
 160                 165                 170

Asn Trp Asn Gln Ser Thr Phe Asp Leu Trp Glu Glu Ile Asn Ser Ser
 175                 180                 185                 190

Ser Phe Phe Thr Thr Ala Val Gln His Arg Ala Leu Arg Glu Gly Ala
             195                 200                 205

Thr Phe Ala Asn Arg Ile Gly Gln Thr Ser Val Val Ser Gly Tyr Thr
             210                 215                 220

Thr Gln Ala Asn Asn Leu Leu Cys Phe Leu Gln Ala Ser Tyr Trp Asn
             225                 230                 235

Pro Thr Gly Gly Tyr Ile Thr Ala Asn Thr Gly Gly Gly Arg Ser Gly
     240                 245                 250

Lys Asp Ala Asn Thr Val Leu Thr Ser Ile His Thr Phe Asp Pro Ala
255                  260                 265                 270

Ala Gly Cys Asp Ala Val Thr Phe Gln Pro Cys Ser Asp Lys Ala Leu
             275                 280                 285

Ser Asn Leu Lys Val Tyr Val Asp Ala Phe Arg Ser Ile Tyr Ser Ile
             290                 295                 300

Asn Ser Gly Ile Ala Ser Asn Ala Ala Val Ala Thr Gly Arg Tyr Pro
     305                 310                 315

Glu Asp Ser Tyr Met Gly Gly Asn Pro Trp Tyr Leu Thr Thr Ser Ala
     320                 325                 330

Val Ala Glu Gln Leu Tyr Asp Ala Leu Ile Val Trp Asn Lys Leu Gly
335                  340                 345                 350

Ala Leu Asn Val Thr Ser Thr Ser Leu Pro Phe Gln Gln Phe Ser
             355                 360                 365

Ser Gly Val Thr Val Gly Thr Tyr Ala Ser Ser Ser Thr Phe Lys
             370                 375                 380

Thr Leu Thr Ser Ala Ile Lys Thr Phe Ala Asp Gly Phe Leu Ala Val
             385                 390                 395

Asn Ala Lys Tyr Thr Pro Ser Asn Gly Gly Leu Ala Glu Gln Tyr Ser
```

```
                    400             405             410
Arg Ser Asn Gly Ser Pro Val Ser Ala Val Asp Leu Thr Trp Ser Tyr
415                 420                 425                 430

Ala Ala Ala Leu Thr Ser Phe Ala Ala Arg Ser Gly Lys Thr Tyr Ala
                435                 440                 445

Ser Trp Gly Ala Ala Gly Leu Thr Val Pro Thr Thr Cys Ser Gly Ser
                450                 455                 460

Gly Gly Ala Gly Thr Val Ala Val Thr Phe Asn Val Gln Ala Thr Thr
            465                 470                 475

Val Phe Gly Glu Asn Ile Tyr Ile Thr Gly Ser Val Pro Ala Leu Gln
    480                 485                 490

Asn Trp Ser Pro Asp Asn Ala Leu Ile Leu Ser Ala Ala Asn Tyr Pro
495                 500                 505                 510

Thr Trp Ser Ile Thr Val Asn Leu Pro Ala Ser Thr Thr Ile Glu Tyr
                515                 520                 525

Lys Tyr Ile Arg Lys Phe Asn Gly Ala Val Thr Trp Glu Ser Asp Pro
            530                 535                 540

Asn Asn Ser Ile Thr Thr Pro Ala Ser Gly Thr Phe Thr Gln Asn Asp
                545                 550                 555

Thr Trp Arg
    560

<210> SEQ ID NO 38
<211> LENGTH: 1740
<212> TYPE: DNA
<213> ORGANISM: Trametes cingulata
<220> FEATURE:
<221> NAME/KEY: misc_feature
<222> LOCATION: (1)..(1740)
<223> OTHER INFORMATION: cDNA
<220> FEATURE:
<221> NAME/KEY: misc_feature
<222> LOCATION: (55)..(1740)
<223> OTHER INFORMATION: mature peptide coding region of cDNA
<220> FEATURE:
<221> NAME/KEY: misc_feature
<222> LOCATION: (1435)..(1464)
<223> OTHER INFORMATION: linker
<220> FEATURE:
<221> NAME/KEY: misc_feature
<222> LOCATION: (1465)..(1740)
<223> OTHER INFORMATION: Binding domain

<400> SEQUENCE: 38
atgcgtttca cgctcctcac ctccctcctg ggcctcgccc tcggcgcgtt cgcgcagtcg      60
agtgcggccg acgcgtacgt cgcgtccgaa tcgcccatcg ccaaggcggg tgtgctcgcc     120
aacatcgggc ccagcggctc caagtccaac ggagcaaagg caagtgacac cccggcatcg     180
ntgattgcaa gtccgagcac atccaacccg aactacctgt acacatggac gcgcgactcg     240
tccctcgtgt tcaaggcgct catcgaccag ttcaccactg gcgaagatac ctcgctccga     300
actctgattg acgagttcac ctcggcggag gccatactcc agcaggtgcc gaacccgagc     360
gggacagtca gcactggagg cctcggcgag cccaagttca acatcgacga gaccgcgttc     420
acggatgcct ggggtcgtcc tcagcgcgat ggtcccgctc tccgggcgac tgccatcatc     480
acctacgcca actggctcct cgacaacaag aacacgacct acgtgaccaa cactctctgg     540
cctatcatca agctcgacct cgactacgtc gccagcaact ggaaccagtc cacgtttgat     600
ctctgggagg agattaactc ctcgtcgttc tcactaccg ccgtccagca ccgtgctctg     660
cgcgagggcg cgactttcgc taatcgcatc ggacaaacct cggtggtcag cgggtacacc     720
```

```
acccaagcaa caaccttct ctgcttcctg caggcatcgt actggaaccc caccggcggc    780
tatatcaccg caaacacggg cggcggccgc tctggcaagg acgcgaacac cgttctcacg    840
tcgatccaca ccttcgaccc ggccgctgga tgcgacgctg ttacgttcca gccgtgctcg    900
gacaaggcgc tgtcgaactt gaaggtgtac gtcgatgcgt ccgctcgat ctactccatc     960
aacagcggga tcgcctcgaa tgcggccgtt gctaccggcc gctaccccga ggacagctac   1020
atgggcggaa acccatggta cctcaccacc tccgccgtcg ctgagcagct ctacgatgcg   1080
ctcattgtgt ggaacaagct tggcgccctg aacgtcacga gcacctccct cccccttcttc 1140
cagcagttct cgtcaggcgt caccgtcggc acctatgcct catcctcgtc caccttcaag   1200
acgctcactt ccgccatcaa gaccttcgcc gacggcttcc tcgcggtcaa cgccaagtac   1260
acgccctcga acggcggcct tgctgaacag tacagccgga gcaacggctc gcccgtcagc   1320
gctgtggacc tgacgtggag ctatgctgct gccctcacgt cgtttgctgc gcgctcaggc   1380
aagacgtatg cgagctgggg cgcggcgggt ttgactgtcc cgacgacttg ctcggggagt   1440
ggcggtgctg ggactgtggc cgtcaccttc aacgtgcagg cgaccaccgt gttcggcgag   1500
aacatttaca tcacaggctc ggtccccgct ctccagaact ggtcgcccga caacgcgctc   1560
atcctctcag cggccaacta ccccacttgg agcatcaccg tgaacctgcc ggcgagcacg   1620
acgatcgagt acaagtacat tcgcaagttc aacggcgcgg tcacctggga gtccgacccg   1680
aacaactcga tcacgacgcc cgcgagcggc acgttcaccc agaacgacac ctggcggtag   1740
```

```
<210> SEQ ID NO 39
<211> LENGTH: 2182
<212> TYPE: DNA
<213> ORGANISM: Pachykytospora papyraceae
<220> FEATURE:
<221> NAME/KEY: CDS
<222> LOCATION: (1)..(159)
<220> FEATURE:
<221> NAME/KEY: misc_signal
<222> LOCATION: (1)..(54)
<220> FEATURE:
<221> NAME/KEY: mat_peptide
<222> LOCATION: (55)..(2182)
<220> FEATURE:
<221> NAME/KEY: Intron
<222> LOCATION: (160)..(238)
<220> FEATURE:
<221> NAME/KEY: CDS
<222> LOCATION: (239)..(515)
<220> FEATURE:
<221> NAME/KEY: Intron
<222> LOCATION: (516)..(565)
<220> FEATURE:
<221> NAME/KEY: misc_feature
<222> LOCATION: (523)..(524)
<223> OTHER INFORMATION: n is a, c, g, or t
<220> FEATURE:
<221> NAME/KEY: misc_feature
<222> LOCATION: (555)..(555)
<223> OTHER INFORMATION: n is a, c, g, or t
<220> FEATURE:
<221> NAME/KEY: CDS
<222> LOCATION: (566)..(713)
<220> FEATURE:
<221> NAME/KEY: misc_feature
<222> LOCATION: (613)..(613)
<223> OTHER INFORMATION: n is a, c, g, or t
<220> FEATURE:
<221> NAME/KEY: misc_feature
<222> LOCATION: (648)..(648)
<223> OTHER INFORMATION: n is a, c, g, or t
<220> FEATURE:
<221> NAME/KEY: Intron
<222> LOCATION: (714)..(775)
<220> FEATURE:
```

```
<221> NAME/KEY: misc_feature
<222> LOCATION: (727)..(727)
<223> OTHER INFORMATION: n is a, c, g, or t
<220> FEATURE:
<221> NAME/KEY: misc_feature
<222> LOCATION: (753)..(753)
<223> OTHER INFORMATION: n is a, c, g, or t
<220> FEATURE:
<221> NAME/KEY: misc_feature
<222> LOCATION: (768)..(768)
<223> OTHER INFORMATION: n is a, c, g, or t
<220> FEATURE:
<221> NAME/KEY: misc_feature
<222> LOCATION: (770)..(770)
<223> OTHER INFORMATION: n is a, c, g, or t
<220> FEATURE:
<221> NAME/KEY: CDS
<222> LOCATION: (776)..(935)
<220> FEATURE:
<221> NAME/KEY: Intron
<222> LOCATION: (936)..(971)
<220> FEATURE:
<221> NAME/KEY: CDS
<222> LOCATION: (972)..(1274)
<220> FEATURE:
<221> NAME/KEY: Intron
<222> LOCATION: (1275)..(1333)
<220> FEATURE:
<221> NAME/KEY: CDS
<222> LOCATION: (1334)..(1796)
<220> FEATURE:
<221> NAME/KEY: misc_feature
<222> LOCATION: (1736)..(1762)
<223> OTHER INFORMATION: Linker
<220> FEATURE:
<221> NAME/KEY: misc_feature
<222> LOCATION: (1763)..(2182)
<223> OTHER INFORMATION: Binding domain
<220> FEATURE:
<221> NAME/KEY: Intron
<222> LOCATION: (1797)..(1875)
<220> FEATURE:
<221> NAME/KEY: CDS
<222> LOCATION: (1876)..(1971)
<220> FEATURE:
<221> NAME/KEY: Intron
<222> LOCATION: (1972)..(2036)
<220> FEATURE:
<221> NAME/KEY: CDS
<222> LOCATION: (2037)..(2179)

<400> SEQUENCE: 39 atg cgc ttc acc ctc ctc tcc tcc ctc gtc gcc ctc gcc acc ggc gcg      48
Met Arg Phe Thr Leu Leu Ser Ser Leu Val Ala Leu Ala Thr Gly Ala
        -15                 -10                 -5 ttc acc cag acc agc cag gcc gac gcg tac gtc aag tcc gag ggc ccc      96
Phe Thr Gln Thr Ser Gln Ala Asp Ala Tyr Val Lys Ser Glu Gly Pro
  -1   1               5                  10 atc gcg aag gcg ggc ctc ctc gcc aac atc ggg ccc agc ggc tcc aag     144
Ile Ala Lys Ala Gly Leu Leu Ala Asn Ile Gly Pro Ser Gly Ser Lys
 15                  20                  25                  30 tcg cac ggg gcg aag gtgcgcttct cttttcccca ttctacgtcg cttaaagcgc     199
Ser His Gly Ala Lys
                 35 gctcatacat gtgcatgacc gcgttccgcg tgcgcgcag gcc ggt ctc gtc gtc      253
                                           Ala Gly Leu Val Val
                                                          40 gcc ccc ccc agc acg tcg gac ccc gac tac gtc tac acc tgg acg ctg     301
Ala Pro Pro Ser Thr Ser Asp Pro Asp Tyr Val Tyr Thr Trp Thr Leu
                 45                  50                  55 gat tcg tca ctc gtc ttc aag act atc atc gac cag ttc acc tcc ggg     349
Asp Ser Ser Leu Val Phe Lys Thr Ile Ile Asp Gln Phe Thr Ser Gly
         60                  65                  70
```

```
gaa gac act tcc ctc cgc aca ctc att gac cag ttc act agc gcg gag      397
Glu Asp Thr Ser Leu Arg Thr Leu Ile Asp Gln Phe Thr Ser Ala Glu
         75                  80                  85 aag gac ctc cag cag acg tcc aac cct agt ggc act gtt tcc acc ggc      445
Lys Asp Leu Gln Gln Thr Ser Asn Pro Ser Gly Thr Val Ser Thr Gly
     90                  95                 100 ggt ctc ggc gag ccc aag ttc aac atc gat ggg tcc gcg ttc acc ggt      493
Gly Leu Gly Glu Pro Lys Phe Asn Ile Asp Gly Ser Ala Phe Thr Gly
105                 110                 115                 120 gcc tgg ggt cgc cct cag cgc g gtatgcanna cagttgaagc ttgttaagcg       545
Ala Trp Gly Arg Pro Gln Arg
                125 cttacatgtn ttgtgtacag ac  ggc cct gct ctc cgc gcg act gct atc ata    597
                         Asp Gly Pro Ala Leu Arg Ala Thr Ala Ile Ile
                                         130                 135 gcc tac gct aac tgg ntg ctc gac aac aac aac ggc acg tct tac gtc      645
Ala Tyr Ala Asn Trp Xaa Leu Asp Asn Asn Asn Gly Thr Ser Tyr Val
140                 145                 150 acn aac acc ctc tgg ccc atc atc aag ctt gac ttg gac tac acc cag      693
Thr Asn Thr Leu Trp Pro Ile Ile Lys Leu Asp Leu Asp Tyr Thr Gln
155                 160                 165                 170 aac aac tgg aac cag tcg ac  gtaagttcat tatnccagct ttggctgtta         743
Asn Asn Trp Asn Gln Ser Thr
                175 gaactgcatn gatcctcatg tcttntnccc ag g ttc gac ctt tgg gag gag gtc    797
                                     Phe Asp Leu Trp Glu Glu Val
                                                     180 aac tcc tcc tct ttc ttc acg act gcc gtc cag cac cgt gct ctc cgc      845
Asn Ser Ser Ser Phe Phe Thr Thr Ala Val Gln His Arg Ala Leu Arg
185                 190                 195                 200 gag ggt atc gcc ttc gcg aag aag atc ggc caa acg tcg gtc gtg agc      893
Glu Gly Ile Ala Phe Ala Lys Lys Ile Gly Gln Thr Ser Val Val Ser
                205                 210                 215 ggc tac acc acg cag gcg acc aac ctt ctc tgc ttc ctg cag              935
Gly Tyr Thr Thr Gln Ala Thr Asn Leu Leu Cys Phe Leu Gln
            220                 225                 230 gtcagtacgc atgtgcagca cgccttctgg ctatag ctt aac ccg tgt tcc gca      989
                                        Leu Asn Pro Cys Ser Ala
                                                        235 tct tcg cag tcg tac tgg aac ccc tcg ggc ggc tat gtc act gcg aac      1037
Ser Ser Gln Ser Tyr Trp Asn Pro Ser Gly Gly Tyr Val Thr Ala Asn
                240                 245                 250 aca ggc ggc ggc cgg tcc ggc aag gac tcg aac acc gtc ctg acc tcg      1085
Thr Gly Gly Gly Arg Ser Gly Lys Asp Ser Asn Thr Val Leu Thr Ser
                255                 260                 265 atc cac acc ttc gac ccc gcc gct ggc tgc gac gcc gcg acg ttc cag      1133
Ile His Thr Phe Asp Pro Ala Ala Gly Cys Asp Ala Ala Thr Phe Gln
            270                 275                 280 ccg tgc tct gac aag gcc ctg tcc aac ctt aag gtc tac gtc gac tcg      1181
Pro Cys Ser Asp Lys Ala Leu Ser Asn Leu Lys Val Tyr Val Asp Ser
285                 290                 295                 300 ttc cgt tcc atc tac tcc atc aac agt ggc atc acc tcc aac gcc gct      1229
Phe Arg Ser Ile Tyr Ser Ile Asn Ser Gly Ile Thr Ser Asn Ala Ala
                305                 310                 315 gtc gct gtt ggc cgc tac ccc gag gat gtg tac tac aac ggc aac          1274
Val Ala Val Gly Arg Tyr Pro Glu Asp Val Tyr Tyr Asn Gly Asn
                320                 325                 330 gtgagttccg tgtcccctgc atcattgtca acagcagaaa ctgaatccca tccgcgtag     1333 ccc tgg tgc ctc tcc acg tcc gcc gtc gct gag cag ctc tac gac gcg     1381
```

```
                Pro Trp Cys Leu Ser Thr Ser Ala Val Ala Glu Gln Leu Tyr Asp Ala
                            335                 340                 345 atc atc gtc tgg aac aag ctc ggc tcg ctc gaa gtg acg agc acc tcg        1429
Ile Ile Val Trp Asn Lys Leu Gly Ser Leu Glu Val Thr Ser Thr Ser
            350                 355                 360 ctc gcg ttc ttc aag cag ctc tcc tcg gat gcc gcc gtc ggc acc tac        1477
Leu Ala Phe Phe Lys Gln Leu Ser Ser Asp Ala Ala Val Gly Thr Tyr
        365                 370                 375 tcg tcc tcg tcc gcg acg ttc aag acg ctc acc gcg gcc gcg aag acg        1525
Ser Ser Ser Ser Ala Thr Phe Lys Thr Leu Thr Ala Ala Ala Lys Thr
380                 385                 390                 395 ctc gcg gat ggc ttc ctc gct gtg aac gcg aag tac acg ccc tcg aac        1573
Leu Ala Asp Gly Phe Leu Ala Val Asn Ala Lys Tyr Thr Pro Ser Asn
                400                 405                 410 ggc ggc ctc gcg gag cag ttc agc aag agc aac ggc tcg ccg ctc agc        1621
Gly Gly Leu Ala Glu Gln Phe Ser Lys Ser Asn Gly Ser Pro Leu Ser
            415                 420                 425 gcc gtc gac ctc acg tgg agc tac gcc gcc gcg ctc acg tcc ttt gcc        1669
Ala Val Asp Leu Thr Trp Ser Tyr Ala Ala Ala Leu Thr Ser Phe Ala
        430                 435                 440 gcg cgt gag ggc aag acc ccc gcg agc tgg ggc gct gcg ggc ctc acc        1717
Ala Arg Glu Gly Lys Thr Pro Ala Ser Trp Gly Ala Ala Gly Leu Thr
445                 450                 455 gtg ccg tcg acg tgc tcg ggt aac gcg ggc ccc agc gtg aag gtg acg        1765
Val Pro Ser Thr Cys Ser Gly Asn Ala Gly Pro Ser Val Lys Val Thr
460                 465                 470                 475 ttc aac gtc cag gct acg act acc ttc ggc g gtcagtcctc ttctccaact        1816
Phe Asn Val Gln Ala Thr Thr Thr Phe Gly
                480                 485 cgtttcggtc ggtgatgttg agcattcgtc tgacgtgtgt gtgttactgc tgcttgcag      1875 ag  aac atc tac atc acc ggt aac acc gct gcg ctc cag aac tgg tcg        1922
Glu Asn Ile Tyr Ile Thr Gly Asn Thr Ala Ala Leu Gln Asn Trp Ser
            490                 495                 500 ccc gat aac gcg ctc ctc ctc tct gct gac aag tac ccc acc tgg agc a     1971
Pro Asp Asn Ala Leu Leu Leu Ser Ala Asp Lys Tyr Pro Thr Trp Ser
        505                 510                 515 gtacgtgtca tctcatctcc agcctctcat attacgttgt ttgctcatct gcatgtgctt     2031 cgcag tc  acg ctc gac ctc ccc gcg aac acc gtc gtc gag tac aaa tac     2080
          Ile Thr Leu Asp Leu Pro Ala Asn Thr Val Val Glu Tyr Lys Tyr
              520                 525                 530 atc cgc aag ttc aac ggc cag gtc acc tgg gaa tcg gac ccc aac aac       2128
Ile Arg Lys Phe Asn Gly Gln Val Thr Trp Glu Ser Asp Pro Asn Asn
        535                 540                 545 tcg atc acg acg ccc gcc gac ggt acc ttc acc cag aac gac acc tgg       2176
Ser Ile Thr Thr Pro Ala Asp Gly Thr Phe Thr Gln Asn Asp Thr Trp
550                 555                 560 cgg tga                                                                2182
Arg
565

<210> SEQ ID NO 40
<211> LENGTH: 583
<212> TYPE: PRT
<213> ORGANISM: Pachykytospora papyraceae
<220> FEATURE:
<221> NAME/KEY: misc_feature
<222> LOCATION: (144)..(144)
<223> OTHER INFORMATION: The 'Xaa' at location 144 stands for Met, Val,
      or Leu.

<400> SEQUENCE: 40
```

-continued

```
Met Arg Phe Thr Leu Leu Ser Ser Leu Val Ala Leu Ala Thr Gly Ala
            -15                 -10                  -5

Phe Thr Gln Thr Ser Gln Ala Asp Ala Tyr Val Lys Ser Glu Gly Pro
 -1   1              5                  10

Ile Ala Lys Ala Gly Leu Leu Ala Asn Ile Gly Pro Ser Gly Ser Lys
 15              20                  25                      30

Ser His Gly Ala Lys Ala Gly Leu Val Val Ala Pro Pro Ser Thr Ser
                 35                  40                  45

Asp Pro Asp Tyr Val Tyr Thr Trp Thr Leu Asp Ser Ser Leu Val Phe
             50                  55                  60

Lys Thr Ile Ile Asp Gln Phe Thr Ser Gly Glu Asp Thr Ser Leu Arg
             65                  70                  75

Thr Leu Ile Asp Gln Phe Thr Ser Ala Glu Lys Asp Leu Gln Gln Thr
 80                  85                  90

Ser Asn Pro Ser Gly Thr Val Ser Thr Gly Gly Leu Gly Glu Pro Lys
 95              100                 105                     110

Phe Asn Ile Asp Gly Ser Ala Phe Thr Gly Ala Trp Gly Arg Pro Gln
                 115                 120                     125

Arg Asp Gly Pro Ala Leu Arg Ala Thr Ala Ile Ile Ala Tyr Ala Asn
             130                 135                 140

Trp Xaa Leu Asp Asn Asn Asn Gly Thr Ser Tyr Val Thr Asn Thr Leu
             145                 150                 155

Trp Pro Ile Ile Lys Leu Asp Leu Asp Tyr Thr Gln Asn Asn Trp Asn
 160             165                 170

Gln Ser Thr Phe Asp Leu Trp Glu Glu Val Asn Ser Ser Ser Phe Phe
 175                 180                 185                 190

Thr Thr Ala Val Gln His Arg Ala Leu Arg Glu Gly Ile Ala Phe Ala
                 195                 200                 205

Lys Lys Ile Gly Gln Thr Ser Val Val Ser Gly Tyr Thr Thr Gln Ala
                 210                 215                 220

Thr Asn Leu Leu Cys Phe Leu Gln Leu Asn Pro Cys Ser Ala Ser Ser
             225                 230                 235

Gln Ser Tyr Trp Asn Pro Ser Gly Gly Tyr Val Thr Ala Asn Thr Gly
 240                 245                 250

Gly Gly Arg Ser Gly Lys Asp Ser Asn Thr Val Leu Thr Ser Ile His
 255                 260                 265                 270

Thr Phe Asp Pro Ala Ala Gly Cys Asp Ala Ala Thr Phe Gln Pro Cys
                 275                 280                 285

Ser Asp Lys Ala Leu Ser Asn Leu Lys Val Tyr Val Asp Ser Phe Arg
                 290                 295                 300

Ser Ile Tyr Ser Ile Asn Ser Gly Ile Thr Ser Asn Ala Ala Val Ala
                 305                 310                 315

Val Gly Arg Tyr Pro Glu Asp Val Tyr Tyr Asn Gly Asn Pro Trp Cys
 320                 325                 330

Leu Ser Thr Ser Ala Val Ala Glu Gln Leu Tyr Asp Ala Ile Ile Val
 335                 340                 345                 350

Trp Asn Lys Leu Gly Ser Leu Glu Val Thr Ser Thr Ser Leu Ala Phe
                 355                 360                 365

Phe Lys Gln Leu Ser Ser Asp Ala Ala Val Gly Thr Tyr Ser Ser Ser
                 370                 375                 380

Ser Ala Thr Phe Lys Thr Leu Thr Ala Ala Lys Thr Leu Ala Asp
                 385                 390                 395                 Asp

Gly Phe Leu Ala Val Asn Ala Lys Tyr Thr Pro Ser Asn Gly Gly Leu
 400                 405                 410
```

```
Ala Glu Gln Phe Ser Lys Ser Asn Gly Ser Pro Leu Ser Ala Val Asp
415                 420                 425                 430

Leu Thr Trp Ser Tyr Ala Ala Ala Leu Thr Ser Phe Ala Ala Arg Glu
            435                 440                 445

Gly Lys Thr Pro Ala Ser Trp Gly Ala Ala Gly Leu Thr Val Pro Ser
                450                 455                 460

Thr Cys Ser Gly Asn Ala Gly Pro Ser Val Lys Val Thr Phe Asn Val
        465                 470                 475

Gln Ala Thr Thr Thr Phe Gly Glu Asn Ile Tyr Ile Thr Gly Asn Thr
    480                 485                 490

Ala Ala Leu Gln Asn Trp Ser Pro Asp Asn Ala Leu Leu Leu Ser Ala
495                 500                 505                 510

Asp Lys Tyr Pro Thr Trp Ser Ile Thr Leu Asp Leu Pro Ala Asn Thr
            515                 520                 525

Val Val Glu Tyr Lys Tyr Ile Arg Lys Phe Asn Gly Gln Val Thr Trp
        530                 535                 540

Glu Ser Asp Pro Asn Asn Ser Ile Thr Thr Pro Ala Asp Gly Thr Phe
    545                 550                 555

Thr Gln Asn Asp Thr Trp Arg
    560                 565

<210> SEQ ID NO 41
<211> LENGTH: 1752
<212> TYPE: DNA
<213> ORGANISM: Pachykytospora papyraceae
<220> FEATURE:
<221> NAME/KEY: misc_feature
<222> LOCATION: (1)..(54)
<223> OTHER INFORMATION: Signal
<220> FEATURE:
<221> NAME/KEY: misc_feature
<222> LOCATION: (55)..(1752)
<223> OTHER INFORMATION: mature peptide coding cDNA
<220> FEATURE:
<221> NAME/KEY: misc_feature
<222> LOCATION: (1450)..(1476)
<223> OTHER INFORMATION: Linker
<220> FEATURE:
<221> NAME/KEY: misc_feature
<222> LOCATION: (1477)..(1752)
<223> OTHER INFORMATION: Binding domain

<400> SEQUENCE: 41
atgcgcttca ccctcctctc ctccctcgtc gccctcgcca ccggcgcgtt cacccagacc      60
agccaggccg acgcgtacgt caagtccgag ggccccatcg cgaaggcggg cctcctcgcc     120
aacatcgggc cagcggctc caagtcgcac ggggcgaagg ccggtctcgt cgtcgccccc      180
cccagcacgt cggaccccga ctacgtctac acctggacgc tggattcgtc actcgtcttc     240
aagactatca tcgaccagtt cacctccggg gaagacactt ccctccgcac actcattgac     300
cagttcacta gcgcggagaa ggacctccag cagacgtcca accctagtgg cactgttttcc    360 accggcggtc tcgcgagcc caagttcaac atcgatgggt ccgcgttcac cggtgcctgg     420
ggtcgccctc agcgcgacgg ccctgctctc cgcgcgactg ctatcatagc ctacgctaac     480
tggntgctcg acaacaacaa cggcacgtct tacgtcacya acccctctg gcccatcatc     540 aagcttgact tggactacac ccagaacaac tggaaccagt cgacgttcga cctttgggag    600
gaggtcaact cctcctcttt cttcacgact gccgtccagc accgtgctct ccgcgagggt     660
atcgccttcg cgaagaagat cggccaaacg tcggtcgtga cggcgtacac cacgcaggcg    720
accaaccttc tctgcttcct gcagcttaac ccgtgttccg catcttcgca gtcgtactgg     780
```

-continued

```
aacccctcgg gcggctatgt cactgcgaac acaggcggcg gccggtccgg caaggactcg    840
aacaccgtcc tgacctcgat ccacaccttc gaccccgccg ctggctgcga cgccgcgacg    900
ttccagccgt gctctgacaa ggccctgtcc aaccttaagg tctacgtcga ctcgttccgt    960
tccatctact ccatcaacag tggcatcacc tccaacgccg ctgtcgctgt tggccgctac   1020
cccgaggatg tgtactacaa cggcaacccc tggtgcctct ccacgtccgc cgtcgctgag   1080
cagctctacg acgcgatcat cgtctggaac aagctcggct cgctcgaagt gacgagcacc   1140
tcgctcgcgt tcttcaagca gctctcctcg gatgccgccg tcggcaccta ctcgtcctcg   1200
tccgcgacgt tcaagacgct caccgcggcc gcgaagacgc tcgcggatgg cttcctcgct   1260
gtgaacgcga agtacacgcc ctcgaacggc ggcctcgcgg agcagttcag caagagcaac   1320
ggctcgccgc tcagcgccgt cgacctcacg tggagctacg ccgccgcgct cacgtccttt   1380
gccgcgcgtg agggcaagac ccccgcgagc tggggcgctg cgggcctcac cgtgccgtcg   1440
acgtgctcgg gtaacgcggg ccccagcgtg aaggtgacgt tcaacgtcca ggctacgact   1500
accttcggcg agaacatcta catcaccggt aacaccgctg cgctccagaa ctggtcgccc   1560
gataacgcgc tcctcctctc tgctgacaag tacccccacct ggagcatcac gctcgacctc   1620
cccgcgaaca ccgtcgtcga gtacaaatac atccgcaagt tcaacggcca ggtcacctgg   1680
gaatcggacc ccaacaactc gatcacgacg cccgccgacg gtaccttcac ccagaacgac   1740
acctggcggt ga                                                       1752
```

<210> SEQ ID NO 42
<211> LENGTH: 1623
<212> TYPE: DNA
<213> ORGANISM: Leucopaxillus giganteus
<220> FEATURE:
<221> NAME/KEY: CDS
<222> LOCATION: (1)..(1620)
<223> OTHER INFORMATION: cDNA
<220> FEATURE:
<221> NAME/KEY: misc_signal
<222> LOCATION: (1)..(51)
<220> FEATURE:
<221> NAME/KEY: mat_peptide
<222> LOCATION: (52)..(1620)
<220> FEATURE:
<221> NAME/KEY: misc_feature
<222> LOCATION: (1306)..(1338)
<223> OTHER INFORMATION: linker
<220> FEATURE:
<221> NAME/KEY: misc_feature
<222> LOCATION: (1339)..(1620)
<223> OTHER INFORMATION: binding domain
<220> FEATURE:
<221> NAME/KEY: misc_feature
<222> LOCATION: (1339)..(1620)
<223> OTHER INFORMATION: binding domain

<400> SEQUENCE: 42

```
atg cat ttc tct gtc ctc tcc gta ttt ctc gcg att agt tct gct tgg     48
Met His Phe Ser Val Leu Ser Val Phe Leu Ala Ile Ser Ser Ala Trp
    -15                 -10                  -5 gct cag tct agc gca gtc gat gcc tat ctc gct ctc gaa tcc tcc gtc     96
Ala Gln Ser Ser Ala Val Asp Ala Tyr Leu Ala Leu Glu Ser Ser Val
 -1   1               5                  10                  15 gcc aag gcc ggg ttg ctc gcc aac att ggc cca tct ggt tca aag tct    144
Ala Lys Ala Gly Leu Leu Ala Asn Ile Gly Pro Ser Gly Ser Lys Ser
                20                  25                  30 tcg ggt gcc aag tct ggg att gtc att gcg tcg cct tcg cat agc aac    192
Ser Gly Ala Lys Ser Gly Ile Val Ile Ala Ser Pro Ser His Ser Asn
            35                  40                  45
```

```
cct gac tac ctg ttc acc tgg acc cgc gat tct tcg ctt gtg ttc cag      240
Pro Asp Tyr Leu Phe Thr Trp Thr Arg Asp Ser Ser Leu Val Phe Gln
         50                  55                  60 act atc atc aac cag ttc acg ttg gga cac gac aat agt ttg agg cct      288
Thr Ile Ile Asn Gln Phe Thr Leu Gly His Asp Asn Ser Leu Arg Pro
 65                  70                  75 gag att gac aat ttt gtt gat tcc caa agg aag atc caa caa gtc tca      336
Glu Ile Asp Asn Phe Val Asp Ser Gln Arg Lys Ile Gln Gln Val Ser
 80                  85                  90                  95 aac cct tcg gga act gtt agt tct ggc ggc ctt ggc gag ccc aag ttc      384
Asn Pro Ser Gly Thr Val Ser Ser Gly Gly Leu Gly Glu Pro Lys Phe
                100                 105                 110 aat atc gac gaa acc gcc ttt aca ggg gca tgg ggc aac aca tcc tac      432
Asn Ile Asp Glu Thr Ala Phe Thr Gly Ala Trp Gly Asn Thr Ser Tyr
        115                 120                 125 gtc acc aac acc cta tgg ccc atc atc aaa ttg gac ctc gac tac gtc      480
Val Thr Asn Thr Leu Trp Pro Ile Ile Lys Leu Asp Leu Asp Tyr Val
        130                 135                 140 gcg tcc aac tgg aac cag act ggt ttc gat ttg tgg gaa gaa gta tcc      528
Ala Ser Asn Trp Asn Gln Thr Gly Phe Asp Leu Trp Glu Glu Val Ser
        145                 150                 155 tct tct tcc ttc ttc act act gcg gtt caa cac cgc tcc ctt cgc caa      576
Ser Ser Ser Phe Phe Thr Thr Ala Val Gln His Arg Ser Leu Arg Gln
160                 165                 170                 175 ggt gct tcc cta gcc act gcc att gga caa acc tct gtc gtt cct ggc      624
Gly Ala Ser Leu Ala Thr Ala Ile Gly Gln Thr Ser Val Val Pro Gly
                180                 185                 190 tac acc acc cag gcc aac aat ata ctc tgc ttt caa cag tcc tac tgg      672
Tyr Thr Thr Gln Ala Asn Asn Ile Leu Cys Phe Gln Gln Ser Tyr Trp
        195                 200                 205 aac tca gct ggg tat atg act gcc aat acc gga ggc ggg cgt tct ggg      720
Asn Ser Ala Gly Tyr Met Thr Ala Asn Thr Gly Gly Gly Arg Ser Gly
        210                 215                 220 aaa gac gcc aac acc gtc ctc aca agt att cac aca ttc gat ccc gat      768
Lys Asp Ala Asn Thr Val Leu Thr Ser Ile His Thr Phe Asp Pro Asp
225                 230                 235 gcc ggc tgc gat tcc atc act ttc caa cct tgt tca gac cgt gcg ctc      816
Ala Gly Cys Asp Ser Ile Thr Phe Gln Pro Cys Ser Asp Arg Ala Leu
240                 245                 250                 255 atc aac ctt gtc aca tac gtc aat gca ttc cga agc atc tac gct atc      864
Ile Asn Leu Val Thr Tyr Val Asn Ala Phe Arg Ser Ile Tyr Ala Ile
                260                 265                 270 aac gcg ggc atc gct aat aac caa ggc gtt gcc act ggt agg tat cct      912
Asn Ala Gly Ile Ala Asn Asn Gln Gly Val Ala Thr Gly Arg Tyr Pro
        275                 280                 285 gaa gat ggc tac atg ggc gga aac ctc tac tac gct ctc tcc act tgg      960
Glu Asp Gly Tyr Met Gly Gly Asn Leu Tyr Tyr Ala Leu Ser Thr Trp
        290                 295                 300 aag aaa cat agc tcc ctc acc att acg gcg aca tca caa cct ttt ttc     1008
Lys Lys His Ser Ser Leu Thr Ile Thr Ala Thr Ser Gln Pro Phe Phe
305                 310                 315 gcg ctc ttc tcg ccg ggt gtt gct act ggc aca tat gcg tcc tct acg     1056
Ala Leu Phe Ser Pro Gly Val Ala Thr Gly Thr Tyr Ala Ser Ser Thr
320                 325                 330                 335 act acc tat gct aca ctt act act gct att cag aat tac gcg gat agc     1104
Thr Thr Tyr Ala Thr Leu Thr Thr Ala Ile Gln Asn Tyr Ala Asp Ser
                340                 345                 350 ttc atc gct gtc gtg gct aag tat acg cct gcc aat ggc gga ctg gcg     1152
Phe Ile Ala Val Val Ala Lys Tyr Thr Pro Ala Asn Gly Gly Leu Ala
        355                 360                 365
```

```
gaa cag tac agc agg agt aac ggt ttg ccc gtt agt gcc gtt gat tta    1200
Glu Gln Tyr Ser Arg Ser Asn Gly Leu Pro Val Ser Ala Val Asp Leu
        370                 375                 380 act tgg agc tat gcc gct ctc ttg acg gcg gct gat gcg cga gcg ggg    1248
Thr Trp Ser Tyr Ala Ala Leu Leu Thr Ala Ala Asp Ala Arg Ala Gly
385                 390                 395 cta aca ccc gct gca tgg gga gca gcg ggg ttg acc gtg cca agc act    1296
Leu Thr Pro Ala Ala Trp Gly Ala Ala Gly Leu Thr Val Pro Ser Thr
400                 405                 410                 415 tgc tct act ggg ggt ggt tca aac cca ggt ggt gga ggg tcg gtc tct    1344
Cys Ser Thr Gly Gly Gly Ser Asn Pro Gly Gly Gly Gly Ser Val Ser
                420                 425                 430 gtt acg ttc aat gtt caa gct aca acc acc ttt ggt gaa aac att ttt    1392
Val Thr Phe Asn Val Gln Ala Thr Thr Thr Phe Gly Glu Asn Ile Phe
                435                 440                 445 ttg acc ggc tcg atc aac gag tta gct aac tgg tct cct gat aat gct    1440
Leu Thr Gly Ser Ile Asn Glu Leu Ala Asn Trp Ser Pro Asp Asn Ala
450                 455                 460 ctc gcc ctc tct gcg gcc aat tat ccc acc tgg agc ata acc gtc aac    1488
Leu Ala Leu Ser Ala Ala Asn Tyr Pro Thr Trp Ser Ile Thr Val Asn
465                 470                 475 gtt ccc gca agc act acg atc caa tac aag ttt atc cgt aaa ttc aac    1536
Val Pro Ala Ser Thr Thr Ile Gln Tyr Lys Phe Ile Arg Lys Phe Asn
480                 485                 490                 495 gga gcc atc acc tgg gag tcc gac ccg aat agg cag atc aca acg ccg    1584
Gly Ala Ile Thr Trp Glu Ser Asp Pro Asn Arg Gln Ile Thr Thr Pro
                500                 505                 510 tct tcg gga agt ttt gtc cag aat gac tcg tgg aag tag                1623
Ser Ser Gly Ser Phe Val Gln Asn Asp Ser Trp Lys
                515                 520

<210> SEQ ID NO 43
<211> LENGTH: 540
<212> TYPE: PRT
<213> ORGANISM: Leucopaxillus giganteus

<400> SEQUENCE: 43

Met His Phe Ser Val Leu Ser Val Phe Leu Ala Ile Ser Ser Ala Trp
        -15                 -10                  -5

Ala Gln Ser Ser Ala Val Asp Ala Tyr Leu Ala Leu Glu Ser Ser Val
 -1  1                   5                  10                  15

Ala Lys Ala Gly Leu Leu Ala Asn Ile Gly Pro Ser Gly Ser Lys Ser
                 20                  25                  30

Ser Gly Ala Lys Ser Gly Ile Val Ile Ala Ser Pro Ser His Ser Asn
             35                  40                  45

Pro Asp Tyr Leu Phe Thr Trp Thr Arg Asp Ser Ser Leu Val Phe Gln
         50                  55                  60

Thr Ile Ile Asn Gln Phe Thr Leu Gly His Asp Asn Ser Leu Arg Pro
 65                  70                  75

Glu Ile Asp Asn Phe Val Asp Ser Gln Arg Lys Ile Gln Gln Val Ser
 80                  85                  90                  95

Asn Pro Ser Gly Thr Val Ser Ser Gly Gly Leu Gly Glu Pro Lys Phe
                100                 105                 110

Asn Ile Asp Glu Thr Ala Phe Thr Gly Ala Trp Gly Asn Thr Ser Tyr
            115                 120                 125

Val Thr Asn Thr Leu Trp Pro Ile Ile Lys Leu Asp Leu Asp Tyr Val
        130                 135                 140

Ala Ser Asn Trp Asn Gln Thr Gly Phe Asp Leu Trp Glu Glu Val Ser
    145                 150                 155
```

-continued

```
Ser Ser Ser Phe Phe Thr Thr Ala Val Gln His Arg Ser Leu Arg Gln
160                 165                 170                 175

Gly Ala Ser Leu Ala Thr Ala Ile Gly Gln Thr Ser Val Val Pro Gly
            180                 185                 190

Tyr Thr Thr Gln Ala Asn Asn Ile Leu Cys Phe Gln Gln Ser Tyr Trp
        195                 200                 205

Asn Ser Ala Gly Tyr Met Thr Ala Asn Thr Gly Gly Arg Ser Gly
    210                 215                 220

Lys Asp Ala Asn Thr Val Leu Thr Ser Ile His Thr Phe Asp Pro Asp
    225                 230                 235

Ala Gly Cys Asp Ser Ile Thr Phe Gln Pro Cys Ser Asp Arg Ala Leu
240                 245                 250                 255

Ile Asn Leu Val Thr Tyr Val Asn Ala Phe Arg Ser Ile Tyr Ala Ile
                260                 265                 270

Asn Ala Gly Ile Ala Asn Asn Gln Gly Val Ala Thr Gly Arg Tyr Pro
            275                 280                 285

Glu Asp Gly Tyr Met Gly Gly Asn Leu Tyr Tyr Ala Leu Ser Thr Trp
        290                 295                 300

Lys Lys His Ser Ser Leu Thr Ile Thr Ala Thr Ser Gln Pro Phe Phe
    305                 310                 315

Ala Leu Phe Ser Pro Gly Val Ala Thr Gly Thr Tyr Ala Ser Ser Thr
320                 325                 330                 335

Thr Thr Tyr Ala Thr Leu Thr Ala Ile Gln Asn Tyr Ala Asp Ser
                340                 345                 350

Phe Ile Ala Val Val Ala Lys Tyr Thr Pro Ala Asn Gly Gly Leu Ala
            355                 360                 365

Glu Gln Tyr Ser Arg Ser Asn Gly Leu Pro Val Ser Ala Val Asp Leu
        370                 375                 380

Thr Trp Ser Tyr Ala Ala Leu Leu Thr Ala Ala Asp Ala Arg Ala Gly
    385                 390                 395

Leu Thr Pro Ala Ala Trp Gly Ala Ala Gly Leu Thr Val Pro Ser Thr
400                 405                 410                 415

Cys Ser Thr Gly Gly Gly Ser Asn Pro Gly Gly Gly Ser Val Ser
                420                 425                 430

Val Thr Phe Asn Val Gln Ala Thr Thr Thr Phe Gly Glu Asn Ile Phe
            435                 440                 445

Leu Thr Gly Ser Ile Asn Glu Leu Ala Asn Trp Ser Pro Asp Asn Ala
        450                 455                 460

Leu Ala Leu Ser Ala Ala Asn Tyr Pro Thr Trp Ser Ile Thr Val Asn
    465                 470                 475

Val Pro Ala Ser Thr Thr Ile Gln Tyr Lys Phe Ile Arg Lys Phe Asn
480                 485                 490                 495

Gly Ala Ile Thr Trp Glu Ser Asp Pro Asn Arg Gln Ile Thr Thr Pro
                500                 505                 510

Ser Ser Gly Ser Phe Val Gln Asn Asp Ser Trp Lys
            515                 520
```

POLYPEPTIDES HAVING GLUCOAMYLASE ACTIVITY AND POLYNUCLEOTIDES ENCODING SAME

CROSS-REFERENCE TO RELATED APPLICATIONS

This application is a continuation of U.S. application Ser. No. 11/872,355 filed on Oct. 15, 2007, now abandoned, which is a continuation of U.S. application Ser. No. 11/315,730 filed Dec. 22, 2005 now U.S. Pat. No. 7,326,548, which claims the benefit under 35 U.S.C. 119 of U.S. provisional application Nos. 60/638,614 and 60/650,612 filed Dec. 22, 2004 and Feb. 7, 2005, respectively, the contents of which are incorporated herein by reference.

CROSS-REFERENCE TO A SEQUENCE LISTING

This application contains a Sequence Listing in computer readable form. The computer readable form is incorporated herein by reference.

BACKGROUND OF THE INVENTION

1. Field of the Invention

The present invention relates to polypeptides having glucoamylase activity and polynucleotides encoding the polypeptides. The invention also relates to nucleic acid constructs, vectors, and host cells comprising the polynucleotides as well as methods for producing and using the polypeptides, and to the use of glucoamylases of the invention for starch conversion to producing fermentation products, such as ethanol, and syrups, such as glucose. The invention also relates to a composition comprising a glucoamylase of the invention.

2. Description of the Related Art

Glucoamylase (1,4-alpha-D-glucan glucohydrolase, EC 3.2.1.3) is an enzyme, which catalyzes the release of D-glucose from the non-reducing ends of starch or related oligo- and polysaccharide molecules. Glucoamylases are produced by several filamentous fungi and yeast, with those from *Aspergillus* being commercially most important.

Commercially, glucoamylases are used to convert starchy material, which is already partially hydrolyzed by an alpha-amylase, to glucose. The glucose may then be converted directly or indirectly into a fermentation product using a fermenting organism. Examples of commercial fermentation products include alcohols (e.g., ethanol, methanol, butanol, 1,3-propanediol); organic acids (e.g., citric acid, acetic acid, itaconic acid, lactic acid, gluconic acid, gluconate, lactic acid, succinic acid, 2,5-diketo-D-gluconic acid); ketones (e.g., acetone); amino acids (e.g., glutamic acid); gases (e.g., $H_2$ and $CO_2$), and more complex compounds, including, for example, antibiotics (e.g., penicillin and tetracycline); enzymes; vitamins (e.g., riboflavin, $B_{12}$, beta-carotene); hormones, and other compounds which are difficult to produce synthetically. Fermentation processes are also commonly used in the consumable alcohol (e.g., beer and wine), dairy (e.g., in the production of yogurt and cheese), leather, and tobacco industries.

The end product may also be syrup. For instance, the end product may be glucose, but may also be converted, e.g., by glucose isomerase to fructose or a mixture composed almost equally of glucose and fructose. This mixture, or a mixture further enriched with fructose, is the most commonly used high fructose corn syrup (HFCS) commercialized throughout the world.

Boel et al., 1984, *EMBO J.* 3 (5): 1097-1102 disclose *Aspergillus niger* G1 or G2 glucoamylase.

U.S. Pat. No. 4,727,046 discloses a glucoamylase derived from *Corticium rolfsii* which is also referred to as *Athelia rolfsii*.

WO 84/02921 discloses a glucoamylase derived from *Aspergillus awamori*.

WO 99/28448 discloses a glucoamylase derived from *Talaromyces emersonii*.

WO 00/75296 discloses a glucoamylase derived from *Thermoascus crustaceus*.

It is an object of the present invention to provide polypeptides having glucoamylase activity and polynucleotides encoding the polypeptides and which provide a high yield in fermentation product production processes, such as ethanol production processes, including one-step ethanol fermentation processes from un-gelatinized raw (or uncooked) starch.

SUMMARY OF THE INVENTION

The present invention relates to polypeptides having glucoamylase activity selected from the group consisting of:

(a) a polypeptide having an amino acid sequence which has at least 75% identity with amino acids for mature polypeptide amino acids 1 to 556 of SEQ ID NO: 2; or (a1) a polypeptide having an amino acid sequence which has at least 75% identity with amino acids for mature polypeptide amino acids 1 to 561 of SEQ ID NO: 37;

(b) a polypeptide which is encoded by a nucleotide sequence (i) which hybridizes under at least low stringency conditions with nucleotides 55 to 2166 of SEQ ID NO: 1, or (ii) which hybridizes under at least medium stringency conditions with the cDNA sequence contained in nucleotides 55 to 1725 of SEQ ID NO: 3, or (iii) a complementary strand of (i) or (ii); or (b1) a polypeptide which is encoded by a nucleotide sequence (i) which hybridizes under at least low stringency conditions with nucleotides 55 to 2166 of SEQ ID NO: 36, or (ii) which hybridizes under at least medium stringency conditions with the cDNA sequence contained in nucleotides 55 to 1737 of SEQ ID NO: 38, or (iii) a complementary strand of (i) or (ii); and (c) a variant comprising a conservative substitution, deletion, and/or insertion of one or more amino acids of amino acids 1 to 556 of SEQ ID NO: 2, or (c1) a variant comprising a conservative substitution, deletion, and/or insertion of one or more amino acids of amino acids 1 to 561 of SEQ ID NO: 37, The present invention also relates to polynucleotides encoding polypeptides having glucoamylase activity, selected from the group consisting of:

(a) a polynucleotide encoding a polypeptide having an amino acid sequence which has at least 75% identity with the mature polypeptide amino acids 1 to 556 of SEQ ID NO: 2;

(a1) a polynucleotide encoding a polypeptide having an amino acid sequence which has at least 75% identity with the mature polypeptide amino acids 1 to 561 of SEQ ID NO: 37;

(b) a polynucleotide having at least 60% identity with nucleotides 55 to 2166 of SEQ ID NO: 1; or (b1) a polynucleotide having at least 60% identity with nucleotides 55 to 2166 of SEQ ID NO: 36;

(c) a polynucleotide having at least 60% identity with nucleotides 55 to 1725 of SEQ ID NO: 3; or (c1) a polynucleotide having at least 60% identity with nucleotides 55 to 1737 of SEQ ID NO: 38;

(d) a polypeptide which is encoded by a nucleotide sequence (i) which hybridizes under at least low stringency conditions with nucleotides 55 to 2166 of SEQ ID NO: 1, or (ii) which hybridizes under at least medium stringency conditions with the cDNA sequence contained in nucleotides 55 to 1725 of SEQ ID NO: 3, or (iii) a complementary strand of (i) or (ii), or (d1) a polypeptide which is encoded by a nucleotide sequence (i) which hybridizes under at least low stringency conditions with nucleotides 55 to 2166 of SEQ ID NO: 36, or (ii) which hybridizes under at least medium stringency conditions with the cDNA sequence contained in nucleotides 55 to 1737 of SEQ ID NO: 38, or (iii) a complementary strand of (i) or (ii).

In a preferred embodiment the polypeptide is derivable from a strain of the genus *Trametes*, preferably *Trametes cingulata* or the *E. coli* strain deposited at DSMZ and given the no. DSM 17106. Deposited strain DSM 17106 harbors plasmid HUda595 comprising a sequence identical to SEQ ID NO: 1. A specific polypeptide of the invention is the mature polypeptide obtained when expressing plasmid pHUda440 in a suitable fungal host cell such as *Aspergillus oryzae* as described in Example 7.

In a second aspect the present invention relates to polypeptides having glucoamylase activity selected from the group consisting of:

(a) a polypeptide having an amino acid sequence which has at least 70% identity with amino acids for mature polypeptide amino acids 1 to 575 of SEQ ID NO: 5; or (a1) a polypeptide having an amino acid sequence which has at least 70% identity with amino acids for mature polypeptide amino acids 1 to 565 of SEQ ID NO: 40;

(b) a polypeptide which is encoded by a nucleotide sequence (i) which hybridizes under at least low stringency conditions with nucleotides 55 to 2189 of SEQ ID NO: 4, or (ii) which hybridizes under at least medium stringency conditions with the cDNA sequence contained in nucleotides 55 to 1725 of SEQ ID NO: 6, or (iii) a complementary strand of (i) or (ii); or (b1) a polypeptide which is encoded by a nucleotide sequence (i) which hybridizes under at least low stringency conditions with nucleotides 55 to 2182 of SEQ ID NO: 39, or (ii) which hybridizes under at least medium stringency conditions with the cDNA sequence contained in nucleotides 55 to 1749 of SEQ ID NO: 41, or (iii) a complementary strand of (i) or (ii); and (c) a variant comprising a conservative substitution, deletion, and/or insertion of one or more amino acids of amino acids 1 to 575 of SEQ ID NO: 5, or (c1) a variant comprising a conservative substitution, deletion, and/or insertion of one or more amino acids of amino acids 1 to 565 of SEQ ID NO: 40.

The present invention also relates to polynucleotides encoding polypeptides having glucoamylase activity, selected from the group consisting of:

(a) a polynucleotide encoding a polypeptide having an amino acid sequence which has at least 75% identity with the mature polypeptide amino acids 1 to 575 of SEQ ID NO: 5; or (a1) a polynucleotide encoding a polypeptide having an amino acid sequence which has at least 75% identity with the mature polypeptide amino acids 1 to 565 of SEQ ID NO: 40;

(b) a polynucleotide having at least 60% identity with nucleotides 55 to 2189 of SEQ ID NO: 4; or (b1) a polynucleotide having at least 60% identity with nucleotides 55 to 2182 of SEQ ID NO: 39;

(c) a polynucleotide having at least 60% identity with nucleotides 55 to 1725 of SEQ ID NO: 6; or (c1) a polynucleotide having at least 60% identity with nucleotides 55 to 1749 of SEQ ID NO: 41;

(d) a polypeptide which is encoded by a nucleotide sequence (i) which hybridizes under at least low stringency conditions with nucleotides 55 to 2189 of SEQ ID NO: 4, or (ii) which hybridizes under at least medium stringency conditions with the cDNA sequence contained in nucleotides 55 to 1725 of SEQ ID NO: 6, or (iii) a complementary strand of (i) or (ii); or (d1) a polypeptide which is encoded by a nucleotide sequence (i) which hybridizes under at least low stringency conditions with nucleotides 55 to 2182 of SEQ ID NO: 39, or (ii) which hybridizes under at least medium stringency conditions with the cDNA sequence contained in nucleotides 55 to 1749 of SEQ ID NO: 41, or (iii) a complementary strand of (i) or (ii).

In a preferred embodiment the polypeptide is derivable from a strain of the genus *Pachykytospora*, preferably *Pachykytospora papyracea* or the *E. coli* strain deposited at DSMZ and given the no. DSM 17105. Deposited strain DSM 17105 harbors plasmid HUda594 comprising a sequence identical to SEQ ID NO: 4. A specific polypeptide of the invention is the mature polypeptide obtained when expressing plasmid pHUda450 in a suitable fungal host cell such as *Aspergillus oryzae* as described in Example 7.

In a third aspect the invention relates to polypeptides having glucoamylase activity selected from the group consisting of:

(a) a polypeptide having an amino acid sequence which has at least 60% identity with amino acids for mature polypeptide amino acids 1 to 556 of SEQ ID NO: 26; or (a1) a polypeptide having an amino acid sequence which has at least 60% identity with amino acids for mature polypeptide amino acids 1 to 548 of SEQ ID NO: 24; or (a2) a polypeptide having an amino acid sequence which has at least 60% identity with amino acids for mature polypeptide amino acids 1 to 523 of SEQ ID NO: 43;

(b) a polypeptide which is encoded by a nucleotide sequence (i) which hybridizes under at least low stringency conditions with nucleotides 117 to 2249 of SEQ ID NO: 23, or (ii) which hybridizes under at least low stringency conditions with the cDNA sequence contained in nucleotides 52 to 1719 of SEQ ID NO: 25, or (iii) a complementary strand of (i) or (ii);

(b1) a polypeptide which is encoded by a nucleotide sequence (i) which hybridizes under at least low stringency conditions with the cDNA sequence contained in nucleotides 52 to 1620 of SEQ ID NO: 42 or (iii) a complementary strand of (i) or (ii); and (c) a variant comprising a conservative substitution, deletion, and/or insertion of one or more amino acids of amino acids 1 to 556 of SEQ ID NO: 26, or (c1) a variant comprising a conservative substitution, deletion, and/or insertion of one or more amino acids of amino acids 1 to 548 of SEQ ID NO: 24;

(c2) a variant comprising a conservative substitution, deletion, and/or insertion of one or more amino acids of amino acids 1 to 523 of SEQ ID NO: 43.

The present invention also relates to polynucleotides encoding polypeptides having glucoamylase activity, selected from the group consisting of:

(a) a polynucleotide encoding a polypeptide having an amino acid sequence which has at least 60% identity with the mature polypeptide amino acids 1 to 556 of SEQ ID NO: 26; or (a1) a polynucleotide encoding a polypeptide having an amino acid sequence which has at least 60% identity with the mature polypeptide amino acids 1 to 548 of SEQ ID NO: 24; or (a2) a polynucleotide encoding a polypeptide having an amino acid sequence which has at least 60% identity with the mature polypeptide amino acids 1 to 523 of SEQ ID NO: 43;

(b) a polynucleotide having at least 60% identity with nucleotides 117 to 2249 of SEQ ID NO: 23; or (c) a polynucleotide having at least 60% identity with nucleotides 52 to 1719 of SEQ ID NO: 25; or (c1) a polynucleotide having at least 60% identity with nucleotides 52 to 1620 of SEQ ID NO: 42;

(d) a polypeptide which is encoded by a nucleotide sequence (i) which hybridizes under at least low stringency conditions with nucleotides 117 to 2249 of SEQ ID NO: 23, or (ii) which hybridizes under at least low stringency conditions with the cDNA sequence contained in nucleotides 52 to 1620 of SEQ ID NO: 42, or (iii) a complementary strand of (i) or (ii), or (d1) a polypeptide which is encoded by a nucleotide sequence (i) which hybridizes under at least low stringency conditions with the cDNA sequence contained in nucleotides 52 to 1719 of SEQ ID NO: 25, or (iii) a complementary strand of (i) or (ii).

In a preferred embodiment the polypeptide is derivable from a strain of the genus *Leucopaxillus*, preferably *Leucopaxillus giganteus* or the sequence shown in SEQ ID NO: 26. A specific polypeptide of the invention is the mature polypeptide obtained when expressing plasmid pENI3372 in a suitable fungal host cell such as *Aspergillus niger* as described in Example 12.

The present invention also relates to nucleic acid constructs, recombinant expression vectors, and recombinant host cells comprising the polynucleotides in SEQ ID NO: 1 or 3 (cDNA) or 36 or 38 (cDNA); or SEQ ID NO: 4 or 6 (cDNA) or 39 or 41 (cDNA); or SEQ ID NO: 23 or 25 (cDNA) or 42 (cDNA), respectively.

Clones that, to the best of the inventors belief, are identical to SEQ ID NO: 1 and 4 was deposited on 2 Feb. 2005 under the terms of the Budapest Treaty on the International Recognition of the Deposit of Microorganisms for the Purposes of Patent Procedure at Deutshe Sammmlung von Microorganismen and Zellkulturen GmbH (DSMZ), Mascheroder Weg 1b, D-38124 Braunschweig DE. The clones were giving the deposit nos. DSM 17106 and DSM 17105, respectively.

The present invention also relates to methods for producing such polypeptides having glucoamylase activity comprising (a) cultivating a recombinant host cell comprising a nucleic acid construct comprising a polynucleotide encoding the polypeptide under conditions conducive for production of the polypeptide; and (b) recovering the polypeptide.

The present invention also relates to processes of producing a fermentation product or syrup.

DEFINITIONS

Glucoamylase activity: The term glucoamylase (1,4-alpha-D-glucan glucohydrolase, EC 3.2.1.3) is defined as an enzyme, which catalyzes the release of D-glucose from the non-reducing ends of starch or related oligo- and polysaccharide molecules. For purposes of the present invention, glucoamylase activity is determined according to the procedure described in the 'Materials & Methods'-section below.

The polypeptides of the present invention have at least 20%, preferably at least 40%, more preferably at least 50%, more preferably at least 60%, more preferably at least 70%, more preferably at least 80%, even more preferably at least 90%, most preferably at least 95%, and even most preferably at least 100% of the glucoamylase activity of the polypeptide consisting of the amino acid sequence shown as amino acids 1 to 556 of SEQ ID NO: 2 or amino acids 1 to 561 of SEQ ID NO: 37; or amino acids 1 to 575 of SEQ ID NO: 5 or amino acids 1 to 565 of SEQ ID NO: 40; or amino acids 1 to 548 of SEQ ID NO: 24 or amino acids 1 to 556 of SEQ ID NO: 26 or amino acids 1 to 523 of SEQ ID NO: 43, respectively.

Polypeptide: The term "polypeptide" as used herein refers to a isolated polypeptide which is at least 20% pure, preferably at least 40% pure, more preferably at least 60% pure, even more preferably at least 80% pure, most preferably at least 90% pure, and even most preferably at least 95% pure, as determined by SDS-PAGE.

Substantially pure polypeptide: The term "substantially pure polypeptide" denotes herein a polypeptide preparation which contains at most 10%, preferably at most 8%, more preferably at most 6%, more preferably at most 5%, more preferably at most 4%, at most 3%, even more preferably at most 2%, most preferably at most 1%, and even most preferably at most 0.5% by weight of other polypeptide material with which it is natively associated. It is, therefore, preferred that the substantially pure polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation.

The polypeptides of the present invention are preferably in a substantially pure form. In particular, it is preferred that the polypeptides are in "essentially pure form", i.e., that the polypeptide preparation is essentially free of other polypeptide material with which it is natively associated. This can be accomplished, for example, by preparing the polypeptide by means of well-known recombinant methods or by classical purification methods.

Herein, the term "substantially pure polypeptide" is synonymous with the terms "isolated polypeptide" and "polypeptide in isolated form".

Identity: The relatedness between two amino acid sequences or between two nucleotide sequences is described by the parameter "identity".

For purposes of the present invention, the degree of identity between two amino acid sequences is determined by the Clustal method (Higgins, 1989, *CABIOS* 5: 151-153) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters are Ktuple=1, gap penalty=3, windows=5, and diagonals=5.

For purposes of the present invention, the degree of identity between two nucleotide sequences is determined by the Wilbur-Lipman method (Wilbur and Lipman, 1983, *Proceedings of the National Academy of Science USA* 80: 726-730) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters are Ktuple=3, gap penalty=3, and windows=20.

Polypeptide Fragment: The term "polypeptide fragment" is defined herein as a polypeptide having one or more amino acids deleted from the amino and/or carboxyl terminus of SEQ ID NO: 2 or 37; or SEQ ID NO: 5 or 40; or SEQ ID NO: 24, 26, or 43, respectively, or homologous sequences thereof, wherein the fragment has glucoamylase activity.

Subsequence: The term "subsequence" is defined herein as a nucleotide sequence having one or more nucleotides deleted from the 5' and/or 3' end of SEQ ID NO: 1, 36, or 38, respectively; or SEQ ID NO: 4, 39, or 41, or SEQ ID NO: 23, 25, or 42, respectively, or homologous sequences thereof, wherein the subsequence encodes a polypeptide fragment having glucoamylase activity.

Allelic variant: The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Substantially pure polynucleotide: The term "substantially pure polynucleotide" as used herein refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99% pure, and even most preferably at least 99.5% pure by weight. The polynucleotides of the present invention are preferably in a substantially pure form. In particular, it is preferred that the polynucleotides disclosed herein are in "essentially pure form", i.e., that the polynucleotide preparation is essentially free of other polynucleotide material with which it is natively associated. Herein, the term "substantially pure polynucleotide" is synonymous with the terms "isolated polynucleotide" and "polynucleotide in isolated form." The polynucleotides may be of genomic, cDNA, RNA, semi-synthetic, synthetic origin, or any combinations thereof.

cDNA: The term "cDNA" is defined herein as a DNA molecule which can be prepared by reverse transcription from a mature, spliced, mRNA molecule obtained from a eukaryotic cell. cDNA lacks intron sequences that are usually present in the corresponding genomic DNA. The initial, primary RNA transcript is a precursor to mRNA which is processed through a series of steps before appearing as mature spliced mRNA. These steps include the removal of intron sequences by a process called splicing. cDNA derived from mRNA lacks, therefore, any intron sequences.

Nucleic acid construct: The term "nucleic acid construct" as used herein refers to a nucleic acid molecule, either single- or double-stranded, which is isolated from a naturally occurring gene or which is modified to contain segments of nucleic acids in a manner that would not otherwise exist in nature. The term nucleic acid construct is synonymous with the term "expression cassette" when the nucleic acid construct contains the control sequences required for expression of a coding sequence of the present invention.

Control sequence: The term "control sequences" is defined herein to include all components, which are necessary or advantageous for the expression of a polynucleotide encoding a polypeptide of the present invention. Each control sequence may be native or foreign to the nucleotide sequence encoding the polypeptide. Such control sequences include, but are not limited to, a leader, polyadenylation sequence, pro-peptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" denotes herein a configuration in which a control sequence is placed at an appropriate position relative to the coding sequence of the polynucleotide sequence such that the control sequence directs the expression of the coding sequence of a polypeptide.

Coding sequence: When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG. The coding sequence may a DNA, cDNA, or recombinant nucleotide sequence.

Expression: The term "expression" includes any step involved in the production of the polypeptide including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide of the invention, and which is operably linked to additional nucleotides that provide for its expression.

Host cell: The term "host cell", as used herein, includes any cell type which is susceptible to transformation, transfection, transduction, and the like with a nucleic acid construct comprising a polynucleotide of the present invention.

Modification: The term "modification" means herein any chemical modification of the polypeptide consisting of the amino acids 1 to 556 of SEQ ID NO: 2 or amino acids 1 to 561 of SEQ ID NO: 37; or amino acids 1 to 675 of SEQ ID NO: 5 or amino acids 1 to 565 of SEQ ID NO: 40; or amino acids 1 to 556 of SEQ ID NO: 26 or SEQ ID NO: 1 to 548 of SEQ ID NO: 24 or SEQ ID NO: 1 to 523 of SEQ ID NO: 43, respectively, as well as genetic manipulation of the DNA encoding the polypeptides. The modification(s) can be substitution(s), deletion(s) and/or insertions(s) of the amino acid(s) as well as replacement(s) of amino acid side chain(s).

Artificial variant: When used herein, the term "artificial variant" means a polypeptide having glucoamylase activity produced by an organism expressing a modified nucleotide sequence of SEQ ID NO: 1 or 3 (cDNA) or SEQ ID NO: 36 or 38 (cDNA); or SEQ ID NO: 4 or 6 (cDNA), or SEQ ID NO: 39 or 41 (cDNA); or SEQ ID NO: 23 or 25 (cDNA) or 42 (cDNA). The modified nucleotide sequence is obtained through human intervention by modification of the nucleotide sequence disclosed in SEQ ID NO: 1 or 3, or SEQ ID NO: 36 or 38; or SEQ ID NO: 4 or 6, or SEQ ID NO: 39 or 41; or SEQ ID NO: 23 or 25 or 42, respectively.

BRIEF DESCRIPTION OF THE DRAWING

FIG. 1 shows the debranching activity toward pullulan of *Trametes cingulata* glucoamylase compared to glucoamylases from *Athelia rolfsii, Aspergillus niger*, and *Talaromyces emersonii*.

DETAILED DESCRIPTION OF THE INVENTION

Polypeptides Having Glucoamylase Activity

In a first aspect, the present invention relates to polypeptides having an amino acid sequence which has a degree of identity to amino acids 1 to 556 of SEQ ID NO: 2, or amino acids 1-561 of SEQ ID NO: 37; or amino acids 1-575 of SEQ ID NO: 5 or amino acids 1-565 of SEQ ID NO: 40; or amino acids 1-556 of SEQ ID NO: 26 or amino acids 1-548 of SEQ ID NO: 24 or amino acids 1-523 of SEQ ID NO: 43 (i.e., mature polypeptide), respectively.

In an embodiment the amino acid sequence has glucoamylase activity and is at least 75%, preferably at least 80%, more preferably at least 85%, even more preferably at least 90%, most preferably at least 95%, more preferred at least 96%, even more preferred at least 97%, even more preferred at least 98%, even more preferably at least 99% identical to the mature part of SEQ ID NO: 2 or SEQ ID NO: 37 (hereinafter "homologous polypeptides").

In another embodiment the amino acid sequence has glucoamylase activity and has at least 70%, more preferably at least 75%, more preferably at least 80%, more preferably at least 85%, even more preferably at least 90%, most preferably at least 95%, more preferred at least 96%, even more preferred at least 97%, even more preferred at least 98%, even more preferably at least 99% identity to the mature part of SEQ ID NO: 5 or SEQ ID NO: 40 (hereinafter "homologous polypeptides").

In an embodiment the amino acid sequence has glucoamylase activity and is at least 60%, at least 65%, at least 70%, at least 75%, preferably at least 80%, more preferably at least 85%, even more preferably at least 90%, most preferably at least 95%, more preferred at least 96%, even more preferred at least 97%, even more preferred at least 98%, even more preferably at least 99% identical to the mature part of SEQ ID NO: 26, 24 or 43, respectively (hereinafter "homologous polypeptides").

In a preferred aspect, the homologous polypeptides have an amino acid sequence which differs by ten amino acids, preferably by five amino acids, more preferably by four amino acids, even more preferably by three amino acids, most preferably by two amino acids, and even most preferably by one amino acid from amino acids 1-556 of SEQ ID NO: 2, or amino acids 1-561 of SEQ ID NO: 37; or amino acids 1-575 of SEQ ID NO: 5, or amino acids 1-565 of SEQ ID NO: 40; or amino acids 1-556 of SEQ ID NO: 26 or amino acids 1-548 of SEQ ID NO: 24 or amino acids 1-523 of SEQ ID NO: 43, respectively.

A polypeptide of the present invention preferably comprises the mature amino acid sequences of SEQ ID NO: 2 or 37; or SEQ ID NO: 5 or 40; or SEQ ID NO: 26 24 or 43, respectively, or allelic variants thereof; or fragments thereof that have glucoamylase activity, e.g., the catalytic domain.

Catalytic Domain

In an aspect, the invention relates to polypeptides that comprise the catalytic region/domain of the amino acid sequences of SEQ ID NO: 2 or 37; or SEQ ID NO: 5 or 40 or SEQ ID NO: 26, 24, or 43, respectively.

The catalytic region/domain of the *Trametes cingulata* glucoamylase is located at amino acids 1-455 in SEQ ID NO: 2 or amino acids 1-460 of SEQ ID NO: 37. In one embodiment the region may be considered to include the linker region at amino acids 456-465 of SEQ ID NO: 2 or amino acids 461-470 of SEQ ID NO: 37, respectively, or part thereof. The binding domain is encoded by polynucleotides 1423-1725 in SEQ ID NO: 3 or polynucleotides 1774-2163 of SEQ ID NO: 36 or polynucleotides 1465-1737 of SEQ ID NO: 38, respectively.

The catalytic region/domain of the *Pachykytospora papyracea* glucoamylase is located at amino acids 1-475 in SEQ ID NO: 5 or amino acids 1-465 of SEQ ID NO: 40. In one embodiment the region may be considered to include the linker region at amino acids 476-484 of SEQ ID NO: 5 or amino acids 466-474 of SEQ ID NO: 40, respectively, or part thereof. The binding domain is encoded by polynucleotides 1420-1725 in SEQ ID NO: 6 or polynucleotides 1763-2182 of SEQ ID NO: 39 or polynucleotides 1477-1749 of SEQ ID NO: 41, respectively.

The catalytic region/domain of the *Leucopaxillus giganteus* glucoamylase is located at amino acids 1-451 of SEQ ID NO: 26 or amino acids 1-455 of SEQ ID NO: 24 or amino acids 1-418 of SEQ ID NO: 43, respectively. In one embodiment the region may be considered to include the linker region at amino acids 452-461 of SEQ ID NO: 26 or amino acids 456-466 of SEQ ID NO: 24 or amino acids 419-429 of SEQ ID NO: 43, respectively, or part thereof. The binding domain (CBM) is encoded by polynucleotides 1438-1719 in SEQ ID NO: 25 or polynucleotides 1854-2249 of SEQ ID NO: 23 or polynucleotides 1339-1620 of SEQ ID NO: 42, respectively.

In a preferred embodiment the invention relates to a catalytic region which has at least 60% identity, preferably at least 65% identity, more preferably at least 70% identity, more preferably at least 75% identity, more preferably at least 80% identity, more preferably at least 85% identity, even more preferably at least 90% identity, most preferably at least 95% identity, more preferred at least 96% identity, even more preferred at least 97% identity, even more preferred at least 98% identity, even more preferably at least 99% identity, especially 100% identity to amino acids 1-455 in SEQ ID NO: 2 or amino acids 1-460 of SEQ ID NO: 37 (*Trametes*); or amino acids 1-475 in SEQ ID NO: 5 or amino acids 1-465 of SEQ ID NO: 40 (*Pachykytospora*); or amino acids 1-451 in SEQ ID NO: 26 or amino acids 1-455 of SEQ ID NO: 24 or amino acids 1-418 in SEQ ID NO: 43 (*Leucopaxillus*), respectively, and which have glucoamylase activity (hereinafter "homologous polypeptides"). In a preferred aspect, the homologous catalytic regions have amino acid sequences which differs by ten amino acids, preferably by five amino acids, more preferably by four amino acids, even more preferably by three amino acids, most preferably by two amino acids, and even most preferably by one amino acid from amino acids 1-455 of SEQ ID NO: 2 or amino acids 1-460 of SEQ ID NO: 37 (*Trametes cingulata*); or amino acids 1-475 of SEQ ID NO: 5 or amino acids 1-465 of SEQ ID NO: 40 (*Pachykytospora*) or amino acids 1-451 in SEQ ID NO: 26 or amino acids 1-455 of SEQ ID NO: 2424 or amino acids 1-418 in SEQ ID NO: 43 (*Leucopaxillus giganteus*), respectively.

Binding Domain

In another aspect, the invention relates to polypeptides having carbohydrate-binding affinity, preferably starch-binding affinity.

The binding domain in *Trametes* glucoamylase is located at amino acid 466-556 of SEQ ID NO: 2 and is encoded by polynucleotides 1420-1725 in SEQ ID NO: 3 or is located at amino acids 471-561 of SEQ ID NO: 37 and is encoded by polynucleotides 1465-1737 in SEQ ID NO: 38.

The binding domain in *Pachykytospora* glucoamylase is located at amino acids 485-575 is SEQ ID NO: 5 (*Pachykytospora*) and is encoded by polynucleotides 1423-1725 in SEQ ID NO: 6 or is located at amino acids 475-565 of SEQ ID NO: 40 and is encoded by polynucleotides 1477-1749 in SEQ ID NO: 41.

The binding domain in *Leucopaxillus* glucoamylase is located at amino acids 463-556 of SEQ ID NO: 26 or amino acids 467-548 of SEQ ID NO: 24 or amino acids 430-523 of SEQ ID NO: 43, respectively, and is encoded by polynucleotides 1854-2249 in SEQ ID NO: 23 or polynucleotides 1438-1719 in SEQ ID NO: 25 or polynucleotides 1339-1620 in SEQ ID NO: 42, respectively.

Consequently, in this aspect the invention relates to a polypeptide having carbohydrate-binding affinity, selected from the group consisting of:

(a) i) a polypeptide comprising an amino acid sequence which has at least 60% identity with amino acids 466 to 556 of SEQ ID NO: 2 or amino acids 471 to 561 of SEQ ID NO: 37, respectively; or ii) a polypeptide comprising an amino acid sequence which has at least 60% identity with amino acids 485 to 575 of SEQ ID NO: 5 or amino acids 475 to 565 of SEQ ID NO: 40, respectively; or iii) a polypeptide comprising an amino acid sequence which has at least 60% identity with amino acids 463 to 556 of SEQ ID NO: 26 or amino acids 467 to 548 of SEQ ID NO: 24, or amino acids 430 to 523 of SEQ ID NO: 43, respectively;

(b) a polypeptide which is encoded by a nucleotide sequence which hybridizes under low stringency conditions with a polynucleotide probe selected from the group consisting of (i) the complementary strand of nucleotides 1420 to 1725 of SEQ ID NO: 3 or nucleotides 1465 to 1737 of SEQ ID NO: 38, respectively;

(ii) the complementary strand of nucleotides 1423 to 1725 of SEQ ID NO: 6 or nucleotides 1477 to 1749 of SEQ ID NO: 41, respectively;

(iii) the complementary strand of nucleotides 1438 to 1719 of SEQ ID NO: 25 or nucleotides 1854 to 2249 of SEQ ID NO: 23 or nucleotides 1339 to 1620 of SEQ ID NO: 42, respectively;

(c) a fragment of (a) or (b) that has carbohydrate binding affinity.

In a preferred embodiment the carbohydrate binding affinity is starch-binding affinity.

In a preferred embodiment the invention relates to a polypeptide having carbohydrate binding affinity which has at least 60% identity, preferably at least 70% identity, more preferably at least 75% identity, more preferably at least 80% identity, more preferably at least 85% identity, even more preferably at least 90% identity, most preferably at least 95% identity, more preferred at least 96% identity, even more preferred at least 97% identity, even more preferred at least 98% identity, even more preferably at least 99% identity, especially 100% identity to amino acids 466 to 556 in SEQ ID NO: 2 or amino acids 471 to 561 of SEQ ID NO: 37, respectively, (*Trametes*), or amino acids 485 to 575 in SEQ ID NO: 5 or amino acids 475 to 565 of SEQ ID NO: 40, respectively, (*Pachykytospora*), or amino acids 463 to 556 of SEQ ID NO: 26 or amino acids 467 to 548 of SEQ ID NO: 24 or amino acids 430 to 523 of SEQ ID NO: 43, respectively (*Leucopaxillus*), respectively.

In a preferred aspect, homologous binding domains have amino acid sequences which differs by ten amino acids, preferably by five amino acids, more preferably by four amino acids, even more preferably by three amino acids, most preferably by two amino acids, and even most preferably by one amino acid from amino acids 466 to 556 of SEQ ID NO: 2 or amino acids 471 to 561 of SEQ ID NO: 37, respectively, (*Trametes cingulata*) or amino acids 485 to 575 of SEQ ID NO: 5 or amino acids 475 to 565 of SEQ ID NO: 40, respectively, (*Pachykytospora*) or amino acids 463 to 556 of SEQ ID NO: 26 or amino acids 467 to 548 of SEQ ID NO: 24 or amino acids 430 to 523 of SEQ ID NO: 43, respectively (*Leucopaxillus*), respectively.

In another embodiment the invention relates to a polypeptide having carbohydrate-binding affinity, selected from the group consisting of:

(a) a polypeptide which is encoded by a nucleotide sequence which hybridizes under low stringency conditions, preferably under medium, more preferably under high stringency conditions with a polynucleotide probe selected from the group consisting of (i) the complementary strand of nucleotides 1420 to 1725 of SEQ ID NO: 3 or nucleotides 1465 to 1737 in SEQ ID NO: 38, respectively;

(ii) the complementary strand of nucleotides 1423 to 1725 of SEQ ID NO: 6 or nucleotides 1477 to 1749 in SEQ ID NO: 41, respectively;

(iii) the complementary strand of nucleotides 1438 to 1719 of SEQ ID NO: 25 or nucleotides 1854 to 2249 in SEQ ID NO: 23 or nucleotides 1339 to 1620 in SEQ ID NO: 42, respectively;

(b) a fragment of (a) that has carbohydrate-binding affinity.

The invention also relates to a polypeptide having carbohydrate-binding affinity, where the polypeptide is an artificial variant which comprises an amino acid sequence that has at least one substitution, deletion and/or insertion of an amino acid as compared to amino acids 466 to 556 of SEQ ID NO: 2 or amino acids 471 to 561 of SEQ ID NO: 37 (*Trametes*); or amino acids 485 to 575 of SEQ ID NO: 5 or amino acids 475 to 565 of SEQ ID NO: 40 (*Pachykytospora*); or amino acids 463 to 556 of SEQ ID NO: 26 or amino acids 467 to 548 of SEQ ID NO: 24 or amino acids 430 to 523 of SEQ ID NO: 43 (*Leucopaxillus*), respectively.

The invention also relates to a polypeptide having carbohydrate-binding affinity, where the polypeptide is an artificial variant which comprises an amino acid sequence that has at least one substitution, deletion and/or insertion of an amino acid as compared to the amino acid sequence encoded by the carbohydrate-binding domain encoding part of the polynucleotide sequences shown in position 1420 to 1725 in SEQ ID NO: 3 or position 1465 to 1737 in SEQ ID NO: 38; or position 1423 to 1725 of SEQ ID NO: 6 or position 1477 to 1749 in SEQ ID NO: 41; or position 1438 to 1719 of SEQ ID NO: 25 or position 1854 to 2249 in SEQ ID NO: 23 or nucleotides 1339 to 1620 in SEQ ID NO: 42, respectively.

Hybrids

The glucoamylases or catalytic regions of the invention may be linked, via a linker sequence or directly, to one or more foreign binding domains (also referred to as binding modules (CBM)). A "foreign" binding domain is a binding-domain that is not derived from the wild-type glucoamylases of the invention in question. The binding-domain is preferably a carbohydrate-binding domain (i.e., having affinity for binding to a carbohydrate), especially a starch-binding domain or a cellulose-binding domain. Preferred binding domains are of fungal or bacterial origin. Examples of specifically contemplated starch-binding domains are disclosed in WO 2005/003311 which is hereby incorporated by reference.

In a preferred embodiment the linker in a glucoamylase of the invention is replaced with a more stable linker, i.e., a linker that is more difficult to cut than the parent linker. This is done to avoid that the binding-domain is cleaved off. Specifically contemplated stable linkers include the *Aspergillus/ kawachii* linker:

TTTTTTAAAT STSKATTSSSSSSAAATTSSS (SEQ ID NO: 22)

Thus, in a preferred embodiment the invention relates to a hybrid glucoamylase having the amino acid sequence shown in SEQ ID NO: 2 or 37, respectively, wherein the native linker located from amino acids 456 to 465 of SEQ ID NO: 2 or from amino acids 461 to 470 in SEQ ID NO: 37, respectively, or part thereof, is replaced with the *Aspergillus kawachii* linker shown in SEQ ID NO: 22.

Thus, in another preferred embodiment the invention relates to a hybrid glucoamylase having the amino acid sequence shown in SEQ ID NO: 5 or 40, respectively, wherein the native linker located from 476 to 484 in SEQ ID NO: 5 or from amino acids 466 to 474 in SEQ ID NO: 40, respectively, or part thereof is replaced with the *Aspergillus kawachii* linker shown in SEQ ID NO: 22.

Thus, in another preferred embodiment the invention relates to a hybrid glucoamylase having the amino acid sequence shown in SEQ ID NO: 26 or 24, respectively, wherein the native linker located from 452 to 462 in SEQ ID NO: 26 or from amino acids 456 466 in SEQ ID NO: 24 or from amino acids 419 to 429 in SEQ ID NO: 24, respectively, or part thereof is replaced with the *Aspergillus kawachii* linker shown in SEQ ID NO: 22.

Thus, the invention also relates to hybrids consisting of a glucoamylase of the invention or catalytic domain of the invention having glucoamylase activity fused to a stable linker (e.g., *Aspergillus kawachii* linker) and one or more carbohydrate-binding domains, e.g., a carbohydrate-binding module (CBM) disclosed in WO 2005/003311 on page 5, line 30 to page 8, line 12, hereby incorporated by reference.

Hybridization

In another aspect, the present invention relates to polypeptides having glucoamylase activity which are encoded by polynucleotides (i) which hybridizes under at least low stringency conditions, preferably medium stringency conditions, more preferably medium-high stringency conditions, even more preferably high stringency conditions, and most preferably very high stringency conditions with a nucleotide sequence with nucleotides 55 to 2166 of SEQ ID NO: 1 or nucleotides 55 to 2166 of SEQ ID NO: 36, respectively (*Trametes* genomic DNA), or (ii) which hybridizes under at least medium stringency conditions, preferably medium-high stringency conditions, more preferably high stringency conditions, and more preferably very high stringency conditions with a nucleotide sequence with the cDNA sequence contained in nucleotides 55 to 1725 of SEQ ID NO: 3 or nucleotides 55 to 1737 of SEQ ID NO: 38, respectively (*Trametes* cDNA), or (iii) a subsequence of (i) or (ii), or (iv) a complementary strand of (i), (ii), or (iii) (J. Sambrook, E. F. Fritsch, and T. Maniatis, 1989, *Molecular Cloning, A Laboratory Manual,* 2d edition, Cold Spring Harbor, N.Y.). A subsequence of SEQ ID NOS: 1 or 3, or SEQ ID NOS: 36 or 38 (*Trametes*) contains at least 100 contiguous nucleotides or preferably at least 200 continguous nucleotides. Moreover, the subsequence may encode a polypeptide fragment which has glucoamylase activity.

The invention also relates to isolated polypeptides having glucoamylase activity which are encoded by polynucleotides (i) which hybridizes under at least low stringency conditions, preferably medium stringency conditions, more preferably medium-high stringency conditions, even more preferably high stringency conditions, and most preferably very high stringency conditions with a nucleotide sequence with nucleotides 55 to 2189 of SEQ ID NO: 4 or nucleotides 55 to 2182 of SEQ ID NO: 39, respectively (*Pachykytospora* genomic DNA), or (ii) which hybridizes under at least medium stringency conditions, preferably medium-high stringency conditions, more preferably high stringency conditions, and even more preferably very high stringency conditions with a nucleotide sequence with the cDNA sequence contained in nucleotides 55 to 1725 of SEQ ID NO: 6 or nucleotides 55 to 1749 of SEQ ID NO: 41, respectively (*Pachykytospora* cDNA), or (iii) a subsequence of (i) or (ii), or (iv) a complementary strand of (i), (ii), or (iii).

The invention also relates to isolated polypeptides having glucoamylase activity which are encoded by polynucleotides (i) which hybridizes under at least low stringency conditions, preferably medium stringency conditions, more preferably medium-high stringency conditions, even more preferably high stringency conditions, and most preferably very high stringency conditions with a nucleotide sequence with nucleotides 117 to 2249 of SEQ ID NO: 23 (*Leucopaxillus* genomic DNA), or (ii) which hybridizes under at least low stringency conditions, preferably medium, more preferably medium-high stringency conditions, more preferably high stringency conditions, and even more preferably very high stringency conditions with a nucleotide sequence with the cDNA sequence contained in nucleotides 52 to 1719 of SEQ ID NO: 25 or nucleotides 52 to 1620 of SEQ ID NO: 42 (*Leucopaxillus* cDNA), or (iii) a subsequence of (i) or (ii), or (iv) a complementary strand of (i), (ii), or (iii)

The nucleotide sequence of SEQ ID NO: 1, 3, 36, or 38, respectively, or a subsequence thereof, or the nucleotide sequence of SEQ ID NO: 4, 6, 39, or 41, respectively, or a subsequence thereof, or the nucleotide sequence of SEQ ID NO: 23, 25 or 42, respectively, or a subsequence thereof, as well as the amino acid sequence of SEQ ID NO: 2 or 37, respectively, or a fragment thereof, or the amino acid sequence of SEQ ID NO: 5 or 40, respectively, or a fragment thereof, or the amino acid sequence of SEQ ID NO: 26, 24, or 43, respectively, or a fragment thereof, may be used to design a nucleic acid probe to identify and clone DNA encoding polypeptides having glucoamylase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is however, preferred that the nucleic acid probe is at least 100 nucleotides in length. For example, the nucleic acid probe may be at least 200 nucleotides, preferably at least 300 nucleotides, more preferably at least 400 nucleotides, or most preferably at least 500 nucleotides in length. Even longer probes may be used, e.g., nucleic acid probes which are at least 600 nucleotides, at least preferably at least 700 nucleotides, more preferably at least 800 nucleotides, or most preferably at least 900 nucleotides in length. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

A genomic DNA or cDNA library prepared from such other organisms may, therefore, be screened for DNA which hybridizes with the probes described above and which encodes a polypeptide having glucoamylase activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO: 1, 3, 36, or 38, respectively, or a subsequence thereof, or SEQ ID NO: 4, 6, 39 or 41, respectively, or a subsequence thereof, or SEQ ID NO: 23, 25, or 42, respectively, or a subsequence thereof, the carrier material is used in a Southern blot.

For purposes of the present invention, hybridization indicates that the nucleotide sequences hybridize to labeled nucleic acid probes corresponding to the nucleotide sequence shown in SEQ ID NO: 1, 3, 36 or 38, respectively, or SEQ ID NO: 4, 6, 39, or 41, respectively, or SEQ ID NO: 23, 25, or 42, respectively, its complementary strands, or subsequences thereof, under low or medium to very high stringency conditions. Molecules to which the nucleic acid probe hybridizes under these conditions can be detected using X-ray film.

In a preferred embodiment, the nucleic acid probe is nucleotides 55 to 2166 of SEQ ID NO: 1 or nucleotides 55 to 2166 of SEQ ID NO: 36, or nucleotides 1 to 1725 of SEQ ID NO: 3 or nucleotides 55 to 1737 of SEQ ID NO: 38 (*Trametes* cDNA). In a preferred embodiment, the nucleic acid probe is nucleotides 55 to 2186 of SEQ ID NO: 4 or nucleotides 55 to 2182 of SEQ ID NO: 39 or nucleotides 1 to 1725 of SEQ ID NO: 6 or nucleotides 55 to 1749 of SEQ ID NO: 41 (*Pachykytospora* cDNA). In a preferred embodiment, the nucleic acid probe is nucleotides 117 to 2249 of SEQ ID NO: 23 or nucleotides 52 to 1719 of SEQ ID NO: 25 (*Leucopaxillus* cDNA) or nucleotides 52 to 1620 of SEQ ID NO: 42 (*Leucopaxillus* cDNA). In other preferred aspect, the nucleic acid probe is a polynucleotide sequence which encodes the catalytic region between amino acids 1 and 455 of SEQ ID NO: 2 or amino acids 1 to 460 of SEQ ID NO: 37 (*Trametes*) or between amino acids 1 and 475 of SEQ ID NO: 5 or amino acids 1 to 465 of SEQ ID NO: 40 (*Pachykytospora*) or between amino acids 1 and 455 of SEQ ID NO: 24 or amino acids 1 to 451 of SEQ ID NO: 26 or amino acids 1 to 418 of SEQ ID NO: 43 (*Leucopaxillus*).

In another aspect the invention relates to nucleic acid probes that encode the binding domain in amino acids 466 to 456 of SEQ ID NO: 2 or amino acids 471 to 561 of SEQ ID NO: 37, respectively, or amino acids 485 to 575 of SEQ ID NO: 5 or amino acids 475 to 565 of SEQ ID NO: 40, respectively, or amino acids 463 to 556 of SEQ ID NO: 26 or amino acids 467 to 548 of SEQ ID NO: 24 or amino acids 430 to 523 of SEQ ID NO: 43, respectively.

In another preferred aspect, the nucleic acid probe is the mature polypeptide coding region of SEQ ID NO: 1, 3, 36 or 38, respectively (*Trametes*). In another preferred embodiment, the nucleic acid probe is the mature polypeptide coding region of SEQ ID NO: 4, 6, 39 or 41 (*Pachykytospora*). In another preferred embodiment, the nucleic acid probe is the mature polypeptide coding region of SEQ ID NOS: 23, 25, or 42 (*Leucopaxillus*). In another preferred aspect, the nucleic acid probe is the part of the sequences in plasmids pHUda595 and pHUda594, respectively, coding for the mature polypeptides of the invention Plasmids pHUda595 and pHUda594, which are contained in *Escherichia coli* DSM 17106 and *Escherichia coli* DSM 17105, respectively, encode polypeptides having glucoamylase activity.

For long probes of at least 100 nucleotides in length, low to very high stringency conditions are defined as prehybridization and hybridization at 42° C. in 5×SSPE, 0.3% SDS, 200 micro g/ml sheared and denatured salmon sperm DNA, and either 25% formamide for low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing post-hybridization at about 5° C. to about 10° C. below the calculated $T_m$, using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

Under salt-containing hybridization conditions, the effective $T_m$ is what controls the degree of identity required between the probe and the filter bound DNA for successful hybridization. The effective $T_m$ may be determined using the formula below to determine the degree of identity required for two DNAs to hybridize under various stringency conditions.

$$\text{Effective } T_m = 81.5 \pm 16.6(\log M[\text{Na}^+]) + 0.41(\%G+C) - 0.72(\% \text{ formamide})$$

(See www.ndsu.nodak.edu/instruct/mcclean/plsc731/dna/dna6.htm)

The G+C content of SEQ ID NO: 1 or nucleotides 55 to 2166 of SEQ ID NO: 1 is 60.5%. The G+C content of SEQ ID NO: 3 (cDNA) or nucleotides 55 to 1725 of SEQ ID NO: 3 is 62.3%.

The G+C content of SEQ ID NO: 4 or nucleotides 55 to 2189 of SEQ ID NO: 4 is 60.7%. The G+C content of SEQ ID NO: 6 (cDNA) or nucleotides 55 to 1725 of SEQ ID NO: 6 is 63.7%.

For medium stringency, the formamide is 35% and the Na$^+$ concentration for 5×SSPE is 0.75 M. Applying this formula to these values, the Effective $T_m$ is 79.0° C.

Another relevant relationship is that a 1% mismatch of two DNAs lowers the $T_m$ by 1.4° C. To determine the degree of identity required for two DNAs to hybridize under medium stringency conditions at 42° C., the following formula is used:

$$\% \text{ Homology} = 100 - [(\text{Effective } T_m - \text{Hybridization Temperature})/1.4]$$

(See ndsu.nodak.edu/instruct/mcclean/plsc731/dna/dna6.htm)

Applying this formula to the values, the degree of identity required for two DNAs to hybridize under medium stringency conditions at 42° C. is 100−[(79.0−42)/1.4]=51%.

Variants

In a further aspect, the present invention relates to artificial variants comprising a conservative substitution, deletion, and/or insertion of one or more amino acids in SEQ ID NOS: 2, 5, 24, 26, 37, 40, and 43, respectively, or the mature polypeptide thereof. Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter specific activity are known in the art and are described, for example, by H. Neurath and R. L. Hill, 1979, *In, The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in the parent polypeptides can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for biological activity (i.e., glucoamylase activity) to identify amino acid residues that are critical to the activity of the molecule. See also, Hilton et al., 1996, *J. Biol. Chem.* 271: 4699-4708. The active site of the enzymes or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309:59-64. The identities of essential amino acids can also be inferred from analysis of identities with polypeptides which are related to a polypeptide according to the invention.

Single or multiple amino acid substitutions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochem.* 30:10832-10837; U.S. Pat. No. 5,223,409; WO 92/06204), and region-directed mutagenesis (Derbyshire et al., 1986, *Gene* 46:145; Ner et al., 1988, *DNA* 7:127).

Mutagenesis/shuffling methods can be combined with high-throughput, automated screening methods to detect activity of cloned, mutagenized polypeptides expressed by host cells. Mutagenized DNA molecules that encode active polypeptides can be recovered from the host cells and rapidly sequenced using standard methods in the art. These methods allow the rapid determination of the importance of individual amino acid residues in a polypeptide of interest, and can be applied to polypeptides of unknown structure.

The total number of amino acid substitutions, deletions and/or insertions of amino acids in position 1 to 556 of SEQ ID NO: 2 or position 1 to 561 of SEQ ID NO: 37 (*Trametes* glucoamylase); or in position 1 to 575 in SEQ ID NO: 5 or position 1 to 565 in SEQ ID NO: 40 (*Pachykytospora* glucoamylase) or position 1 to 556 of SEQ ID NO: 26 or position 1 to 548 of SEQ ID NO: 24 or position 1 to 523 of SEQ ID NO: 43 (*Leucopaxilus* glucoamylase), respectively, is 10, preferably 9, more preferably 8, more preferably 7, more preferably at most 6, more preferably at most 5, more preferably 4, even more preferably 3, most preferably 2, and even most preferably 1.

Sources of Polypeptides Having Glucoamylase Activity

A polypeptide of the present invention may be obtained from microorganisms of any genus. For purposes of the present invention, the term "obtained from" as used herein in connection with a given source shall mean that the polypeptide encoded by a nucleotide sequence is produced by the source or by a strain in which the nucleotide sequence from the source has been inserted. In a preferred aspect, the polypeptide obtained from a given source is secreted extracellularly.

In a preferred embodiment, the glucoamylase of the invention derived from the class Basidiomycetes. In a more preferred embodiment a glucoamylase of the invention is derived from a strain of the genus *Trametes*, more preferably from a strain of the species *Trametes cingulata*, or deposited clone DSM 17106, or a strain of the genus *Pachykytospora* more preferably a strain of the species *Pachykytospora papyracea*, or the deposited clone DSM 17105, or a strain of the genus *Leucopaxillus*, more preferably a strain of the species *Leucopaxillus giganteus*.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

The *Trametes cingulata* strain was collected in Zimbabwe in the period from 1995 to 1997.

The *Pachykytospora papyracea* strain was collected in Zimbabwe in the period from 1995 to 1997.

The *Leucopaxillus giganteus* strain was collected in Denmark in 2003.

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The polynucleotide may then be obtained by similarly screening a genomic or cDNA library of another microorganism. Once a polynucleotide sequence encoding a polypeptide has been detected with the probe(s), the polynucleotide can be isolated or cloned by utilizing techniques which are well known to those of ordinary skill in the art (see, e.g., Sambrook et al., 1989, supra).

Polypeptides of the present invention also include fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

Polynucleotides

The present invention also relates to isolated polynucleotides having a nucleotide sequence which encode a polypeptide of the present invention. In a preferred aspect, the nucleotide sequence is set forth in any of SEQ ID NO: 1, 3, 4, 6, 23, 25, 36, 38, 39, 41, or 42, respectively. In another more preferred aspect, the nucleotide sequence is the sequence contained in plasmid pHuda595 or pHuda594 that is contained in Escherichia coli DSM 17106 and Escherichia coli DSM 17105, respectively. In another preferred aspect, the nucleotide sequence is the mature polypeptide coding region of any of SEQ ID NO: 1, 3, 4, 6, 23, 25, 36, 38, 39, 41, or 42, respectively. The present invention also encompasses nucleotide sequences which encode a polypeptide having the amino acid sequence of any of SEQ ID NO: 2, 5, 24, 26, 37, 40, or 43, respectively, or the mature polypeptide thereof, which differs from SEQ ID NO: 1, 3, 4, 6, 23, 25, 36, 38, 39, 41, or 42 respectively, by virtue of the degeneracy of the genetic code. The present invention also relates to subsequences of any of SEQ ID NO: 1, 3, 4, 6, 23, 25, 36, 38, 39, 41, or 42, respectively, which encode fragments of SEQ ID NO: 2, 5, 24, 26, 37, 39, 40, or 43 respectively, that have glucoamylase activity.

The present invention also relates to mutant polynucleotides comprising at least one mutation in the mature polypeptide coding sequence of any of SEQ ID NO: 1, 3, 4, 6, 23, 25, 36, 38, 39, 41, or 42, respectively, in which the mutant nucleotide sequence encodes a polypeptide which consists of amino acids 1 to 556 of SEQ ID NO: 2, amino acids 1 to 575 of SEQ ID NO: 5, amino acids 1 to 548 of SEQ ID NO: 24, amino acid 1 to 556 of SEQ ID NO: 26, amino acids 1 to 561 of SEQ ID NO: 37, amino acids 1 to 565 of SEQ ID NO: 40, or amino acids 1 to 523 of SEQ ID NO: 43, respectively.

The techniques used to isolate or clone a polynucleotide encoding a polypeptide are known in the art and include isolation from genomic DNA, preparation from cDNA, or a combination thereof. The cloning of the polynucleotides of the present invention from such genomic DNA can be effected, e.g., by using the well known polymerase chain reaction (PCR) or antibody screening of expression libraries to detect cloned DNA fragments with shared structural features. See, e.g., Innis et al., 1990, PCR: A Guide to Methods and Application, Academic Press, New York. Other nucleic acid amplification procedures such as ligase chain reaction (LCR), ligated activated transcription (LAT) and nucleotide sequence-based amplification (NASBA) may be used. The polynucleotides may be cloned from a strain of the genera Trametes, Pachykytospora, Leucopaxillus or other or related organisms and thus, for example, may be an allelic or species variant of the polypeptide encoding region of the nucleotide sequences.

The present invention also relates to polynucleotides having nucleotide sequences which have a degree of identity to the mature polypeptide coding sequence of SEQ ID NO: 1 (i.e., nucleotides 55 to 2166), or SEQ ID NO: 3 (i.e., nucleotides 55 to 1725), or SEQ ID NO: 4 (i.e., nucleotides 55 to 2182), or SEQ ID NO: 6 (i.e., nucleotides 55 to 1725), or SEQ ID NO: 25 (i.e., nucleotides 52 to 1719), or SEQ ID NO: 38 (i.e., nucleotide 55 to 1737), or SEQ ID NO: 41 (i.e., nucleotide 55 to 1749), or SEQ ID NO: 42 (i.e., nucleotide 55 to 1620), respectively, of at least 60%, preferably at least 65%, more preferably at least 70%, more preferably at least 75%, more preferably at least 80%, more preferably at least 85%, more preferably at least 90%, even more preferably at least 95%, even more preferably 96%, even more 97%, even more 98%, and most preferably at least 99% identity, which encode an active polypeptide.

Modification of a nucleotide sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., artificial variants that differ in specific activity, thermostability, pH optimum, or the like. The variant sequence may be constructed on the basis of the nucleotide sequence presented as the mature polypeptide encoding region of any of SEQ ID NO: 1, 3, 4, 6, 23, 25, 36, 38, 39, 41, or 42, respectively, e.g., subsequences thereof, and/or by introduction of nucleotide substitutions, which do not give rise to another amino acid sequence of the polypeptide encoded by the nucleotide sequence, but which correspond to the codon usage of the host organism intended for production of the enzyme, or by introduction of nucleotide substitutions which may give rise to a different amino acid sequence. For a general description of nucleotide substitution, see, e.g., Ford et al., 1991, Protein Expression and Purification 2: 95-107.

It will be apparent to those skilled in the art that such substitutions can be made outside the regions critical to the function of the molecule and still result in an active polypeptide. Amino acid residues essential to the activity of the polypeptide encoded by an isolated polynucleotide of the invention, and therefore preferably not subject to substitution, may be identified according to procedures known in the art, such as site-directed mutagenesis or alanine-scanning mutagenesis (see, e.g., Cunningham and Wells, 1989, Science 244: 1081-1085). In the latter technique, mutations are introduced at every positively charged residue in the molecule, and the resultant mutant molecules are tested for glucoamylase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, Science 255: 306-312; Smith et al., 1992, Journal of Molecular Biology 224: 899-904; Wlodaver et al., 1992, FEBS Letters 309: 59-64).

The present invention also relates to isolated polynucleotides encoding a polypeptide of the present invention, (i) which hybridize under low stringency conditions, more preferably medium stringency conditions, more preferably medium-high stringency conditions, even more preferably high stringency conditions, and most preferably very high stringency conditions with nucleotides 55 to 2166 of SEQ ID NO: 1 or nucleotides 55 to 2166 of SEQ ID NO: 36, respectively, or (ii) which hybridize under medium stringency conditions, more preferably medium-high stringency conditions, even more preferably high stringency conditions, and most preferably very high stringency conditions with nucleotides the cDNA sequence contained in nucleotides 55 to 1725 of SEQ ID NO: 3 or nucleotides 55 to 1737 of SEQ ID NO: 38, respectively, or (iii) a complementary strand of (i) or (ii); or allelic variants and subsequences thereof (Sambrook et al., 1989, supra), as defined herein.

The present invention also relates to isolated polynucleotides encoding a polypeptide of the present invention, (i) which hybridize under low stringency conditions, more preferably medium stringency conditions, more preferably medium-high stringency conditions, even more preferably high stringency conditions, and most preferably very high stringency conditions with nucleotides 55 to 2189 of SEQ ID NO: 4 or nucleotides 55 to 2182 of SEQ ID NO: 39, respectively, or (ii) which hybridize under medium stringency conditions, more preferably medium-high stringency conditions, even more preferably high stringency conditions, and most preferably very high stringency conditions with nucleotides the cDNA sequence contained in nucleotides 55 to 1725 of SEQ ID NO: 6 or nucleotides 55 to 1749 of SEQ ID NO: 41, or (iii) a complementary strand of (i) or (ii); or allelic variants and subsequences thereof (Sambrook et al., 1989, supra), as defined herein.

The present invention also relates to isolated polynucleotides encoding a polypeptide of the present invention, (i) which hybridize under low stringency conditions, more preferably medium stringency conditions, more preferably medium-high stringency conditions, even more preferably high stringency conditions, and most preferably very high stringency conditions with nucleotides 117 to 2249 of SEQ ID NO: 23, or (ii) which hybridize under low stringency conditions, preferably medium stringency conditions, more preferably medium-high stringency conditions, even more preferably high stringency conditions, and most preferably very high stringency conditions with nucleotides the cDNA sequence contained in nucleotides 52 to 1719 of SEQ ID NO: 25 or nucleotides 52 to 1620 of SEQ ID NO: 42, respectively, or (iii) a complementary strand of (i) or (ii); or allelic variants and subsequences thereof (Sambrook et al., 1989, supra), as defined herein.

The present invention also relates to isolated polynucleotides obtained by (a) hybridizing a population of DNA under low, medium, medium-high, high, or very high stringency conditions with (i) nucleotides 55 to 2166 of SEQ ID NO: 1 or nucleotides 55 to 2166 of SEQ ID NO: 36, respectively, or (ii) hybridizing a population of DNA under medium, medium-high, high, or very high stringency conditions with the cDNA sequence contained in nucleotides 55 to 1725 of SEQ ID NO: 3 or nucleotides 55 to 1737 of SEQ ID NO: 38, respectively, or (iii) a complementary strand of (i) or (ii); and (b) isolating the hybridizing polynucleotide, which encodes a polypeptide having glucoamylase activity.

The present invention also relates to isolated polynucleotides obtained by (a) hybridizing a population of DNA under low, medium, medium-high, high, or very high stringency conditions with (i) nucleotides 55 to 2189 of SEQ ID NO: 4 or nucleotides 55 to 2182 of SEQ ID NO: 39, respectively, or (ii) hybridizing a population of DNA under medium, medium-high, high, or very high stringency conditions with the cDNA sequence contained in nucleotides 55 to 1725 of SEQ ID NO: 6 or nucleotides 55 to 1749 of SEQ ID NO: 41, respectively, or (iii) a complementary strand of (i) or (ii); and (b) isolating the hybridizing polynucleotide, which encodes a polypeptide having glucoamylase activity.

The present invention also relates to isolated polynucleotides obtained by (a) hybridizing a population of DNA under low, medium, medium-high, high, or very high stringency conditions with (i) nucleotides 117 to 2249 of SEQ ID NO: 23, or (ii) hybridizing a population of DNA under medium, medium-high, high, or very high stringency conditions with the cDNA sequence contained in nucleotides 52 to 1719 of SEQ ID NO: 25 or nucleotides 52 to 1620 of SEQ ID NO: 42, respectively, or (iii) a complementary strand of (i) or (ii); and (b) isolating the hybridizing polynucleotide, which encodes a polypeptide having glucoamylase activity.

Nucleic Acid Constructs

The present invention also relates to nucleic acid constructs comprising an isolated polynucleotide of the present invention operably linked to one or more control sequences which direct the expression of the coding sequence in a suitable host cell under conditions compatible with the control sequences.

An isolated polynucleotide encoding a polypeptide of the present invention may be manipulated in a variety of ways to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well known in the art.

The control sequence may be an appropriate promoter sequence, a nucleotide sequence which is recognized by a host cell for expression of a polynucleotide encoding a polypeptide of the present invention. The promoter sequence contains transcriptional control sequences which mediate the expression of the polypeptide. The promoter may be any nucleotide sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* glucoamylase (WO 00/56900), *Fusarium venenatum* Daria (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionine (CUP1), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleotide sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleotide sequence encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleic acids and control sequences described above may be joined together to produce a recombinant expression vector which may include one or more convenient restriction sites to allow for insertion or substitution of the nucleotide sequence encoding the polypeptide at such sites. Alternatively, a nucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like.

Examples of suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity with the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication which functions in a cell. The term "origin of replication" or "plasmid replicator" is defined herein as a nucleotide sequence that enables a plasmid or vector to replicate in vivo.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98:61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into the host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention, which are advantageously used in the recombinant production of the polypeptides. A vector comprising a polynucleotide of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a eukaryote, such as a mammalian, insect, plant, or fungal cell.

In a preferred aspect, the host cell is a fungal cell. "Fungi" as used herein includes the phyla *Ascomycota, Basidiomycota, Chytridiomycota,* and *Zygomycota* (as defined by Hawksworth et al., In, *Ainsworth and Bisby's Dictionary of The Fungi,* 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, F. A., Passmore, S. M., and Davenport, R. R., eds, *Soc. App. Bacteriol. Symposium Series No.* 9, 1980).

In an even more preferred aspect, the yeast host cell is a *Candida, Hansenula, Kluyveromyces, Pichia, Saccharomyces, Schizosaccharomyces,* or *Yarrowia* cell.

In a most preferred aspect, the yeast host cell is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred aspect, the yeast host cell is a *Kluyveromyces lactis* cell. In another most preferred aspect, the yeast host cell is a *Yarrowia lipolytica* cell.

In another more preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred aspect, the filamentous fungal host cell is an *Acremonium, Aspergillus, Aureobasidium, Bjerkandera, Ceriporiopsis, Coprinus, Coriolus, Cryptococcus, Filobasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

In a most preferred aspect, the filamentous fungal host cell is an *Aspergillus awamori, Aspergillus fumigatus, Aspergillus foetidus, Aspergillus japonicus, Aspergillus nidulans, Aspergillus niger* or *Aspergillus oryzae* cell. In another most preferred aspect, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides,* or *Fusarium venenatum* cell. In another most preferred aspect, the filamentous fungal host cell is a *Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa,* or *Ceriporiopsis subvermispora, Coprinus cinereus, Coriolus hirsutus, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* strain cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology, Volume* 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods for producing a polypeptide of the present invention, comprising (a) cultivating a cell, which in its wild-type form is capable of producing the polypeptide, under conditions conducive for production of the polypeptide; and (b) recovering the polypeptide. Preferably, the cell is of the genus *Trametes, Pachykytospora,* or *Leucopaxillus,* and more preferably *Trametes cingulata, Pachykytospora papyracea,* or *Leucopaxillus giganteus*.

The present invention also relates to methods for producing a polypeptide of the present invention, comprising (a) cultivating a host cell under conditions conducive for production of the polypeptide; and (b) recovering the polypeptide.

The present invention also relates to methods for producing a polypeptide of the present invention, comprising (a) cultivating a host cell under conditions conducive for production of the polypeptide, wherein the host cell comprises a nucleotide sequence having the mature polypeptide coding region of SEQ ID NO: 1, 3, 4, 6, 23, 25, 36, 38, 39, 41, or 42, respectively, wherein the nucleotide sequence encodes a polypeptide which consists of amino acids 1 to 556 of SEQ ID NO: 2 or amino acids 1 to 561 of SEQ ID NO: 37, respectively; or amino acids 1 to 575 of SEQ ID NO: 5 or amino acids 1 to 565 of SEQ ID NO: 40, respectively; or amino acids 1 to 556 of SEQ ID NO: 26 or amino acids 1 to 548 of SEQ ID NO: 24 or amino acids 1 to 523 of SEQ ID NO: 43, respectively, and (b) recovering the polypeptide.

In the production methods of the present invention, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989).

Plants

The present invention also relates to a transgenic plant, plant part, or plant cell which has been transformed with a nucleotide sequence encoding a polypeptide having glucoamylase activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, *Poa*), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilisation of the invention are also considered plant parts, e.g., embryos, endosperms, aleurone and seeds coats.

Also included within the scope of the present invention are the progeny of such plants, plant parts, and plant cells.

The transgenic plant or plant cell expressing a polypeptide of the present invention may be constructed in accordance with methods known in the art. In short, the plant or plant cell is constructed by incorporating one or more expression constructs encoding a polypeptide of the present invention into the plant host genome and propagating the resulting modified plant or plant cell into a transgenic plant or plant cell.

The expression construct is conveniently a nucleic acid construct which comprises a polynucleotide encoding a polypeptide of the present invention operably linked with appropriate regulatory sequences required for expression of the nucleotide sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, and the rice actin 1 promoter may be used (Franck et al., 1980, *Cell* 21: 285-294, Christensen et al., 1992, *Plant Mo. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards & Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant and Cell Physiology* 39: 885-889), a *Vicia faba* promoter from the legumin B4 and the unknown seed protein gene from *Vicia faba* (Conrad et al., 1998, *Journal of Plant Physiology* 152: 708-711), a promoter from a seed oil body protein (Chen et al., 1998, *Plant and Cell Physiology* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991-1000, the *chlorella* virus adenine methyltransferase gene promoter (Mitra and Higgins, 1994, *Plant Molecular Biology* 26: 85-93), or the aldP gene promoter from rice (Kagaya et al., 1995, *Molecular and General Genetics* 248: 668-674), or a wound inducible promoter such as the potato pin2 promoter (Xu et al., 1993, *Plant Molecular Biology* 22: 573-588). Likewise, the promoter may inducible by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide of the present invention in the plant. For instance, the promoter enhancer element may be an intron which is placed between the promoter and the nucleotide sequence encoding a polypeptide of the present invention. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15-38) and can also be used for transforming monocots, although other transformation methods are often used for these plants. Presently, the method of choice for generating transgenic monocots is particle bombardment (microscopic gold or tungsten particles coated with the transforming DNA) of embryonic calli or developing embryos (Christou, 1992, *Plant Journal* 2: 275-281; Shimamoto, 1994, *Current Opinion Biotechnology* 5: 158-162; Vasil et al., 1992, *Bio/Technology* 10: 667-674). An alternative method for transformation of monocots is based on protoplast transformation as described by Omirulleh et al., 1993, *Plant Molecular Biology* 21: 415-428.

Following transformation, the transformants having incorporated the expression construct are selected and regenerated into whole plants according to methods well-known in the art. Often the transformation procedure is designed for the selective elimination of selection genes either during regeneration or in the following generations by using, for example, co-transformation with two separate T-DNA constructs or site specific excision of the selection gene by a specific recombinase.

The present invention also relates to methods for producing a polypeptide of the present invention comprising (a) cultivating a transgenic plant or a plant cell comprising a polynucleotide encoding a polypeptide having glucoamylase activity of the present invention under conditions conducive for production of the polypeptide; and (b) recovering the polypeptide.

Compositions

The present invention also relates to compositions comprising a polypeptide of the present invention. Preferably, the compositions are enriched in such a polypeptide. The term "enriched" indicates that the glucoamylase activity of the composition has been increased, e.g., by an enrichment factor of 1.1.

The composition may comprise a polypeptide of the present invention as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be produced, for example, by a microorganism belonging to the genus *Aspergillus*, preferably *Aspergillus aculeatus*, *Aspergillus awamori*, *Aspergillus fumigatus*, *Aspergillus foetidus*, *Aspergillus japonicus*, *Aspergillus nidulans*, *Aspergillus niger*, or *Aspergillus oryzae*; *Fusarium*, preferably *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sulphureum*, *Fusarium toruloseum*, *Fusarium trichothecioides*, or *Fusarium venenatum*; *Humicola*, preferably *Humicola insolens* or *Humicola lanuginosa*; or *Trichoderma*, preferably *Trichoderma harzianum*, *Trichoderma koningii*, *Trichoderma longibrachiatum*, *Trichoderma reesei*, or *Trichoderma viride*.

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Combination of Glucoamylase and Acid Alpha-Amylase

According to this aspect of the invention a glucoamylase of the invention may be combined with an acid alpha-amylase in a ratio of between 0.3 and 5.0 AFAU/AGU. More preferably the ratio between acid alpha-amylase activity and glucoamylase activity is at least 0.35, at least 0.40, at least 0.50, at least 0.60, at least 0.7, at least 0.8, at least 0.9, at least 1.0, at least 1.1, at least 1.2, at least 1.3, at least 1.4, at least 1.5, at least 1.6, at least 1.7, at least 1.8, at least 1.85, or even at least 1.9 AFAU/AGU. However, the ratio between acid alpha-amylase activity and glucoamylase activity should preferably be less than 4.5, less than 4.0, less than 3.5, less than 3.0, less than 2.5, or even less than 2.25 AFAU/AGU. In AUU/AGI the activities of acid alpha-amylase and glucoamylase are preferably present in a ratio of between 0.4 and 6.5 AUU/AGI. More preferably the ratio between acid alpha-amylase activity and glucoamylase activity is at least 0.45, at least 0.50, at least 0.60, at least 0.7, at least 0.8, at least 0.9, at least 1.0, at least 1.1, at least 1.2, at least 1.3, at least 1.4, at least 1.5, at least 1.6, at least 1.7, at least 1.8, at least 1.9, at least 2.0, at least 2.1, at least 2.2, at least 2.3, at least 2.4, or even at least 2.5 AUU/AGI. However, the ratio between acid alpha-amylase activity and glucoamylase activity is preferably less than 6.0, less than 5.5, less than 4.5, less than 4.0, less than 3.5, or even less than 3.0 AUU/AGI.

Above composition is suitable for use in a starch conversion process mentioned below for producing syrup and fermentation products such as ethanol.

Examples are given below of preferred uses of the polypeptide compositions of the invention. The dosage of the polypeptide composition of the invention and other conditions under which the composition is used may be determined on the basis of methods known in the art.

Combination of *Trametes cingulata* Glucoamylase with Another Glucoamylase and an Acid Alpha-Amylase The *Trametes cingulata* glucoamylase of the invention have been found to have a 4-7 fold higher alpha-1,6-debranching activity than other glucoamylases, such as *Athelia rolfsii*, *Aspergillus niger* and *Talaromyces emersonii* (see Example 13).

Therefore, according to the invention the *Trametes cingulata* glucoamylase may be combined with acid alpha-amylase and further another glucoamylase. Such combination of enzymes would be suitable in processes comprises starch conversion, include ethanol production, including one step fermentation processes.

The alpha-amylase may be any alpha-amylase. In a preferred embodiment the alpha-amylase is any of those listed in the "Alpha-Amylase"-section below. In a preferred embodiment the alpha-amylase is a fungal alpha-amylase, especially those disclosed below in the "Fungal Alpha-Amylases"-section, especially the *Aspergillus kawachii* alpha-amylase. Preferred are also hybrid alpha-amylases disclosed below in the "Fungal hybrid alpha-amylase"-section below, including hybrids disclosed in U.S. Patent Publication no. 2005/0054071 (hybrids listed in Table 3 is especially contemplated), and further the hybrids disclosed in co-pending U.S. application No. 60/638,614, including especially the Fungamyl variant with catalytic domain JA118 and *Athelia rolfsii* SBD (SEQ ID NO: 28 herein and SEQ ID NO: 100 in U.S. 60/638,614); *Rhizomucor pusillus* alpha-amylase with *Athelia rolfsii* AMG linker and SBD (SEQ ID NO: 29 herein and SEQ ID NO: 101 in U.S. application No. 60/638,614); and *Meripilus giganteus* alpha-amylase with *Athelia rolfsii* glucoamylase linker and SBD (SEQ ID NO: 30 herein and SEQ ID NO: 102 in U.S. application No. 60/638,614).

The glucoamylase may be any glucoamylase, including glucoamylases of fungal or bacterial origin selected from the group consisting of *Aspergillus* glucoamylases, in particular *A. niger* G1 or G2 glucoamylase (Boel et al., 1984, *EMBO J.* 3 (5): 1097-1102), or variants thereof, such as disclosed in WO 92/00381, WO 00/04136 add WO 01/04273 (from Novozymes, Denmark); the *A. awamori* glucoamylase (WO 84/02921), *A. oryzae* (*Agric. Biol. Chem.*, 1991, 55 (4): 941-949), or variants or fragments thereof. Other *Aspergillus* glucoamylase variants include variants to enhance the thermal stability: G137A and G139A (Chen et al., 1996, *Prot. Eng.* 9: 499-505); D257E and D293E/Q (Chen et al., 1995, *Prot. Engng.* 8: 575-582); N182 (Chen et al., 1994, *Biochem. J.* 301: 275-281); disulphide bonds, A246C (Fierobe et al., 1996, *Biochemistry*, 35: 8698-8704; and introduction of Pro residues in position A435 and S436 (Li et al., 1997, *Protein Engng.* 10: 1199-1204. Other glucoamylases include *Corticium rolfsii* glucoamylase (U.S. Pat. No. 4,727,046) also referred to as *Athelia rolfsii*, *Talaromyces* glucoamylases, in particular, derived from *Talaromyces emersonii* (WO 99/28448), *Talaromyces leycettanus* (U.S. Pat. No. Re. 32,153), *Talaromyces duponti*, *Talaromyces thermophilus* (U.S. Pat. No. 4,587,215), *Rhizopus nivius* (e.g., the enzyme available from Shin Nihon Chemicals, Japan, under the trade-name "CU CONC"), *Humicola grisea* var. *thermoidea* (e.g., ATCC 16453, NRRL 15222, NRRL 15223, NRRL 15224, NRRL 15225).

Bacterial glucoamylases contemplated include glucoamylases from the genus *Clostridium*, in particular *C. thermoamylolyticum* (EP 135,138), and *C. thermohydrosulfuricum* (WO 86/01831).

Examples of commercially available compositions comprising other glucoamylase include AMG 200L; AMG 300 L; SAN™ SUPER, SAN™ EXTRA L, SPIRIZYME™ PLUS, SPIRIZYME™ FUEL, SPIRIZYME™ B4U and AMG™ E (from Novozymes A/S); OPTIDEX™ 300 (from Genencor Int.); AMIGASE™ and AMIGASE™ PLUS (from DSM); G-ZYME™ G900, G-ZYME™ and G990 ZR (from Genencor Int.).

In a specific embodiment the *Trametes cingulata* glucoamylase of the invention is combined with glucoamylase derived from one of *Aspergillus niger, Athea rolfsii,* or *Talaromyces emersonii* and the *Rhizomucor pusillus* alpha-amylase with *Athelia rolfsii* AMG linker and SBD (SEQ ID NO: 29 herein and SEQ ID NO: 101 in U.S. application No. 60/638, 614).

Uses

The present invention is also directed to process/methods for using the polypeptides having glucoamylase activity of the invention.

Uses according to the invention include starch conversion of starch to, e.g., syrup and fermentation products, including ethanol and beverages. Examples of processes where a glucoamylase of the invention may be used include the ones described in: WO 2004/081193, WO 2004/080923, WO 2003/66816, WO 2003/66826, and WO 92/20777 which are hereby all incorporated by reference.

Production of Fermentation Products

Processes for Producing Fermentation Products from Gelatinized Starch-Containing Material In this aspect the present invention relates to a process for producing a fermentation product, especially ethanol, from starch-containing material, which process includes a liquefaction step and separately or simultaneously performed saccharification and fermentation step(s).

The invention relates to a process for producing a fermentation product from starch-containing material comprising the steps of:

(a) liquefying starch-containing material in the presence of an alpha-amylase;

(b) saccharifying the liquefied material obtained in step (a) using a glucoamylase of the invention;

(c) fermenting the saccharified material using a fermenting organism.

The fermentation product, such as especially ethanol, may optionally be recovered after fermentation, e.g., by distillation. Suitable starch-containing starting materials are listed in the section "Starch-containing materials"-section below. Contemplated enzymes are listed in the "Enzymes"-section below. The fermentation is preferably carried out in the presence of yeast, preferably a strain of *Saccharomyces*. Suitable fermenting organisms are listed in the "Fermenting Organisms"-section below. In a preferred embodiment step (b) and (c) are carried out simultaneously (SSF process).

In a particular embodiment, the process of the invention further comprises, prior to the step (a), the steps of:

x) reducing the particle size of the starch-containing material, preferably by milling;

y) forming a slurry comprising the starch-containing material and water.

The aqueous slurry may contain from 10-40 wt-%, preferably 25-35 wt-% starch-containing material. The slurry is heated to above the gelatinization temperature and alpha-amylase, preferably bacterial and/or acid fungal alpha-amylase, may be added to initiate liquefaction (thinning). The slurry may in an embodiment be jet-cooked to further gelatinize the slurry before being subjected to an alpha-amylase in step (a) of the invention.

More specifically liquefaction may be carried out as a three-step hot slurry process. The slurry is heated to between 60-95° C., preferably 80-85° C., and alpha-amylase is added to initiate liquefaction (thinning). Then the slurry may be jet-cooked at a temperature between 95-140° C., preferably 105-125° C., for 1-15 minutes, preferably for 3-10 minutes, especially around 5 minutes. The slurry is cooled to 60-95° C. and more alpha-amylase is added to finalize hydrolysis (secondary liquefaction). The liquefaction process is usually carried out at pH 4.5-6.5, in particular at a pH between 5 and 6. Milled and liquefied whole grains are known as mash.

The saccharification in step (b) may be carried out using conditions well know in the art. For instance, a full saccharification process may lasts up to from about 24 to about 72 hours, however, it is common only to do a pre-saccharification of typically 40-90 minutes at a temperature between 30-65° C., typically about 60° C., followed by complete saccharification during fermentation in a simultaneous saccharification and fermentation process (SSF). Saccharification is typically carried out at temperatures from 30-65° C., typically around 60° C., and at a pH between 4 and 5, normally at about pH 4.5.

The most widely used process in ethanol production is the simultaneous saccharification and fermentation (SSF) process, in which there is no holding stage for the saccharification, meaning that fermenting organism, such as yeast, and enzyme(s) may be added together. When doing SSF it is common to introduce a pre-saccharification step at a temperature above 50° C., just prior to the fermentation.

In accordance with the present invention the fermentation step (c) includes, without limitation, fermentation processes used to produce alcohols (e.g., ethanol, methanol, butanol); organic acids (e.g., citric acid, acetic acid, itaconic acid, lactic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, B12, beta-carotene); and hormones. Preferred fermentation processes include alcohol fermentation processes, as are well known in the art. Preferred fermentation processes are anaerobic fermentation processes, as are well known in the art.

Processes for Producing Fermentation Products from Un-gelatinized Starch-Containing In this aspect the invention relates to processes for producing a fermentation product from starch-containing material without gelatinization of the starch-containing material. In one embodiment only a glucoamylase of the invention is used during saccharification and fermentation. According to the invention the desired fermentation product, such as ethanol, can be produced without liquefying the aqueous slurry containing the starch-containing material. In one embodiment a process of the invention includes saccharifying milled starch-containing material below the gelatinization temperature in the presence of a glucoamylase of the invention to produce sugars that can be fermented into the desired fermentation product by a suitable fermenting organism.

Examples 8 and 9 below disclose production of ethanol from un-gelatinized (uncooked) milled corn using glucoamylases of the invention derived from *Trametes cingulata* and

*Pachykytospora papyracea*. Both glucoamylases show significantly higher ethanol yields compared to corresponding processes carried out using glucoamylases derived from *Aspergillus niger* or *Talaromyces emersonii*, respectively.

Accordingly, in this aspect the invention relates to a process for producing a fermentation product from starch-containing material comprising:

(a) saccharifying starch-containing material with a glucoamylase having
  i) the sequence shown as amino acids 1 to 556 in SEQ ID NO: 2 or amino acids 1 to 561 in SEQ ID NO: 37, or a glucoamylase having at least 75% identity thereto, and/or
  ii) the sequence shown as amino acids 1 to 575 in SEQ ID NO: 5 or amino acids 1 to 565 in SEQ ID NO: 40, or a glucoamylase having at least 70% identity thereto, and/or
  iii) the sequence shown as amino acids 1 to 548 in SEQ ID NO: 24 or amino acids 1 to 556 in SEQ ID NO: 26 or amino acids 1 to 523 in SEQ ID NO: 43, or a glucoamylase having at least 60% identity thereto, at a temperature below the initial gelatinization temperature of said starch-containing material,
(b) fermenting using a fermenting organism.

Steps (a) and (b) of the process of the invention may be carried out sequentially or simultaneously.

The term "initial gelatinization temperature" means the lowest temperature at which gelatinization of the starch commences. Starch heated in water begins to gelatinize between 50° C. and 75° C.; the exact temperature of gelatinization depends on the specific starch, and can readily be determined by the skilled artisan. Thus, the initial gelatinization temperature may vary according to the plant species, to the particular variety of the plant species as well as with the growth conditions. In the context of this invention the initial gelatinization temperature of a given starch-containing material is the temperature at which birefringence is lost in 5% of the starch granules using the method described by Gorinstein and Lii, 1992, *Starch/Stärke* 44 (12): 461-466.

Before step (a) a slurry of starch-containing material, such as granular starch, having 20-55 wt. % dry solids, preferably 25-40 wt. % dry solids, more preferably 30-35% dry solids of starch-containing material may be prepared. The slurry may include water and/or process waters, such as stillage (backset), scrubber water, evaporator condensate or distillate, side stripper water from distillation, or other fermentation product plant process water. Because the process of the invention is carried out below the gelatinization temperature and thus no significant viscosity increase takes place, high levels of stillage may be used if desired. In an embodiment the aqueous slurry contains from about 1 to about 70 vol. % stillage, preferably 15-60 vol. % stillage, especially from about 30 to 50 vol. % stillage.

The starch-containing material may be prepared by reducing the particle size, preferably by milling, to 0.05 to 3.0 mm, preferably 0.1-0.5 mm. After being subjected to a process of the invention at least 85%, at least 86%, at least 87%, at least 88%, at least 89%, at least 90%, at least 91%, at least 92%, at least 93%, at least 94%, at least 95%, at least 96%, at least 97%, at least 98%, or preferably at least 99% of the dry solids of the starch-containing material is converted into a soluble starch hydrolysate.

The process of the invention is conducted at a temperature below the initial gelatinization temperature. Preferably the temperature at which step (a) is carried out is between 30-75° C., preferably between 45-60° C.

In a preferred embodiment step (a) and step (b) are carried out as a simultaneous saccharification and fermentation process. In such preferred embodiment the process is typically carried at a temperature between 28° C. and 36° C., such as between 29° C. and 35° C., such as between 30° C. and 34° C., such as around 32° C. According to the invention the temperature may be adjusted up or down during fermentation.

In an embodiment simultaneous saccharification and fermentation is carried out so that the sugar level, such as glucose level, is kept at a low level such as below 6 wt. %, preferably below about 3 wt. %, preferably below about 2 wt. %, more preferred below about 1 wt. %., even more preferred below about 0.5%, or even more preferred 0.25% wt. %, such as below about 0.1 wt. %. Such low levels of sugar can be accomplished by simply employing adjusted quantities of enzyme and fermenting organism. A skilled person in the art can easily determine which quantities of enzyme and fermenting organism to use. The employed quantities of enzyme and fermenting organism may also be selected to maintain low concentrations of maltose in the fermentation broth. For instance, the maltose level may be kept below about 0.5 wt. % or below about 0.2 wt. %.

The process of the invention may be carried out at a pH in the range between 3 and 7, preferably from pH 3.5 to 6, or more preferably from pH 4 to 5.

Starch-Containing Materials

Any suitable starch-containing starting material, including granular starch, may be used according to the present invention. The starting material is generally selected based on the desired fermentation product. Examples of starch-containing starting materials, suitable for use in a process of present invention, include tubers, roots, stems, whole grains, corns, cobs, wheat, barley, rye, milo, sago, cassava, tapioca, sorghum, rice peas, beans, or sweet potatoes, or mixtures thereof, or cereals, sugar-containing raw materials, such as molasses, fruit materials, sugar cane or sugar beet, potatoes, and cellulose-containing materials, such as wood or plant residues, or mixtures thereof. Contemplated are both waxy and non-waxy types of corn and barley.

The term "granular starch" means raw uncooked starch, i.e., starch in its natural form found in cereal, tubers or grains. Starch is formed within plant cells as tiny granules insoluble in water. When put in cold water, the starch granules may absorb a small amount of the liquid and swell. At temperatures up to 50° C. to 75° C. the swelling may be reversible. However, with higher temperatures an irreversible swelling called "gelatinization" begins. Granular starch to be processed may be a highly refined starch quality, preferably at least 90%, at least 95%, at least 97% or at least 99.5% pure or it may be a more crude starch containing material comprising milled whole grain including non-starch fractions such as germ residues and fibers. The raw material, such as whole grain, is milled in order to open up the structure and allowing for further processing. Two milling processes are preferred according to the invention: wet and dry milling. In dry milling whole kernels are milled and used. Wet milling gives a good separation of germ and meal (starch granules and protein) and is often applied at locations where the starch hydrolysate is used in production of syrups. Both dry and wet milling is well known in the art of starch processing and is equally contemplated for the process of the invention.

The starch-containing material is reduced in size, preferably by milling, in order to expose more surface area. In an embodiment the particle size is between 0.05 to 3.0 mm, preferably 0.1-0.5 mm, or so that at least 30%, preferably at least 50%, more preferably at least 70%, even more preferably at least 90% of the milled starch-containing material fit through a sieve with a 0.05 to 3.0 mm screen, preferably 0.1-0.5 mm screen.

Fermentation Products

The term "fermentation product" means a product produced by a process including a fermentation step using a fermenting organism. Fermentation products contemplated according to the invention include alcohols (e.g., ethanol, methanol, butanol); organic acids (e.g., citric acid, acetic acid, itaconic acid, lactic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, $B_{12}$, beta-carotene); and hormones. In a preferred embodiment the fermentation product is ethanol, e.g., fuel ethanol; drinking ethanol, i.e., potable neutral spirits; or industrial ethanol or products used in the consumable alcohol industry (e.g., beer and wine), dairy industry (e.g., fermented dairy products), leather industry and tobacco industry. Preferred beer types comprise ales, stouts, porters, lagers, bitters, malt liquors, happoushu, high-alcohol beer, low-alcohol beer, low-calorie beer or light beer. Preferred fermentation processes used include alcohol fermentation processes, as are well known in the art. Preferred fermentation processes are anaerobic fermentation processes, as are well known in the art.

Fermenting Organisms

"Fermenting organism" refers to any organism, including bacterial and fungal organisms, suitable for use in a fermentation process and capable of producing desired a fermentation product. Especially suitable fermenting organisms are able to ferment, i.e., convert, sugars, such as glucose or maltose, directly or indirectly into the desired fermentation product.

Examples of fermenting organisms include fungal organisms, such as yeast. Preferred yeast includes strains of *Saccharomyces* spp., in particular, *Saccharomyces cerevisiae*. Commercially available yeast include, e.g., Red Star™/Lesaffre Ethanol Red (available from Red Star/Lesaffre, USA) FALI (available from Fleischmann's Yeast, a division of Burns Philp Food Inc., USA), SUPERSTART (available from Alltech), GERT STRAND (available from Gert Strand AB, Sweden) and FERMIOL (available from DSM Specialties).

Enzymes

Glucoamylase

The glucoamylase is preferably a glucoamylase of the invention. However, as mentioned above a glucoamylase of the invention may also be combined with other glucoamylases.

The glucoamylase may added in an amount of 0.001 to 10 AGU/g DS, preferably from 0.01 to 5 AGU/g DS, such as around 0.1, 0.3, 0.5, 1 or 2 AGU/g DS, especially 0.1 to 0.5 AGU/g DS or 0.02-20 AGU/g DS, preferably 0.1-10 AGU/g DS.

Alpha-Amylase

The alpha-amylase may according to the invention be of any origin. Preferred are alpha-amylases of fungal or bacterial origin.

In a preferred embodiment the alpha-amylase is an acid alpha-amylase, e.g., fungal acid alpha-amylase or bacterial acid alpha-amylase. The term "acid alpha-amylase" means an alpha-amylase (E.C. 3.2.1.1) which added in an effective amount has activity optimum at a pH in the range of 3 to 7, preferably from 3.5 to 6, or more preferably from 4-5.

Bacterial Alpha-Amylases

According to the invention a bacterial alpha-amylase may preferably be derived from the genus *Bacillus*.

In a preferred embodiment the *Bacillus* alpha-amylase is derived from a strain of *B. licheniformis, B. amyloliquefaciens, B. subtilis* or *B. stearothermophilus*, but may also be derived from other *Bacillus* sp. Specific examples of contemplated alpha-amylases include the *Bacillus licheniformis* alpha-amylase (BLA) shown in SEQ ID NO: 4 in WO 99/19467, the *Bacillus amyloliquefaciens* alpha-amylase (BAN) shown in SEQ ID NO: 5 in WO 99/19467, and the *Bacillus stearothermophilus* alpha-amylase (BSG) shown in SEQ ID NO: 3 in WO 99/19467. In an embodiment of the invention the alpha-amylase is an enzyme having a degree of identity of at least 60%, preferably at least 70%, more preferred at least 80%, even more preferred at least 90%, such as at least 95%, at least 96%, at least 97%, at least 98% or at least 99% identity to any of the sequences shown as SEQ ID NOS: 1, 2, 3, 4, or 5, respectively, in WO 99/19467.

The *Bacillus* alpha-amylase may also be a variant and/or hybrid, especially one described in any of WO 96/23873, WO 96/23874, WO 97/41213, WO 99/19467, WO 00/60059, and WO 02/10355 (all documents hereby incorporated by reference). Specifically contemplated alpha-amylase variants are disclosed in U.S. Pat. Nos. 6,093,562, 6,297,038 or U.S. Pat. No. 6,187,576 (hereby incorporated by reference) and include *Bacillus stearothermophilus* alpha-amylase (BSG alpha-amylase) variants having a deletion of one or two amino acids in position 179 to 182, preferably a double deletion disclosed in WO 1996/023873—see e.g., page 20, lines 1-10 (hereby incorporated by reference), preferably corresponding to delta (181-182) compared to the wild-type BSG alpha-amylase amino acid sequence set forth in SEQ ID NO: 3 disclosed in WO 99/19467 or deletion of amino acids 179 and 180 using SEQ ID NO: 3 in WO 99/19467 for numbering (which reference is hereby incorporated by reference). Even more preferred are *Bacillus* alpha-amylases, especially *Bacillus stearothermophilus* alpha-amylase, which have a double deletion corresponding to delta (181-182) and further comprise a N193F substitution (also denoted 1181*+G182*+N193F) compared to the wild-type BSG alpha-amylase amino acid sequence set forth in SEQ ID NO: 3 disclosed in WO 99/19467.

The alpha-amylase may also be a maltogenic alpha-amylase. A "maltogenic alpha-amylase" (glucan 1,4-alpha-maltohydrolase, E.C. 3.2.1.133) is able to hydrolyze amylose and amylopectin to maltose in the alpha-configuration. A maltogenic alpha-amylase from *Bacillus stearothermophilus* strain NCIB 11837 is commercially available from Novozymes A/S, Denmark. The maltogenic alpha-amylase is described in U.S. Pat. Nos. 4,598,048, 4,604,355 and 6,162,628, which are hereby incorporated by reference.

Bacterial Hybrid Alpha-Amylases

A hybrid alpha-amylase specifically contemplated comprises 445 C-terminal amino acid residues of the *Bacillus licheniformis* alpha-amylase (shown as SEQ ID NO: 4 in WO 99/19467) and the 37 N-terminal amino acid residues of the alpha-amylase derived from *Bacillus amyloliquefaciens* (shown as SEQ ID NO: 3 in WO 99/194676), with one or more, especially all, of the following substitutions:

G48A+T49I+G107A+H156Y+A181T+N190F+I201F+A209V+Q264S (using the *Bacillus licheniformis* numbering). Also preferred are variants having one or more of the following mutations (or corresponding mutations in other *Bacillus* alpha-amylase backbones): H154Y, A181T, N190F, A209V and Q264S and/or deletion of two residues between positions 176 and 179, preferably deletion of E178 and G179 (using the SEQ ID NO: 5 numbering of WO 99/19467).

The bacterial alpha-amylase may be added in amounts as are well-known in the art. When measured in KNU units (described below in the "Materials & Methods"-section) the alpha-amylase activity is preferably present in an amount of 0.5-5,000 NU/g of DS, in an amount of 1-500 NU/g of DS, or more preferably in an amount of 5-1,000 NU/g of DS, such as 10-100 NU/g DS.

Fungal Alpha-Amylases

Fungal acid alpha-amylases include acid alpha-amylases derived from a strain of the genus *Aspergillus*, such as *Aspergillus oryzae, Aspergillus niger, Aspergillus kawachii* alpha-amylases.

A preferred acid fungal alpha-amylase is a Fungamyl-like alpha-amylase which is preferably derived from a strain of *Aspergillus oryzae*. In the present disclosure, the term "Fungamyl-like alpha-amylase" indicates an alpha-amylase which exhibits a high identity, i.e., more than 70%, more than 75%, more than 80%, more than 85% more than 90%, more than 95%, more than 96%, more than 97%, more than 98%, more than 99% or even 100% identity to the mature part of the amino acid sequence shown in SEQ ID NO: 10 in WO 96/23874.

Another preferred acid alpha-amylase is derived from a strain *Aspergillus niger*. In a preferred embodiment the acid fungal alpha-amylase is the one from *A. niger* disclosed as "AMYA_ASPNG" in the Swiss-prot/TeEMBL database under the primary accession no. P56271 and described in more detail in WO 89/01969 (Example 3). The acid *Aspergillus niger* acid alpha-amylase is also shown as SEQ ID NO: 1 in WO 2004/080923 (Novozymes) which is hereby incorporated by reference. Also variants of said acid fungal amylase having at least 70% identity, such as at least 80% or even at least 90% identity, such as at least 95%, at least 96%, at least 97%, at least 98%, or at least 99% identity to SEQ ID NO: 1 in WO 2004/080923 are contemplated. A suitable commercially available acid fungal alpha-amylase derived from *Aspergillus niger* is SP288 (available from Novozymes A/S, Denmark).

In a preferred embodiment the alpha-amylase is derived from *Aspergillus kawachii* and disclosed by Kaneko et al., 1996, *J. Ferment. Bioeng.* 81: 292-298, "Molecular-cloning and determination of the nucleotide-sequence of a gene encoding an acid-stable alpha-amylase from *Aspergillus kawachii*"; and further as EMBL:#AB008370.

The fungal acid alpha-amylase may also be a wild-type enzyme comprising a carbohydrate-binding module (CBM) and an alpha-amylase catalytic domain (i.e., a none-hybrid), or a variant thereof. In an embodiment the wild-type acid alpha-amylase is derived from a strain of *Aspergillus kawachii*.

Fungal Hybrid Alpha-Amylases

In a preferred embodiment the fungal acid alpha-amylase is a hybrid alpha-amylase. Preferred examples of fungal hybrid alpha-amylases include the ones disclosed in WO 2005/003311 or U.S. Patent Publication no. 2005/0054071 (Novozymes) or U.S. patent application No. 60/638,614 (Novozymes) which is hereby incorporated by reference. A hybrid alpha-amylase may comprise an alpha-amylase catalytic domain (CD) and a carbohydrate-binding domain/module (CBM) and optional a linker.

Specific examples of contemplated hybrid alpha-amylases include those disclosed in U.S. patent application No. 60/638,614 including Fungamyl variant with catalytic domain JA118 and *Athelia rolfsii* SBD (SEQ ID NO: 28 herein and SEQ ID NO: 100 in U.S. application No. 60/638,614), *Rhizomucor pusillus* alpha-amylase with *Athelia rolfsii* AMG linker and SBD (SEQ ID NO: 29 herein and SEQ ID NO: 101 in U.S. application No. 60/638,614) and *Meripilus giganteus* alpha-amylase with *Athelia rolfsii* glucoamylase linker and SBD (SEQ ID NO: 30 herein and SEQ ID NO: 102 in U.S. application No. 60/638,614).

Other specific examples of contemplated hybrid alpha-amylases include those disclosed in U.S. Patent Application Publication no. 2005/0054071, including those disclosed in Table 3 on page 15, such as *Aspergillus niger* alpha-amylase with *Aspergillus kawachii* linker and starch binding domain.

Commercial Alpha-Amylase Products

Preferred commercial compositions comprising alpha-amylase include MYCOLASE from DSM (Gist Brocades), BAN™, TERMAMYL™ SC, FUNGAMYL™, LIQUOZYME™ X and SAN™ SUPER, SAN™ EXTRA L (Novozymes A/S) and CLARASE™ L-40,000, DEX-LO™, SPEZYME™ FRED, SPEZYME™ AA, and SPEZYME™ DELTA AA (Genencor Int.), and the acid fungal alpha-amylase sold under the trade name SP288 (available from Novozymes A/S, Denmark).

An acid alpha-amylases may according to the invention be added in an amount of 0.1 to 10 AFAU/g DS, preferably 0.10 to 5 AFAU/g DS, especially 0.3 to 2 AFAU/g DS.

Production of Syrup

The present invention also provides a process of using a glucoamylase of the invention for producing syrup, such as glucose and the like, from starch-containing material. Suitable starting materials are exemplified in the "Starch-containing materials"-section above. Generally, the process comprises the steps of partially hydrolyzing starch-containing material (liquefaction) in the presence of alpha-amylase and then further saccharifying the release of glucose from the non-reducing ends of the starch or related oligo- and polysaccharide molecules in the presence of glucoamylase of the invention.

Liquefaction and saccharification may be carried our as described above for fermentation product production.

The glucoamylase of the invention may also be used in immobilized form. This is suitable and often used for producing specialty syrups, such as maltose syrups, and further for the raffinate stream of oligosaccharides in connection with the production of fructose syrups, e.g., high fructose syrup (HFS).

Consequently, this aspect of the invention relates to a process of producing syrup from starch-containing material, comprising (a) liquefying starch-containing material in the presence of an alpha-amylase, (b) saccharifying the material obtained in step (a) using a glucoamylase of the invention.

A syrup may be recovered from the saccharified material obtained in step (b).

Details on suitable conditions can be found above.

Brewing

A glucoamylase of the invention can also be used in a brewing process. The glucoamylases of the invention is added in effective amounts which can be easily determined by the skilled person in the art. For instance, in the production of "low carb" or super attenuated beers, a higher proportion of alcohol and a lower amount of residual dextrin are desired. These beers are formulated using exogenous enzymes compositions comprising enzyme activities capable of debranching the limit dextrins. A glucoamylase of the invention, preferably *Trametes cingulata*, may be applied to reduce the content of limit dextrins as well as hydrolyzing the alpha-1,4 bonds.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and de-scribed herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties. The present invention is further described by the following examples which should not be construed as limiting the scope of the invention.

Materials & Methods

Glucoamylases:

Glucoamylase derived from *Trametes cingulata* disclosed in SEQ ID NO: 2 and available from Novozymes A/S.

Glucoamylase derived from *Pachykytospora papyraceae* disclosed in SEQ ID NO: 5 and available from Novozymes A/S.

Glucoamylase derived from *Leucopaxillus giganteus* disclosed in SEQ ID NO: 24 and available from Novozymes A/S.

Glucoamylase derived from *Aspergillus niger* disclosed in Boel et al., 1984, EMBO J. 3(5): 1097-1102 and available from Novozymes A/S.

Glucoamylase derived from *Talaromyces emersonii* disclosed in WO 99/28448 and available from Novozymes A/S.

Enzymes for DNA manipulations (e.g., restriction endonucleases, ligases etc.) are obtainable from New England Biolabs, Inc. and were used according to the manufacturer's instructions.

Alpha-Amylase:

Hybrid Alpha-Amylase A: *Rhizomucor pusillus* alpha-amylase with *Athelia rolfsii* glucoamylase linker and SBD disclosed in U.S. patent application No. 60/638,614 and SEQ ID NO: 29.

Yeast: Red Star™ available from Red Star/Lesaffre, USA

Microbial Strains

*E. coli* DH12alpha (GIBCO BRL, Life Technologies, USA)

*Aspergillus oryzae* IFO 4177 is available from Institute for Fermentation, Osaka (IFO) Culture Collection of Microorganisms, 17-85, Juso-honmachi, 2-chome, Yodogawa-ku, Osaka 532-8686, Japan.

*Aspergillus oryzae* BECh-2 is described in WO 2000/39322 (Novozymes). It is a mutant of JaL228 (described in WO 98/12300) which is a mutant of IFO 4177.

*Aspergillus niger* strain Mbin119 is described in WO 2004/090155 (see Example 12).

Other Materials

Pullulan available from Wako Pure Chemical (Japan).

Deposit of Biological Material

The following biological material has been deposited under the terms of the Budapest Treaty at Deutshe Sammmlung von Microorganismen and Zellkulturen GmbH (DSMZ), Mascheroder Weg 1b, D-38124 Braunschweig DE, and given the following accession number:

| Deposit | Accession Number | Date of Deposit |
|---|---|---|
| *Escherichia coli* NN049798 | DSM 17106 | 2 Feb. 2005 |
| *Escherichia coli* NN049797 | DSM 17105 | 2 Feb. 2005 |

The strain has been deposited under conditions that assure that access to the culture will be available during the pendency of this patent application to one determined by the Commissioner of Patents and Trademarks to be entitled thereto under 37 C.F.R. §1.14 and 35 U.S.C. §122. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

Media and Reagents:

Chemicals used as buffers and substrates were commercial products of at least reagent grade.

PDA2: 39 g/L Potato Dextrose Agar, 20 g/L agar, 50 ml/L glycerol

Cove: 342.3 g/L Sucrose, 20 ml/L COVE salt solution, 10 mM Acetamide, 30 g/L noble agar.

Cove salt solution: per liter 26 g KCl, 26 g $MgSO_4$-7aq, 76 g $KH_2PO_4$, 50 ml Cove trace metals.

Cove trace metals: per liter 0.04 g NaB4O7-10aq, 0.4 g CuSO4-5aq, 1.2 g $FeSO_4$-7aq, 0.7 g $MnSO_4$-aq, 0.7 g $Na_2MoO_2$-2aq, 0.7 g $ZnSO_4$-7aq.

YPG: 4 g/L Yeast extract, 1 g/L KH2PO4, 0.5 g/L $MgSO_4$-7aq, 5 g/L Glucose, pH 6.0.

STC: 0.8 M Sorbitol, 25 mM Tris pH 8, 25 mM $CaCl_2$.

STPC: 40% PEG4000 in STC buffer.

Cove top agarose: 342.3 g/L Sucrose, 20 ml/L COVE salt solution, 10 mM Acetamide, 10 g/L low melt agarose.

MS-9: per liter 30 g soybean powder, 20 g glycerol, pH 6.0.

MDU-pH5: per liter 45 g maltose-1aq, 7 g yeast extract, 12 g $KH_2PO_4$, 1 g $MgSO_4$-7aq, 2 g $K_2SO_4$, 0.5 ml AMG trace metal solution and 25 g 2-morpholinoethanesulfonic acid, pH 5.0.

Methods

Unless otherwise stated, DNA manipulations and transformations were performed using standard methods of molecular biology as described in Sambrook et al., 1989, Molecular cloning: A laboratory manual, Cold Spring Harbor lab., Cold Spring Harbor, N.Y.; Ausubel, F. M. et al. (eds.) "Current protocols in Molecular Biology", John Wiley and Sons, 1995; Harwood, C. R., and Cutting, S. M. (eds.) "Molecular Biological Methods for *Bacillus*". John Wiley and Sons, 1990.

Glucoamylase Activity

Glucoamylase activity may be measured in AGI units or in Glucoamylase Units (AGU).

Glucoamylase Activity (AGI)

Glucoamylase (equivalent to amyloglucosidase) converts starch into glucose. The amount of glucose is determined here by the glucose oxidase method for the activity determination. The method described in the section 76-11 Starch—Glucoamylase Method with Subsequent Measurement of Glucose with Glucose Oxidase in "Approved methods of the American Association of Cereal Chemists". Vol. 1-2 AACC, from American Association of Cereal Chemists, (2000); ISBN: 1-891127-12-8.

One glucoamylase unit (AGI) is the quantity of enzyme which will form 1 micro mole of glucose per minute under the standard conditions of the method.

Standard Conditions/Reaction Conditions:

| Substrate: | Soluble starch, concentration approx. 16 g dry matter/L. |
|---|---|
| Buffer: | Acetate, approx. 0.04 M, pH = 4.3 |
| pH: | 4.3 |
| Incubation temperature: | 60° C. |
| Reaction time: | 15 minutes |
| Termination of the reaction: | NaOH to a concentration of approximately 0.2 g/L (pH ~9) |
| Enzyme concentration: | 0.15-0.55 AAU/mL. |

The starch should be Lintner starch, which is a thin-boiling starch used in the laboratory as colorimetric indicator. Lintner starch is obtained by dilute hydrochloric acid treatment of native starch so that it retains the ability to color blue with iodine.

Glucoamylase Activity (AGU)

The Novo Glucoamylase Unit (AGU) is defined as the amount of enzyme, which hydrolyzes 1 micromole maltose per minute under the standard conditions 37° C., pH 4.3, substrate: maltose 23.2 mM, buffer: acetate 0.1 M, reaction time 5 minutes.

An autoanalyzer system may be used. Mutarotase is added to the glucose dehydrogenase reagent so that any alpha-D-glucose present is turned into beta-D-glucose. Glucose dehydrogenase reacts specifically with beta-D-glucose in the reaction mentioned above, forming NADH which is determined using a photometer at 340 nm as a measure of the original glucose concentration.

| AMG incubation: | |
|---|---|
| Substrate: | maltose 23.2 mM |
| Buffer: | acetate 0.1 M |
| pH: | 4.30 ± 0.05 |
| Incubation temperature: | 37° C. ± 1 |
| Reaction time: | 5 minutes |
| Enzyme working range: | 0.5-4.0 AGU/mL |

| Color reaction: | |
|---|---|
| GlucDH: | 430 U/L |
| Mutarotase: | 9 U/L |
| NAD: | 0.21 mM |
| Buffer: | phosphate 0.12 M; 0.15 M NaCl |
| pH: | 7.60 ± 0.05 |
| Incubation temperature: | 37° C. ± 1 |
| Reaction time: | 5 minutes |
| Wavelength: | 340 nm |

A folder (EB-SM-0131.02/01) describing this analytical method in more detail is available on request from Novozymes A/S, Denmark, which folder is hereby included by reference.

Alpha-Amylase Activity (KNU)

The alpha-amylase activity may be determined using potato starch as substrate. This method is based on the breakdown of modified potato starch by the enzyme, and the reaction is followed by mixing samples of the starch/enzyme solution with an iodine solution. Initially, a blackish-blue color is formed, but during the break-down of the starch the blue color gets weaker and gradually turns into a reddish-brown, which is compared to a colored glass standard.

One Kilo Novo alpha amylase Unit (KNU) is defined as the amount of enzyme which, under standard conditions (i.e., at 37° C.+/−0.05; 0.0003 M $Ca^{2+}$; and pH 5.6) dextrinizes 5260 mg starch dry substance Merck Amylum solubile.

A folder EB-SM-0009.02/01 describing this analytical method in more detail is available upon request to Novozymes A/S, Denmark, which folder is hereby included by reference.

Acid Alpha-Amylase Activity

When used according to the present invention the activity of any acid alpha-amylase may be measured in AFAU (Acid Fungal Alpha-amylase Units). Alternatively activity of acid alpha-amylase may be measured in AAU (Acid Alpha-amylase Units).

Acid Alpha-Amylase Units (AAU)

The acid alpha-amylase activity can be measured in AAU (Acid Alpha-amylase Units), which is an absolute method. One Acid Amylase Unit (AAU) is the quantity of enzyme converting 1 g of starch (100% of dry matter) per hour under standardized conditions into a product having a transmission at 620 nm after reaction with an iodine solution of known strength equal to the one of a color reference.

Standard Conditions/Reaction Conditions:

| | |
|---|---|
| Substrate: | Soluble starch. Concentration approx. 20 g DS/L. |
| Buffer: | Citrate, approx. 0.13 M, pH = 4.2 |
| Iodine solution: | 40.176 g potassium iodide + 0.088 g iodine/L |
| City water | 15°-20° dH (German degree hardness) |
| pH: | 4.2 |
| Incubation temperature: | 30° C. |
| Reaction time: | 11 minutes |
| Wavelength: | 620 nm |
| Enzyme concentration: | 0.13-0.19 AAU/mL |
| Enzyme working range: | 0.13-0.19 AAU/mL |

The starch should be Lintner starch, which is a thin-boiling starch used in the laboratory as colorimetric indicator. Lintner starch is obtained by dilute hydrochloric acid treatment of native starch so that it retains the ability to color blue with iodine. Further details can be found in EP 0140410 B2, which disclosure is hereby included by reference.

Acid Alpha-Amylase Activity (AFAU)

Acid alpha-amylase activity may be measured in AFAU (Acid Fungal Alpha-amylase Units), which are determined relative to an enzyme standard. 1 AFAU is defined as the amount of enzyme which degrades 5.260 mg starch dry matter per hour under the below mentioned standard conditions.

Acid alpha-amylase, an endo-alpha-amylase (1,4-alpha-D-glucan-glucanohydrolase, E.C. 3.2.1.1) hydrolyzes alpha-1,4-glucosidic bonds in the inner regions of the starch molecule to form dextrins and oligosaccharides with different chain lengths. The intensity of color formed with iodine is directly proportional to the concentration of starch. Amylase activity is determined using reverse colorimetry as a reduction in the concentration of starch under the specified analytical conditions.

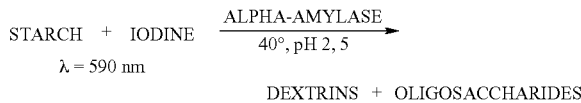

| blue/violet | t = 23 sec. | decoloration |
|---|---|---|

Standard Conditions/Reaction Conditions:

| | |
|---|---|
| Substrate: | Soluble starch, approx. 0.17 g/L |
| Buffer: | Citrate, approx. 0.03 M |
| Iodine (I2): | 0.03 g/L |
| $CaCl_2$: | 1.85 mM |
| pH: | 2.50 ± 0.05 |
| Incubation temperature: | 40° C. |
| Reaction time: | 23 seconds |

-continued

| Wavelength: | 590 nm |
| --- | --- |
| Enzyme concentration: | 0.025 AFAU/mL |
| Enzyme working range: | 0.01-0.04 AFAU/mL |

A folder EB-SM-0259.02/01 describing this analytical method in more detail is available upon request to Novozymes A/S, Denmark, which folder is hereby included by reference.

EXAMPLES

Example 1

Molecular Screening of Glucoamylase Genes

*Trametes cingulata* was grown on PDA2 medium and genome DNA was isolated from 0.2 g mycelium using FastDNA SPIN Kit for Soil (Qbiogene, USA) according to the manufacturer's instructions.

PCR reaction was done on genome DNA with the degenerated primers ArAF1 and ArAR3

```
ArAF1
5'-CRTRCTYDVCAACATYGG-3'       (SEQ ID NO: 7)

ArAR3
5' GTCAGARCADGGYTGRRASGTG-3'   (SEQ ID NO: 8)
``` wherein D=A or G or T; R=A or G; S=C or G; V=A or C or G; Y=C or T

The amplification reaction (13 microL) was composed of 1 microL genome DNA solution, 1 micro M primer ArAF1, 1 micro M primer ArAR3, 11 microL Extensor Hi-Fidelity PCR Master Mix (ABgene, UK). The reaction was incubated in a DNA Engine Dyad PTC-0220 (MJ Research, USA) programmed as follows: 1 cycle at 94° C. for 2 minutes; 20 cycles each at 94° C. for 30 seconds, 65° C. for 45 seconds, with an annealing temperature decline of 1° C. per cycle, and 72° C. for 1 minute 30 seconds; followed by 20 cycles each at 94° C. for 30 seconds, 45° C. for 45 seconds and 72° C. for 1 minute 30 seconds; 1 cycle at 72° C. for 7 minutes; and a hold at 4° C. The PCR product was purified using ExoSAP-IT (USB, USA) according to the manufacturer's instructions and sequenced. The sequence was subsequently compared to the *Aspergillus niger* glucoamylase gene, showing that the PCR product encoded a part of a glucoamylase.

Example 2

Molecular Screening of Glucoamylase Genes

*Pachykytospora papyracea* was grown on PDA2 medium and genome DNA was isolated from 0.2 g mycelium using FastDNA SPIN Kit for Soil (Qbiogene, USA) according to the manufacturer's instructions.

PCR reaction (PCR 1) was done on genome DNA with the degenerated primers AM2F and AM4R2:

```
AM2F
5'-TGGGGIMGNCCNCARMGNGAYGG-3'   (SEQ ID NO: 9)

AM4R2
5'-RTCYTCNGGRTANCKNCC-3'        (SEQ ID NO: 10)
``` wherein I=inosine; K=G or T; M=A or C; N=A or C or G or T; R=A or G; Y=C or T

The amplification reaction (25 microL) was composed of 1 microL genome DNA solution, 2 micro M primer AM2F, 2 micro M primer AM4R2, 22 microL Reddy PCR Master Mix (ABgene, UK). The reaction was incubated in a DNA Engine Dyad PTC-0220 (MJ Research, USA) programmed as follows: 1 cycle at 94° C. for 2 minutes; 20 cycles each at 94° C. for 1 minute, 55° C. for 1 minute, with an annealing temperature decline of 1° C. per cycle, and 72° C. for 1 minute; followed by 20 cycles each at 94° C. for 1 minute, 40° C. for 1 minute and 72° C. for 1 minute; 1 cycle at 72° C. for 7 minutes; and a hold at 4° C.

Subsequently a PCR reaction was done on an aliquot of the first PCR reaction (PCR 1) with the degenerated primers AM3F and AM4R2:

```
AM3F
5'-TAYGAYYTNYGGGARGA-3'      (SEQ ID NO: 11)

AM4R2
5'-RTCYTCNGGRTANCKNCC-3'     (SEQ ID NO: 10)
``` wherein K=G or T; N=A or C or G or T; R=A or G; Y=C or T

The amplification reaction (13 microL) was composed of 1 microL of the first PCR reaction (PCR 1), 1 microM primer AM3F, 1 micro M primer AM4R2, 11 microL Reddy PCR Master Mix (ABgene, UK). The reaction was incubated in a DNA Engine Dyad PTC-0220 (MJ Research, USA) programmed as follows: 1 cycle at 94° C. for 2 minutes; 5 cycles each at 94° C. for 45 seconds, 45° C. for 45 seconds and 72° C. for 1 minute; followed by 30 cycles each at 94° C. for 45 seconds, 40° C. for 45 seconds and 72° C. for 1 minute; 1 cycle at 72° C. for 7 minutes; and a hold at 4° C. A 0.5 kb amplified PCR band was obtained. The reaction product was isolated on a 1.0% agarose gel using TBE buffer and it was excised from the gel and purified using GFX PCR DNA and Gel band Purification Kit (Amersham Biosciences, UK). The excised band was sequenced and subsequently compared to the *Aspergillus niger* glucoamylase gene, showing that the PCR product encoded a part of a glucoamylase.

Example 3

Cloning of Glucoamylase Gene from *Trametes cingulata*

From the partial sequence of the *Trametes cingulata* glucoamylase more gene sequence was obtained with PCR based gene walking using the Vectorette Kit from SIGMA-Genosys. The gene walking was basically done as described in the manufacturer's protocol. 0.15 micro g genomic DNA of *Trametes cingulata* was digested with EcoRI, BamHI and HindIII, independently. The digested DNA was ligated with the corresponding Vectorette units supplied by the manufacturer using a DNA Engine Dyad PTC-0220 (MJ Research, USA) programmed as follows: 1 cycle at 16° C. for 60 minutes; 4 cycles each at 37° C. for 20 minutes, 16° C. for 60 minutes, 37° C. for 10 minutes; followed by 1 cycle at 16° C. for 60 minutes and a hold at 4° C. The ligation reactions were subsequent diluted 5 times with sterile water.

PCR reactions with linker-ligated genome DNA of the *Trametes cingulata* as template was performed with a DNA Engine Dyad PTC-0220 (MJ Research, USA) programmed as follows: 1 cycle at 94° C. for 2 minutes; 40 cycles each at 94° C. for 15 seconds, 72° C. for 1 minute, 72° C. for 1 minute, 1 cycle at 72° C. for 7 minutes; and a hold at 4° using the supplied Vectorette primer and primer TraF1 as shown below.

```
TraF1:
5'-TAGTCGTACTGGAACCCCACC-3'    (SEQ ID NO: 12)
```

The amplification reactions (12.5 microL) were composed of 0.5 microL of linker-ligated genome DNAs, 400 nM Vectorette primer, 400 nM TraF1 primer, 11 microL Extensor Hi-Fidelity PCR Master Mix (ABgene, UK).

A 0.5 kb amplified band was obtained by the PCR reaction from HindIII digested genome DNA. The reaction product was isolated on a 1.0% agarose gel using TBE buffer and was excised from the gel. 100 microL sterile water was added to the excised agarose gel fragment and it was melted by incubation at 95° C. for 5 minutes to release the DNA. The DNA band was reamplified by repeating the PCR reaction described above using 0.5 microL of the isolated DNA fragment instead of linker-ligated genome DNA.

After the PCR reaction the DNA was purified using ExoSAP-IT (USB, USA) according to the manufacturer's instructions and sequenced and subsequently compared to the *Aspergillus niger* glucoamylase gene, showing that it encoded a further 250 bp part of the glucoamylase gene.

In order to clone the missing parts of the glucoamylase gene from *Trametes cingulata*, PCR based gene walking was carried out using LA PCR™ in vitro Cloning Kit (TAKARA, Japan) according to the manufacturer's instructions.

Five micro g of genome DNA of *Trametes cingulata* was digested with BamHI, EcoRI, HindIII, PstI, SalI and XbaI, independently. 200 ml of ice-cold ethanol was added to the reaction mixture (50 microL) and then digested DNA was recovered by centrifugation at 15,000×g for 30 minutes at 4° C. The recovered DNA was ligated with a corresponding artificial linkers supplied by manufactures. The linker ligated DNA was recovered by adding 200 ml of ice-cold ethanol to the reaction mixture (50 microL) followed by centrifugation at 15,000×g for 30 minutes at 4° C.

PCR reactions with linker-ligated genome DNA of the *Trametes cingulata* as template was performed with a LA PCR system (TAKARA, Japan) using primer C1 and TC5' for cloning of missing 5'-glucoamylase gene and primer C1 and TC3' for cloning of missing 3'-glucoamylase gene, as shown below.

```
C1:
                                    (SEQ ID NO: 13)
5'-gtacatattgtcgttagaacgcgtaatacgactca-3'

TC5':
                                    (SEQ ID NO: 14)
5'-cgtatatgtcagcgctaccatgt-3'

TC3':
                                    (SEQ ID NO: 15)
5'-aaacgtgagcgaccattttctgt-3'
```

The amplification reactions (50 microL) were composed of 1 ng of template DNA per microL, 250 mM dNTP each, 250 nM primer, 250 nM primer, 0.1 U of LA Taq polymerase per microL in 1× buffer (TAKARA, Japan). The reactions were incubated in a DNA Engine PTC-200 (MJ-Research, Japan) programmed as follows: 1 cycle at 94° C. for 2 minutes; 30 cycles each at 94° C. for 0.5 minute, 55° C. for 2 minutes, and 72° C. for 2 minutes; 1 cycle at 72° C. for 10 minutes; and a hold at 4° C.

0.4 kb and 1.0 kb amplified bands were obtained from SalI digested genome DNA with primer C1 and TC5' and XbaI digested genome DNA with primer C1 and TC3', respectively. These reaction products were isolated on a 1.0% agarose gel using TAE buffer and was excised from the gel and purified using a QIAquick™ Gel Extraction Kit (QIAGEN Inc., Valencia, Calif.) according to the manufacturer's instructions.

The amplified DNA fragments were ligated into pT7Blue (Invitrogen, Netherlands), independently. The ligation mixture was then transformed into *E. coli* DH12alpha (GIBCO BRL, Life Technologies, USA) to create pHUda438 and pHUda439 for a 0.4 kb amplified band and a 1.0 kb amplified band, respectively. The resultant plasmids were sequenced and compared to the *Aspergillus niger* glucoamylase gene, showing that clones encode the missing parts of the glucoamylase.

Example 4

Construction of pHUda440 Expression Vector

Expression vector pHUda440 was constructed for transcription of the glucoamylase gene from *Trametes cingulata*. A PCR reaction with the genome DNA of the *Trametes cingulata* as template was performed with an Expand™ PCR system (Roche Diagnostics, Japan) using primers TFF to introduce a BamH I site and primer TFR to introduce an Xho I site, as shown below.

```
TFF:
                                    (SEQ ID NO: 16)
5'-tttggatccaccatgcgtttcacgctcctcacctcc-3'

TFR:
                                    (SEQ ID NO: 17)
5'-tttctcgagctaccgccaggtgtcattctg-3'
```

The amplification reactions (50 microL) were composed of 1 ng of template DNA per microL, 250 mM dNTP each, 250 nM primer TFF, 250 nM primer TFR, 0.1 U of Taq polymerase per microL in 1× buffer (Roche Diagnostics, Japan). The reactions were incubated in a DNA Engine PTC-200 (MJ-Research, Japan) programmed as follows: 1 cycle at 94° C. for 2 minutes; 30 cycles each at 92° C. for 1 minute, 55° C. for 1 minute, and 72° C. for 2 minutes; 1 cycle at 72° C. for 10 minutes; and a hold at 4° C.

The reaction products were isolated on a 1.0% agarose gel using TAE buffer where a 2.2 kb product band was excised from the gel and purified using a QIAquick™ Gel Extraction Kit (QIAGEN Inc., Valencia, Calif.) according to the manufacturer's instructions.

The 2.2 kb amplified DNA fragment was digested with BamHI and XhoI, and ligated into the *Aspergillus* expression cassette pCaHj483 digested with BamH I and XhoI. The ligation mixture was transformed into *E. coli* DH12alpha (GIBCO BRL, Life Technologies, USA) to create the expression plasmid pHUda440. The amplified plasmid was recovered using a QIAprep® Spin Miniprep kit (QIAGEN Inc., Valencia, Calif.) according to the manufacturer's instructions.

Plasmid pCaHj483 comprised an expression cassette based on the *Aspergillus niger* neutral amylase II promoter fused to the *Aspergillus nidulans* triose phosphate isomerase non translated leader sequence (Na2/tpi promoter) and the *Aspergillus niger* glucoamylase terminator (AMG terminator), the selective marker amdS from *Aspergillus nidulans* enabling growth on acetamide as sole nitrogen source.

Example 5

Cloning of the Glucoamylase Gene from Pachykytospora Papyraceae

In order to clone the missing parts of the glucoamylase gene from *Pachykytospora papyraceae*, PCR based gene walking was carried out using LA PCR™ in vitro Cloning Kit (TAKARA, Japan) according to the manufacturer's instructions.

Five micro g of genome DNA of *Pachykytospora papyraceae* was digested with BamHI, EcoRI, HindIII, PstI, SalI and XbaI, independently. 200 mL of ice-cold ethanol was added to the reaction mixture (50 microL) and then digested DNA was recovered by centrifugation at 15,000×g for 30 minutes at 4° C. The recovered DNA was ligated with a corresponding artificial linkers supplied by manufactures. The linker ligated DNA was recovered by adding 200 mL of ice-cold ethanol to the reaction mixture (50 microL followed by centrifugation at 15,000×g for 30 minutes at 4° C.

PCR reactions with linker-ligated genome DNA of the *Pachykytospora papyraceae* as template was performed with a LA PCR system (TAKARA, Japan) using primer C1 and PP5' for cloning of missing 5'-glucoamylase gene and primer C1 and PP3' for cloning of missing 3'-glucoamylase gene, as shown below.

```
C1:
                                           (SEQ ID NO: 13)
5'-gtacatattgtcgttagaacgcgtaatacgactca-3'

PP5':
                                           (SEQ ID NO: 18)
5'-cctccctgagtgagcgatgctgc-3'

PP3':
                                           (SEQ ID NO: 19)
5'-caactccggcctctcctccagcg-3'
```

The amplification reactions (50 microL) were composed of 1 ng of template DNA per microL, 250 mM dNTP each, 250 nM primer, 250 nM primer, 0.1 U of LA Taq polymerase per microL in 1× buffer (TAKARA, Japan). The reactions were incubated in a DNA Engine PTC-200 (MJ-Research, Japan) programmed as follows: 1 cycle at 94° C. for 2 minutes; 30 cycles each at 94° C. for 0.5 minute, 55° C. for 2 minutes, and 72° C. for 2 minutes; 1 cycle at 72° C. for 10 minutes; and a hold at 4° C.

0.5 kb and 0.9 kb amplified bands were obtained from XbaI digested genome DNA with primer C1 and PP5' and EcoRI digested genome DNA with primer C1 and PP3', respectively. These reaction products were isolated on a 1.0% agarose gel using TAE buffer and was excised from the gel and purified using a QIAquick™ Gel Extraction Kit (QIAGEN Inc., Valencia, Calif.) according to the manufacturer's instructions.

The amplified DNA fragments were ligated into pT7Blue (Invitrogen, Netherlands), independently. The ligation mixture was then transformed into *E. coli* DH12alpha (GIBCO BRL, Life Technologies, USA) to create pHUda448 and pHUda449 for a 0.5 kb amplified band and a 0.9 kb amplified band, respectively. The resultant plasmids were sequenced and compared to the *Aspergillus niger* glucoamylase gene, showing that clones encode the missing parts of the glucoamylase.

Example 6

Construction of pHUda450 Expression Vector

Expression vector pHUda450 was constructed for transcription of the glucoamylase gene from *Pachykytospora papyraceae*. A PCR reaction with the genome DNA of the *Pachykytospora papyraceae* as template was performed with an Expand™ PCR system (Roche Diagnostics, Japan) using primers PPF to introduce a BamH I site and primer PPR to introduce an Xho I site, as shown below.

```
PPF:
                                           (SEQ ID NO: 20)
5'-tttggatccaccatgcgcttcaccctcctctcctcc-3'

PPR:
                                           (SEQ ID NO: 21)
5'-tttctcgagtcaccgccaggtgtcgttctg-3'
```

The amplification reactions (50 microL) were composed of 1 ng of template DNA per microL, 250 mM dNTP each, 250 nM primer PPF, 250 nM primer PPR, 0.1 U of Taq polymerase per microL in 1× buffer (Roche Diagnostics, Japan). The reactions were incubated in a DNA Engine PTC-200 (MJ-Research, Japan) programmed as follows: 1 cycle at 94° C. for 2 minutes; 30 cycles each at 92° C. for 1 minute, 55° C. for 1 minute, and 72° C. for 2 minutes; 1 cycle at 72° C. for 10 minutes; and a hold at 4° C.

The reaction products were isolated on a 1.0% agarose gel using TAE buffer where a 2.2 kb product band was excised from the gel and purified using a QIAquick™ Gel Extraction Kit (QIAGEN Inc., Valencia, Calif.) according to the manufacturer's instructions.

The 2.2 kb amplified DNA fragment was digested with BamHI and XhoI, and ligated into the *Aspergillus* expression cassette pCaHj483 digested with BamH I and XhoI. The ligation mixture was transformed into *E. coli* DH12alpha (GIBCO BRL, Life Technologies, USA) to create the expression plasmid pHUda450. The amplified plasmid was recovered using a QIAprep® Spin Miniprep kit (QIAGEN Inc., Valencia, Calif.) according to the manufacturer's instructions.

Example 7

Expression of Glucoamylase Genes Derived from *Trametes cingulata* and *Pachykytospora papyraceae* in *Aspergillus oryzae*

*Aspergillus oryzae* strain BECh-2 was inoculated to 100 mL of YPG medium and incubated for 16 hours at 32° C. at 80 rpm. Pellets were collected and washed with 0.6 M KCl, and resuspended 20 ml 0.6 M KCl containing a commercial beta-glucanase product (GLUCANEX™, Novozymes A/S, Bagsværd, Denmark) at a final concentration of 600 microL per mL. The suspension was incubated at 32° C. and 80 rpm until protoplasts were formed, and then washed twice with STC buffer. The protoplasts were counted with a hematometer and resuspended and adjusted in an 8:2:0.1 solution of STC:STPC:DMSO to a final concentration of $2.5 \times 10^7$ protoplasts/ml. Approximately 3 micro g of pHUda440 or pHUda450 was added to 100 microL of the protoplast suspension, mixed gently, and incubated on ice for 20 minutes. One mL of SPTC was added and the protoplast suspension was incubated for 30 minutes at 37° C. After the addition of 10 mL of 50° C. COVE top agarose, the reaction was poured onto COVE agar plates and the plates were incubated at 32° C. After 5 days transformants were selected from the COVE medium.

Four randomly selected transformants were inoculated into 100 mL of MS-9 medium and cultivated at 32° C. for 1 day. Three ml of MS-9 medium was inoculated into 100 mL of MDU-pH5 medium and cultivated at 30° C. for 3 days. Supernatants were obtained by centrifugation at 3,000×g for 10 minutes.

Glucoamylase activity in the supernatant samples was determined as an increase in NADH production by glucose dehydrogenase and mutarotase reaction with generating glucose and measured the absorbance at 340 nm. Six microL of enzyme samples dissolved in 100 mM sodium acetate pH 4.3 buffer was mixed with 31 microL of 23.2 mM of maltose in 100 mM sodium acetate pH 4.3 buffer and incubated at 37° C. for 5 minutes. Then, 313 microL of color reagent (430 U of glucose dehydrogenase per liter, 9 U mutarotase per liter, 0.21 mM NAD, and 0.15 M NaCl in 0.12 M phosphate pH 7.6 buffer) was added to the reaction mixture and incubated at 37° C. for 5 minutes. Activity was measured at 340 nm on a spectrophotometer. Six microL of distilled water was used in place of the enzyme samples as controls.

Tables 1 and 2 show the glucoamylase activities of the selected transformants, relative to the activity of the host strain, Aspergillus oryzae BECh-2, which was normalized to 1.0.

TABLE 1

Shake flask results of the selected transformants expressing Trametes cingulata glucoamylase

| Strains | T. cingulata glucoamylase (AGU/ml) Relative activities |
|---|---|
| #13-1 | 180 |
| #13-2 | 199 |
| #19-1 | 148 |
| #19-2 | 169 |
| BECh-2 | 1.0 |

TABLE 2

Shake flask results of the selected transformants expressing Pachykytospora papyraceae glucaoamylase

| Strains | P. papyraceae glucoamylase (AGU/ml) Relative activities |
|---|---|
| #B11-1 | 42 |
| #B11-2 | 48 |
| #B11-3 | 36 |
| #B11-4 | 50 |
| BECh-2 | 1.0 |

Example 8

Evaluation of Trametes cingulata Glucoamylase in One-Step Fuel Ethanol Fermentations The relative performance of Trametes cingulata glucoamylase to Aspergillus niger glucoamylase and Talaromyces emersonii glucoamylase was evaluated via mini-scale fermentations. About 380 g of milled corn (ground in a pilot scale hammer mill through a 1.65 mm screen) was added to about 620 g tap water. This mixture was supplemented with 3 mL 1 g/L penicillin. The pH of this slurry was adjusted to 5.0 with 40% $H_2SO_4$. The dry solid (DS) level was determined in triplicate to be about 32%. Approximately 5 g of this slurry was added to 15 mL tubes.

A two dose dose-response was conducted with each enzyme. Dosages used were 0.3 and 0.6 nmol/g DS. Six replicates of each treatment were run.

After dosing the tubes were inoculated with 0.04 mL/g mash of yeast propagate (RED START™ yeast) that had been grown for 22.5 hours on corn mash. Tubes were capped with a screw on top which had been punctured with a small needle to allow gas release and vortexed briefly before weighing and incubation at 32° C. 70 hour fermentations were carried out and ethanol yields were determined by weighing the tubes. Tubes were vortexed briefly before weighing. The result of the experiment is shown in Table 1.

It can be seen from Table 1 the ethanol yield per gram DS is significantly higher when using the Trametes cingulata glucoamylase compared to yields for the wild-type Aspergillus niger and Talaromyces emersonii glucoamylases.

TABLE 1

| Glucoamylase | nmol/g DS | Ethanol yields |
|---|---|---|
| Trametes cingulata | 0.3 | 56.2 |
| Aspergillus niger | | 47.2 |
| Talaromyces emersonii | | 30.5 |
| Trametes cingulata | 0.6 | 100.8 |
| Aspergillus niger | | 87.2 |
| Talaromyces emersonii | | 43.4 |

Example 9

Evaluation of Pachykytospora papyracea Glucoamylase in One Step Fuel Ethanol Fermentations The relative performance of Pachykytospora papyracea glucoamylase to Aspergillus niger glucoamylase and Talaromyces emersonii glucoamylase was evaluated via mini-scale fermentations. About 380 g of milled corn (ground in a pilot scale hammer mill through a 1.65 mm screen) was added to about 620 g tap water. This mixture was supplemented with 3 mL 1 g/L penicillin. The pH of this slurry was adjusted to 5.0 with 40% $H_2SO_4$. The dry solid (DS) level was determined in triplicate to be about 32%. Approximately 5 g of this slurry was added to 15 mL tubes.

A two dose dose-response was conducted with each enzyme. Dosages used were 0.3 and 0.6 nmol/g DS. Six replicates of each treatment were run.

After dosing the tubes were inoculated with 0.04 mL/g mash of yeast propagate (RED START™ yeast) that had been grown for 22.5 hours on corn mash. Tubes were capped with a screw on top which had been punctured with a small needle to allow gas release and vortexed briefly before weighing and incubation at 32° C. 70 hour fermentations were carried out and ethanol yields were determined by weighing the tubes. Tubes were vortexed briefly before weighing. The result of the experiment is shown in Table 2.

It can be seen from Table 2 the ethanol yield per gram DS is significantly higher when using the Pachykytospora papyracea glucoamylase compared to yields for the wild-type Aspergillus niger and Talaromyces emersonii glucoamylases.

TABLE 2

| Glucoamylase | Nmol/g DS | Ethanol yields |
|---|---|---|
| Pachykytospora papyracea | 0.3 | 76.3 |
| Aspergillus niger | | 47.2 |
| Talaromyces emersonii | | 30.5 |
| Pachykytospora papyracea | 0.6 | 102.0 |
| Aspergillus niger | | 87.2 |
| Talaromyces emersonii | | 43.4 |

Example 10

*Trametes cingulata* Glucoamylase in Combination with Hybrid Alpha-Amylase a from *Rhizomucor pusillus* for One Step Fermentation All treatments were evaluated via mini-scale fermentations. 410 g of ground corn was added to 590 g tap water. This mixture was supplemented with 3.0 ml 1 g/L penicillin and 1 g of urea. The pH of this slurry was adjusted to 4.5 with 5 N NaOH (initial pH, before adjustment was about 3.8). Dry Solid (DS) level was determined to be 35%. Approximately 5 g of this slurry was added to 20 ml vials. Each vial was dosed with the appropriate amount of enzyme followed by addition of 200 micro liter yeast propagate/5 g fermentation. Actual dosages were based on the exact weight of corn slurry in each vial. Vials were incubated at 32° C. 9 replicate fermentations of each treatment were run. Three replicates were selected for 24 hour, 48 hour and 70 hour time point analysis. Vials were vortexed at 24, 48 and 70 hours. The time point analysis consisted of weighing the vials and prepping the sample for HPLC. The HPLC preparation consisted of stopping the reaction by addition of 50 micro liters of 40% $H_2SO_4$, centrifuging, and filtering through a 0.45 micro m filter. Samples awaiting HPLC analysis were stored at 4° C.

Enzymes Used in this Study:

| | % enzyme dose | | AGU/g DS | AFAU/g DS |
|---|---|---|---|---|
| Trial # | *T. cingulata* gluco-amylase | Alpha-Amylase A from *Rhizomucor pusillus* | *T. cingulata* gluco-amylase | Alpha-Amylase A from *Rhizomucor pusillus* |
| 1 | 100% | 0% | 0.43 | 0 |
| 2 | 90% | 10% | 0.387 | 0.01 |
| 3 | 80% | 20% | 0.344 | 0.02 |
| 4 | 70% | 30% | 0.301 | 0.03 |
| 5 | 60% | 40% | 0.258 | 0.04 |
| 6 | 45% | 55% | 0.1935 | 0.055 |
| 7 | 30% | 70% | 0.129 | 0.07 |
| 8 | 15% | 85% | 0.0645 | 0.085 |
| 9 | 0% | 100% | 0 | 0.1 |

Note:
*T. cingulata* glucoamylase, 49 AGU/ml) and hybrid Alpha-Amylase A from *Rhizomucor pusillus* (17 AFAU/ml) are purified enzymes from Novozymes Japan. DS = dry solid.

Results

The synergistic effect of alpha-amylase and glucoamylase is presented in a table below. When *T. cingulata* glucoamylase was used alone in one step fermentation, it produced 54.1, 81.2 and 99.0 g/l ethanol after 24, 48, and 70 hours fermentation, respectively. When the hybrid alpha-amylase A from *Rhizomucor pusillus* is used alone in fermentation, it produced 90.5, 124.6, and 138.1 g/l ethanol after 24, 48, and 70 hour fermentation, respectively.

The optimal ratio of *T. cingulata* glucoamylase to hybrid Alpha-Amylase A from *Rhizomucor pusillus* alpha-amylase is about 6.5 AGU/AFAU (Table above). Essentially similar performance in term of ethanol yield after 70 hours fermentation was observed in the range of 0.76-38.7 AGU/AFAU ratio, indicating robust performance for a broad activity ration range of the mixtures of *T. cingulata* glucoamylase to hybrid Alpha-Amylase A.

Example 11

DNA Extraction and PCR Amplification of *Leucopaxillus giganteus*

0.2-2 g of the spore forming layer (lamellas) of the fresh fruit-bodies of *Leucopaxillus giganteus* were used for genomic DNA extraction using FastDNA SPIN Kit for Soil (Qbiogene, USA) according to the manufacturer's instructions.

PCR reaction was done on genome DNA with the degenerated primers ArAF1 and ArAR3

```
ArAF1
5'-CRTRCTYDVCAACATYGG-3'        (SEQ ID NO: 7)

ArAR3
5' GTCAGARCADGGYTGRRASGTG-3'    (SEQ ID NO: 8)
``` wherein D=A or G or T; R=A or G; S=C or G; V=A or C or G; Y=C or T

The amplification reaction (13 microL) was composed of 1 microL genome DNA solution, 1 micro M primer ArAF1 (25 pmol/microL), 1 micro M primer ArAR3 (25 pmol/microL), 11 microL Extensor Hi-Fidelity PCR Master Mix (ABgene, UK). The reaction was incubated in a DNA Engine Dyad PTC-0220 (MJ Research, USA) programmed as follows: 1 cycle at 94° C. for 2 minutes; 20 cycles each at 94° C. for 30 seconds, 65° C. for 45 seconds, with an annealing temperature decline of 1° C. per cycle, and 72° C. for 1 minute 30 seconds; followed by 20 cycles each at 94° C. for 30 seconds, 45° C. for 45 seconds and 72° C. for 1 minute 30 seconds; 1 cycle at 72° C. for 7 minutes; and a hold at 4° C. The PCR product was purified using ExoSAP-IT (USB, USA) according to the manufacturer's instructions and sequenced using the primers as used in the amplification reaction. The sequence was subsequently compared to the *Aspergillus niger* glucoamylase gene, showing that the PCR product encoded a part of a glucoamylase.

| Trial # | *T. cingulata* glucoamylase AGU/g DS | Hybrid Alpha-Amylase A AFAU/g DS | Ethanol (g/l) | | | Ratio AGU/AFAU |
|---|---|---|---|---|---|---|
| | | | 24 hrs | 48 hrs | 70 hrs | |
| 1 | 0.430 | 0.000 | 54.1 | 81.2 | 99.0 | N/A |
| 2 | 0.387 | 0.010 | 88.5 | 130.7 | 145.0 | 38.70 |
| 3 | 0.344 | 0.020 | 92.9 | 132.1 | 145.9 | 17.20 |
| 4 | 0.301 | 0.030 | 96.7 | 135.3 | 146.6 | 10.03 |
| 5 | 0.258 | 0.040 | 96.1 | 136.6 | 147.1 | 6.45 |
| 6 | 0.194 | 0.055 | 97.1 | 135.5 | 145.6 | 3.52 |
| 7 | 0.129 | 0.070 | 95.4 | 132.9 | 144.6 | 1.84 |
| 8 | 0.065 | 0.085 | 93.3 | 130.4 | 142.9 | 0.76 |
| 9 | 0.000 | 0.100 | 90.5 | 124.6 | 138.1 | 0.00 |

From the partial sequence of the *Leucopaxillus giganteus* glucoamylase more gene sequence was obtained with PCR based gene walking using the Vectorette Kit from SIGMA-Genosys. The gene walking was performed as described in the manufacturer's protocol. 0.15 micro g genomic DNA of *Leucopaxillus giganteus* was digested with EcoRI, BamHI and HindIII, independently. The digested DNA was ligated with the corresponding Vectorette units supplied by the manufacture using a DNA Engine Dyad PTC-0220 (MJ Research, USA) programmed as follows: 1 cycle at 16° C. for 60 minutes; 4 cycles each at 37° C. for 20 minutes, 16° C. for 60 minutes, 37° C. for 10 minutes; followed by 1 cycle at 16° C. for 60 minutes and a hold at 4° C. The ligation reactions were subsequent diluted 5 times with sterile water.

PCR reactions with linker-ligated genome DNA of the *Leucopaxillus giganteus* as template was performed with a DNA Engine Dyad PTC-0220 (MJ Research, USA) programmed as follows: 1 cycle at 94° C. for 2 minutes; 40 cycles each at 94° C. for 15 seconds, 72° C. for 1 minute, 72° C. for 1 minute, 1 cycle at 72° C. for 7 minutes; and a hold at 4° C. using the supplied Vectorette primer and the specific *Leucopaxillus giganteus* AMG primers Nc1R2 and NC1F0, respectively, as shown below.

```
Nc1R2:
5'-GGTAGACTAGTTACCTCGTTGG-3'       (SEQ ID NO: 31)

Nc1F0:
5'-GCTTCCCTAGCCACTGCCATTGG-3'      (SEQ ID NO: 32)
```

The amplification reactions (12.5 microL) were composed of 0.5 microL of linker-ligated genome DNAs, 400 nM Vectorette primer, 400 nM *Leucopaxillus giganteus* specific primer, 11 microL Extensor Hi-Fidelity PCR Master Mix (ABgene, UK).

After the PCR reaction the PCR products were purified using ExoSAP-IT (USB, USA) according to the manufacturer's instructions and sequenced and subsequently compared to the *Aspergillus niger* glucoamylase gene.

A 1.7 kb amplified band was obtained by the PCR reaction from HindIII digested genome DNA amplified with the primer Nc1R2. Sequencing of the PCR product using this primer showed that it encoded the remaining 600 base pairs of the glucoamylase gene in the 5' direction.

A 1.8 amplified band was obtained by the PCR reaction from HindIII digested genome DNA amplified with the primer Nc1F0, Sequencing of the PCR product using this primer showed that it encoded further approximately 530 base pairs of the glucoamylase gene, however not reaching the end of the gene. Therefore, an additional sequencing primer Nc1F2, were designed based on the newly obtained additional sequence of the glucoamylase gene. Using Nc1F2 as a downstream primer of Nc1F0 on the same PCR product showed that it encoded the remaining approximately 520 base pairs of the glucoamylase gene in the 3' direction.

```
Nc1F2
5' GTTGATTTAACTTGGAGCTATGC         (SEQ ID NO: 33)
```

Example 12

Cloning and Expression of *Leucopaxillus giganteus* Glucoamylase

From the partial sequence of *Leucopaxillus giganteus* glucoamylase more gene sequence was obtained.

The following PCR cloning primers were used:

```
Forward primer:
                                   (SEQ ID NO: 34)
5' TCCCTTGGATCCAGGATGCATTTCTCTGTCCTCTC 3'
      BamHI Reverse primer:
                                   (SEQ ID NO: 35)
5' CTTATCCTCGAGCTACTTCCACGAGTCATTCTGG 3'
      XhoI
```

PCR was made with gDNA from *Leucopaxillus giganteus* as template using Phusion as polymerase and the above primers introducing respectively BamHI and XhoI. 5 micro L of the PCR product was tested in a 1% agarose gel, and showed a band at about 2.2 kb. The PCR product was purified on a QIAquick column.

The purified product and *Aspergillus* vector pENI2516 *Leucopaxillus giganteus* (see WO 2004/069872) were digested with BamHI and XhoI. The vector and insert fragments were purified from a 1% preparative agarose gel using the QIAquick method. The 2.2 kb fragment was ligated into the vector pENI2516 and transformed into TOP10 *E. coli* competent cells. The resulting plasmid was termed as pENI3372.

Transformation in *Aspergillus niger*

Protoplasts of the *Aspergillus niger* strain Mbin119 (see WO 2004/090155) were made. About 5 micro g of pENI3372 was transformed into the protoplasts. The resulting *Aspergillus niger* transformants were tested for glucoamylase activity.

Example 13

Debranching Activity Toward Pullulan of *Trametes cingulata* Glucoamylase

The alpha-1,6-debranching activity of glucoamylases derived from *Trametes cingulata*, *Athelia rolfsii*, *Aspergillus niger* and *Talaromyces emersonii* was investigated. Pullulan (MW 50,000-100,000) was dissolved in MilliQ water and added into a reaction mixture to a 3% final concentration containing 50 mM NaAc buffer, pH 4.0, with enzyme dosage of 0.42 micro g enzyme/mg pullulan at 37° C. Oligosaccharide profile was analyzed periodically by HPLC.

The result of the test is displayed in FIG. 1.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

The invention claimed is:

1. An isolated polypeptide having glucoamylase activity, selected from the group consisting of:

(a) a polypeptide with at least 90% sequence identity with amino acids 1 to 556 of SEQ ID NO: 2; and (b) a polypeptide with at least 90% sequence identity with amino acids 1 to 561 of SEQ ID NO: 37.

2. The polypeptide of claim 1, which has at least 90% sequence identity with amino acids 1 to 556 of SEQ ID NO: 2.

3. The polypeptide of claim 1, which has at least 90% sequence identity with amino acids 1 to 561 of SEQ ID NO: 37.

4. A fusion polypeptide comprising the polypeptide of claim 1 and a second polypeptide.

5. A composition comprising the polypeptide of claim 1 and an alpha-amylase.

6. The composition of claim 5, wherein the alpha-amylase is a fungal alpha-amylase.

7. The composition of claim 6, wherein the alpha-amylase is obtained from *Aspergillus, Meriplus,* or *Rhizomucor.*

8. The composition of claim 7, wherein the alpha-amylase is obtained from *Aspergillus awamori, Aspergillus kawachii, Aspergillus niger, Aspergillus oryzae, Meripilus giganteus,* or *Rhizomucor pusillus.*

9. The composition of claim 6, wherein the alpha-amylase comprises an amino acid sequence selected from the group consisting of SEQ ID NO: 28, SEQ ID NO: 29, and SEQ ID NO: 30.

10. An isolated polypeptide having glucoamylase activity, selected from the group consisting of:
    (a) a polypeptide comprising a catalytic domain with at least 90% sequence identity with amino acids 1 to 455 of SEQ ID NO: 2; and
    (b) a polypeptide comprising a catalytic domain with at least 90% sequence identity with amino acids 1 to 460 of SEQ ID NO: 37.

11. The polypeptide of claim 10, wherein the catalytic domain has at least 90% sequence identity with amino acids 1 to 455 of SEQ ID NO: 2.

12. The polypeptide of claim 10, wherein the catalytic domain has at least 90% sequence identity with amino acids 1 to 460 of SEQ ID NO: 37.

13. The polypeptide of claim 10, which comprises a foreign binding domain.

14. A fusion polypeptide comprising the polypeptide of claim 10 and a second polypeptide.

15. A composition comprising a polypeptide of claim 10 and an alpha-amylase.

16. An isolated polypeptide having carbohydrate binding activity, selected from the group consisting of:
    (a) a polypeptide comprising a binding domain with at least 90% sequence identity with amino acids 466 to 556 of SEQ ID NO: 2; and
    (b) a polypeptide comprising a binding domain with at least 90% sequence identity with amino acids 471 to 561 of SEQ ID NO: 37.

17. The polypeptide of claim 16, which further comprises a catalytic domain obtained from a glucoamylase polypeptide.

* * * * *